United States Patent
Hofmann et al.

(10) Patent No.: US 11,905,328 B2
(45) Date of Patent: *Feb. 20, 2024

(54) DUAL SPECIFICITY POLYPEPTIDE MOLECULE

(71) Applicant: Immatics Biotechnologies GmbH, Tübingen (DE)

(72) Inventors: Martin Hofmann, Tübingen (DE); Felix Unverdorben, Stuttgart (DE); Sebastian Bunk, Tübingen (DE); Dominik Maurer, Moessingen (DE)

(73) Assignee: IMMATICS BIOTECHNOLOGIES GMBH, Tuebingen (DE)

(*) Notice: Subject to any disclaimer, the term of this patent is extended or adjusted under 35 U.S.C. 154(b) by 0 days.

This patent is subject to a terminal disclaimer.

(21) Appl. No.: 16/035,403

(22) Filed: Jul. 13, 2018

(65) Prior Publication Data

US 2019/0016801 A1 Jan. 17, 2019

Related U.S. Application Data

(60) Provisional application No. 62/658,318, filed on Apr. 16, 2018, provisional application No. 62/532,713, filed on Jul. 14, 2017.

(30) Foreign Application Priority Data

| Jul. 14, 2017 | (DE) | 102017115966.5 |
| Aug. 30, 2017 | (DE) | 102017119866.0 |
| Apr. 16, 2018 | (DE) | 102018108995.3 |

(51) Int. Cl.
C07K 16/28 (2006.01)
C07K 16/46 (2006.01)
C07K 16/30 (2006.01)
C07K 16/10 (2006.01)

(52) U.S. Cl.
CPC ...... C07K 16/2809 (2013.01); C07K 16/1045 (2013.01); C07K 16/2833 (2013.01); C07K 16/30 (2013.01); C07K 16/46 (2013.01); C07K 16/468 (2013.01); C07K 2317/24 (2013.01); C07K 2317/31 (2013.01); C07K 2317/32 (2013.01); C07K 2317/626 (2013.01); C07K 2317/94 (2013.01)

(58) Field of Classification Search
None
See application file for complete search history.

(56) References Cited

U.S. PATENT DOCUMENTS

| 5,789,208 | A | 8/1998 | Sharon |
| 6,335,163 | B1 | 1/2002 | Sharon |
| 6,800,738 | B1 | 10/2004 | Carter et al. |
| 7,741,465 | B1 | 6/2010 | Eshhar et al. |
| 8,211,422 | B2 | 7/2012 | Eshhar et al. |
| 8,465,743 | B2 | 6/2013 | Rosenberg et al. |
| 8,822,196 | B2 | 9/2014 | Rosenberg et al. |
| 9,005,927 | B2 | 4/2015 | Hufton et al. |
| 9,012,181 | B2 | 4/2015 | Hufton et al. |
| 9,034,601 | B2 | 5/2015 | Hufton et al. |
| 9,040,258 | B2 | 5/2015 | Hufton et al. |
| 9,040,669 | B2 | 5/2015 | Cheung et al. |
| 9,068,980 | B2 | 6/2015 | Hufton et al. |
| 9,116,149 | B2 | 8/2015 | Hufton et al. |
| 9,284,375 | B2 | 3/2016 | Johnson et al. |
| 9,453,075 | B2 | 9/2016 | Cheung et al. |
| 9,522,955 | B2 | 12/2016 | Rosenberg et al. |
| 9,556,428 | B2 | 1/2017 | Hufton et al. |
| 9,556,438 | B2 | 1/2017 | Naldini et al. |
| 10,059,936 | B2 | 8/2018 | Hufton et al. |
| 10,098,941 | B2 | 10/2018 | Bremer et al. |
| 10,155,815 | B2 | 12/2018 | Bacac et al. |
| 10,464,988 | B2 | 11/2019 | Lu et al. |
| 10,577,599 | B2 | 3/2020 | Hufton et al. |
| 10,744,157 | B2 | 8/2020 | Sentman et al. |
| 10,755,599 | B2 | 8/2020 | Schilleci |
| 10,822,389 | B2 | 11/2020 | Lu et al. |
| 10,851,149 | B2 | 12/2020 | Siegel et al. |
| 11,028,142 | B2 | 6/2021 | Baeuerle et al. |
| 11,034,767 | B2 | 6/2021 | Ackerman et al. |
| 11,242,376 | B2 | 2/2022 | Baeuerle et al. |
| 11,325,961 | B2 | 5/2022 | Ogasawara |

(Continued)

FOREIGN PATENT DOCUMENTS

| CN | 106831996 A | 6/2017 |
| CO | 2020/0001029 A2 | 2/2020 |

(Continued)

OTHER PUBLICATIONS

Reiter et al. (Biochemistry 1994 33: 5451-5459) (Year: 1994).*

(Continued)

*Primary Examiner* — Peter J Reddig
(74) *Attorney, Agent, or Firm* — McBee Moore & Vanik IP, LLC

(57) ABSTRACT

The present invention relates to a bispecific polypeptide molecule comprising a first polypeptide chain and a second polypeptide chain providing a binding region derived from a T cell receptor (TCR) being specific for a major histocompatibility complex (MHC)-associated peptide epitope, and a binding region derived from an antibody capable of recruiting human immune effector cells by specifically binding to a surface antigen of said cells, as well as methods of making the bispecific polypeptide molecule, and uses thereof.

19 Claims, 13 Drawing Sheets

Specification includes a Sequence Listing.

(56) References Cited

U.S. PATENT DOCUMENTS

| | | |
|---|---|---|
| 11,453,726 B2 | 9/2022 | Ali et al. |
| 2006/0166875 A1 | 7/2006 | Jakobsen et al. |
| 2010/0009863 A1 | 1/2010 | Himmler et al. |
| 2010/0105136 A1 | 4/2010 | Carter et al. |
| 2010/0174053 A1 | 7/2010 | Johnson et al. |
| 2010/0317546 A1 | 12/2010 | Enzelberger et al. |
| 2011/0045007 A1 | 2/2011 | Schuurman et al. |
| 2011/0189141 A1* | 8/2011 | Kieback .................. A61P 37/06 424/93.21 |
| 2012/0252742 A1 | 10/2012 | Kranz et al. |
| 2012/0294857 A1 | 11/2012 | Sentman et al. |
| 2013/0089554 A1 | 4/2013 | Blakenship et al. |
| 2013/0095097 A1 | 4/2013 | Blakenship et al. |
| 2013/0129723 A1 | 5/2013 | Blakenship et al. |
| 2014/0242079 A1 | 8/2014 | Bacac et al. |
| 2015/0166661 A1 | 6/2015 | Chen et al. |
| 2015/0274844 A1 | 10/2015 | Blakenship et al. |
| 2016/0017038 A1 | 1/2016 | Koenig |
| 2016/0208019 A1 | 7/2016 | Bacac et al. |
| 2017/0226216 A1 | 8/2017 | Morgan et al. |
| 2018/0208657 A1 | 7/2018 | Jung et al. |
| 2018/0282390 A1 | 10/2018 | Voss et al. |
| 2019/0016801 A1 | 1/2019 | Hofmann et al. |
| 2019/0016802 A1 | 1/2019 | Hofmann et al. |
| 2019/0016803 A1 | 1/2019 | Hofmann et al. |
| 2019/0016804 A1 | 1/2019 | Hofmann et al. |
| 2019/0127470 A1 | 5/2019 | Ackerman et al. |
| 2019/0169261 A1 | 6/2019 | Ellinger et al. |
| 2019/0185539 A1 | 6/2019 | Ogasawara |
| 2019/0225710 A1 | 7/2019 | Ali et al. |
| 2019/0248865 A1 | 8/2019 | Lu et al. |
| 2019/0256571 A1 | 8/2019 | Baeuerle et al. |
| 2020/0079864 A1 | 3/2020 | Morgan et al. |
| 2020/0172619 A1 | 6/2020 | Richter et al. |
| 2020/0207828 A1 | 7/2020 | Baeuerle et al. |
| 2020/0261502 A1 | 8/2020 | Li et al. |
| 2021/0032361 A1 | 2/2021 | Hutt et al. |
| 2021/0040558 A1 | 2/2021 | Schumacher et al. |
| 2021/0041435 A1 | 2/2021 | Ogasawara |
| 2021/0130495 A1 | 5/2021 | Chand et al. |
| 2021/0214436 A1 | 7/2021 | Chang et al. |
| 2021/0363216 A1 | 11/2021 | Bossi et al. |
| 2022/0033461 A1 | 2/2022 | Voss et al. |
| 2022/0162285 A1 | 5/2022 | Ali et al. |
| 2022/0185888 A1* | 6/2022 | Hofmann ........... C07K 16/2833 |
| 2022/0195044 A1* | 6/2022 | Hofmann ........... C07K 16/2809 |
| 2022/0275043 A1 | 9/2022 | Irvine et al. |

FOREIGN PATENT DOCUMENTS

| | | |
|---|---|---|
| EP | 0403156 A1 | 12/1990 |
| EP | 2 258 719 A1 | 12/2010 |
| EP | 2 258 720 A1 | 12/2010 |
| EP | 2647707 A1 | 10/2013 |
| EP | 1 868 650 B2 | 12/2017 |
| EP | 2 985 291 A1 | 9/2018 |
| EP | 3494138 A1 | 6/2019 |
| EP | 3494984 A1 | 6/2019 |
| EP | 3770168 A1 | 1/2021 |
| EP | 3794035 A1 | 3/2021 |
| TW | I762677 B | 5/2022 |
| WO | 2011/044186 A1 | 4/2011 |
| WO | 2013/026837 A1 | 2/2013 |
| WO | 2013/037484 A2 | 3/2013 |
| WO | 2014/083004 A1 | 6/2014 |
| WO | 2014/131711 A1 | 9/2014 |
| WO | 2014/159940 A1 | 10/2014 |
| WO | 2015/077891 A1 | 6/2015 |
| WO | 2016/184592 A1 | 11/2016 |
| WO | 2017/070608 A1 | 4/2017 |
| WO | 2017/109496 A1 | 6/2017 |
| WO | 2019012138 A1 | 1/2019 |
| WO | 2019012141 A1 | 1/2019 |
| WO | 2019151392 A1 | 8/2019 |
| WO | 2019 219709 A1 | 11/2019 |
| WO | 2019231920 A1 | 12/2019 |
| WO | 2020018715 A1 | 1/2020 |
| WO | 2020057610 A1 | 3/2020 |
| WO | 2020187711 A1 | 9/2020 |
| WO | 2020229553 A1 | 11/2020 |
| WO | 2021/023658 A1 | 2/2021 |
| WO | 2021046072 A1 | 3/2021 |
| WO | 2021058807 A1 | 4/2021 |
| WO | 2021097365 A2 | 5/2021 |
| WO | 2021099360 A1 | 5/2021 |
| WO | 2021127184 A1 | 6/2021 |
| WO | 2021129559 A1 | 7/2021 |
| WO | 2021188599 A1 | 9/2021 |
| WO | 2021188601 A1 | 9/2021 |
| WO | 2021222576 A1 | 11/2021 |
| WO | 2021248198 A1 | 12/2021 |
| WO | 2022026358 A1 | 2/2022 |
| WO | 2022076788 A1 | 4/2022 |
| WO | 2022083668 A1 | 4/2022 |
| WO | 2022133592 A1 | 6/2022 |
| WO | 2022178367 A2 | 8/2022 |

OTHER PUBLICATIONS

BioLegend (OKT3, purified anti-human CD3 antibody, Jun. 12, 2013) (Year: 2013).*

Moore et al. (Blood 2011; 117 (17): 4542-4551) (Year: 2011).*

German Search Report issued in Counterpart German Application No. DE 10 2017 115 966.5, dated Jun. 28, 2018.

German Search Report issued in Counterpart German Application No. DE 10 2017 119 866.0, dated Jun. 27, 2018.

Liqin Liu, et al. MGD011, A CD19 × CD3 Dual-Affinity Retargeting Bi-specific Molecule Incorporating Extended Circulating Half-Life for the Treatment of B-Cell Malignancies. Clinical Cancer Research. vol. 23, No. 6. Sep. 23, 2016. pp. 1506-1518. XP055503218. DOI: 10.1158/1078-0432.CCR-16-0666.

Ulrich Brinkmann et al. The making of bispecific antibodies. MABS. vol. 9, No. 2. Jan. 10, 2017. pp. 182-212. XP055374463. DOI: 10.1080/19420862.2016.1268307.

C. Rader. DARTs take aim at BiTEs. Blood. vol. 117, No. 17. Apr. 28, 2011. pp. 4403-4404. XP055199549. DOI: 10.1182/blood-2011-02-337691.

International Search Report issued in counterpart International Application No. PCT/EP2018/069151, dated Sep. 14, 2018.

International Search Report issued in counterpart International Application No. PCT/EP2018/069157, dated Sep. 14, 2018.

William E. Paul,M.D., "Fundamental Immunology", 3rd Edition, 1993, pp. 292-295.

Stuart Rudikoff et al., "Single amino acid substitution altering antigen-binding specificity", Proc. Natl. Acad. Sci. USA, Mar. 1982, pp. 1979-1983, vol. 79, No. 6.

P. M. Colman, "Effects of amino acid sequence changes on antibody-antigen interactions", Research in Immunology, 1994, pp. 33-36, vol. 145.

Florence Casset et al., "A peptide mimetic of an anti-CD4 monoclonal antibody by rational design", Biochemical and Biophysical Research Communications, 2003, pp. 198-205, vol. 307.

Charles A. Janeway, Jr. et al., "Immunobiology—The Immune System in Health and Disease", 5th Ed., Garland Science, pp. 106-108, 117-118 and 260-263.

K. Christopher Garcia et al., "How the T Cell Receptor Sees Antigen—A Structural View",Cell, Aug. 12, 2005, pp. 333-336, vol. 122.

John Miles et al., "Understanding the complexity and malleability of T-cell recognition", Immunology Cell Biol, 2015, pp. 433-441, vol. 93.

Search Report issued for European Application No. 18183508.3, dated Nov. 23, 2018.

David H. Aggen et al., "Identification and engineering of human variable regions that allow expression of stable single-chain T cell receptors", Protein Engeneering, Design & Selection, 2010, pp. 361-372, vol. 24.

(56) References Cited

OTHER PUBLICATIONS

Paul Carter, "Bispecific human IgG by design", Journal of Immunological Methods, 2001, pp. 7-15, vol. 248.

Wei et al., "Structural basis of a novel heterodimeric Fc for bispecific antibody production," Oncotarget, (2017), vol. 8, No. 31: 51037-51049.

Yang et al., "Elimination of Latently HIV-infected Cells from Antiretroviral Therapy-suppressed Subjects by Engineered Immune-mobilizing T-cell Receptors", Molecular Therapy, (2016), vol. 24, Issue 11: 1913-1925.

Shearman, Clyde W., et al. "Construction, Expression and Characterization of Humanized Antibodies Directed Against the Human α/β T Cell Receptor" The Journal of Immunology, vol. 147, No. 12, pp. 4366-4373, Dec. 15, 1991.

Kessler et al., "Efficient Identification of Novel Hla-A*0201-Presented Cytotoxic T Lymphocyte Epitopes in the Widely Expressed Tumor Antigen Prame by Proteasome-Mediated Digestion Analysis," Journal of Experimental Medicine, vol. 193, No. 1, pp. 73-88, Jan. 1, 2001.

Spel et al., "Natural killer cells facilitate PRAME-specific T-cell reactivity against neuroblastoma," Oncotarget, vol. 6, No. 34, pp. 35770-35781, Oct. 6, 2015.

Reiter et al., "Stabilization of the Fv Fragments in Recombinant Immunotoxins by Disulfide Bonds Engineered into Conserved Framework Regions," Biochemistry 1994, vol. 33, No. 18, pp. 5451-5459.

Merchant et al., "An efficient route to human bispecific IgG," Nature Biotechnology, vol. 16, pp. 677-681, Jul. 1998.

Garcia et al., "How the T Cell Receptor Sees Antigen—A Structural View," Cell, vol. 122, pp. 333-336, Aug. 12, 2005.

Aggen et al., "Identification and engineering of human variable regions that allow expression of stable single-chain T cell receptors," Protein Engineering, Design & Selection, vol. 24, No. 4, pp. 361-372, Dec. 14, 2010.

Casset et al., "A peptide mimetic of an anti-CD4 monoclonal antibody by rational design," Elsevier Science (USA), Biochemical and Biophysical Research Communications 307 (2003), pp. 198-205.

Colman et al., "A Structural View of Immune Recognition by Antibodies," Research in Immunology, vol. 145, pp. 33-36, 1994.

Janeway et al., "Immuno Biology 5: The Immune System in Health and Disease," Garland Publishing, pp. 106-108, pp. 117-118, pp. 260-263, 2001.

Miles et al., "Understanding the complexity and malleability of T-cell recognition," Immunology and Cell Biology (2015) 93, pp. 433-441, Jan. 13, 2015.

Paul et al., "Fundamental Immunology: Third Edition," Raven Press, pp. 292-295, 1993.

Rudikoff et al., "Single amino acid substitution altering antigen-binding specificity," Proc. Natl. Acad. Sci. USA, vol. 79. pp. 1979-1983, Mar. 1982.

Carter et al., "Bispecific human IgG by design," Elsevier Science B.V., Journal of Immunological Methods, vol. 248, pp. 7-15, 2001.

Moore et al., "DARTs take aim at BITEs," Inside Blood, vol. 117, No. 17, pp. 4403-1404, Apr. 28, 2011.

Li, Fang, et al. "The role antigen-specific cyrotoxic T lymphocyte in viral infections" China Tropical Medicine, vol. 8, No. 6, pp. 1047-1049, Jun. 2008, and machine translation thereof.

Root, Adam R., et al. "Development of PF-06671008, a highly potent anti-P-cadherin/anti-CD3 bispecific DART molecule with extended half-life for the treatment of cancer." Antibodies vol. 5 No. 1: 6, Mar. 2016.

Johnson, Syd, et al. "Effector cell recruitment with novel Fv-based dual-affinity re-targeting protein leads to potent tumor cytolysis and in vivo B-cell depletion." Journal of molecular biology vol. 399, No. 3, pp. 436-449, Jun. 2010.

\* cited by examiner

SEQUENCE LISTING

<160> NUMBER OF SEQ ID NOS: 63

<210> SEQ ID NO 1
<211> LENGTH: 21
<212> TYPE: PRT
<213> ORGANISM: Homo sapiens

<400> SEQUENCE: 1

Glu Pro Lys Ser Cys Asp Lys Thr His Thr Cys Pro Pro Cys Pro Ala
1               5                   10                  15

Pro Glu Leu Leu Gly
            20

<210> SEQ ID NO 2
<211> LENGTH: 19
<212> TYPE: PRT
<213> ORGANISM: Homo sapiens

<400> SEQUENCE: 2

Glu Arg Lys Cys Cys Val Glu Cys Pro Pro Cys Pro Ala Pro Pro Val
1               5                   10                  15

Ala Gly Pro

<210> SEQ ID NO 3
<211> LENGTH: 53
<212> TYPE: PRT
<213> ORGANISM: Homo sapiens

<400> SEQUENCE: 3

Glu Leu Lys Thr Pro Leu Gly Asp Thr Thr His Thr Cys Pro Arg Cys
1               5                   10                  15

Pro Glu Pro Lys Ser Cys Asp Thr Pro Pro Pro Cys Pro Arg Cys Pro
            20                  25                  30

Glu Pro Lys Ser Cys Asp Thr Pro Pro Pro Cys Pro Arg Cys Pro Ala
        35                  40                  45

Pro Glu Leu Leu Gly
        50

<210> SEQ ID NO 4
<211> LENGTH: 18
<212> TYPE: PRT
<213> ORGANISM: Homo sapiens

<400> SEQUENCE: 4

Glu Ser Lys Tyr Gly Pro Pro Cys Pro Ser Cys Pro Ala Pro Glu Phe
1               5                   10                  15

Leu Gly

<210> SEQ ID NO 5
<211> LENGTH: 103
<212> TYPE: PRT
<213> ORGANISM: Homo sapiens

<400> SEQUENCE: 5

Ala Pro Pro Val Ala Gly Pro Ser Val Phe Leu Phe Pro Pro Lys Pro
1               5                   10                  15

Lys Asp Thr Leu Met Ile Ser Arg Thr Pro Glu Val Thr Cys Val Val
            20                  25                  30

Val Asp Val Ser His Glu Asp Pro Glu Val Lys Phe Asn Trp Tyr Val
        35                  40                  45

```
Asp Gly Val Glu Val His Asn Ala Lys Thr Lys Pro Arg Glu Glu Gln
        50                  55                  60

Tyr Gln Ser Thr Tyr Arg Val Val Ser Val Leu Thr Val Leu His Gln
 65                  70                  75                  80

Asp Trp Leu Asn Gly Lys Glu Tyr Lys Cys Lys Val Ser Asn Lys Ala
                 85                  90                  95

Leu Pro Ala Ser Ile Glu Lys
            100

<210> SEQ ID NO 6
<211> LENGTH: 103
<212> TYPE: PRT
<213> ORGANISM: Homo sapiens

<400> SEQUENCE: 6

Ala Pro Pro Val Ala Gly Pro Ser Val Phe Leu Phe Pro Pro Lys Pro
 1               5                  10                  15

Lys Asp Thr Leu Met Ile Ser Arg Thr Pro Glu Val Thr Cys Val Val
            20                  25                  30

Val Asp Val Ser His Glu Asp Pro Glu Val Lys Phe Asn Trp Tyr Val
         35                  40                  45

Asp Gly Val Glu Val His Asn Ala Lys Thr Lys Pro Arg Glu Glu Gln
     50                  55                  60

Tyr Asn Ser Thr Tyr Arg Val Val Ser Val Leu Thr Val Leu His Gln
 65                  70                  75                  80

Asp Trp Leu Asn Gly Lys Glu Tyr Lys Cys Lys Val Ser Asn Lys Ala
                 85                  90                  95

Leu Pro Ala Ser Ile Glu Lys
            100

<210> SEQ ID NO 7
<211> LENGTH: 9
<212> TYPE: PRT
<213> ORGANISM: Homo sapiens

<400> SEQUENCE: 7

Ser Leu Tyr Asn Thr Val Ala Thr Leu
 1               5

<210> SEQ ID NO 8
<211> LENGTH: 480
<212> TYPE: PRT
<213> ORGANISM: Homo sapiens

<400> SEQUENCE: 8

Glu Val Gln Leu Val Glu Ser Gly Gly Gly Leu Val Gln Pro Gly Gly
 1               5                  10                  15

Ser Leu Arg Leu Ser Cys Ala Ala Ser Gly Tyr Ser Phe Thr Gly Tyr
            20                  25                  30

Thr Met Asn Trp Val Arg Gln Ala Pro Gly Lys Gly Leu Glu Trp Val
         35                  40                  45

Ala Leu Ile Asn Pro Tyr Lys Gly Val Ser Thr Tyr Asn Gln Lys Phe
     50                  55                  60

Lys Asp Arg Phe Thr Ile Ser Val Asp Lys Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Ser Gly Tyr Tyr Gly Asp Ser Asp Trp Tyr Phe Asp Val Trp
```

```
                100                 105                 110
Gly Gln Gly Thr Leu Val Thr Val Ser Ser Gly Gly Ser Gly Gly
            115                 120                 125
Gly Gly Glu Ala Gly Val Thr Gln Ser Pro Thr His Leu Ile Lys Thr
130                 135                 140
Arg Gly Gln Gln Val Thr Leu Arg Cys Ser Pro Lys Ser Gly His Asp
145                 150                 155                 160
Thr Val Ser Trp Tyr Gln Gln Ala Leu Gly Gln Gly Pro Gln Phe Ile
                165                 170                 175
Phe Gln Tyr Val Arg Gly Glu Glu Arg Gln Arg Gly Asn Phe Pro Asp
            180                 185                 190
Arg Phe Ser Gly His Gln Tyr Pro Asn Tyr Ser Ser Glu Leu Asn Ile
        195                 200                 205
Asn Ala Leu Leu Leu Gly Asp Ser Ala Leu Tyr Leu Cys Ala Ser Ser
    210                 215                 220
Asp Thr Val Ser Tyr Glu Gln Tyr Phe Gly Pro Gly Ile Arg Leu Thr
225                 230                 235                 240
Val Thr Glu Asp Leu Lys Asn Gly Glu Pro Lys Ser Ser Asp Lys Thr
                245                 250                 255
His Thr Cys Pro Pro Cys Pro Ala Pro Glu Phe Leu Gly Gly Pro Ser
            260                 265                 270
Val Phe Leu Phe Pro Pro Lys Pro Lys Asp Thr Leu Met Ile Ser Arg
        275                 280                 285
Thr Pro Glu Val Thr Cys Val Val Val Asp Val Ser Gln Glu Asp Pro
    290                 295                 300
Glu Val Gln Phe Asn Trp Tyr Val Asp Gly Val Glu Val His Asn Ala
305                 310                 315                 320
Lys Thr Lys Pro Arg Glu Glu Gln Phe Gln Ser Thr Tyr Arg Val Val
                325                 330                 335
Ser Val Leu Thr Val Leu His Gln Asp Trp Leu Asn Gly Lys Glu Tyr
            340                 345                 350
Lys Cys Lys Val Ser Asn Lys Gly Leu Pro Ser Ser Ile Glu Lys Thr
        355                 360                 365
Ile Ser Lys Ala Lys Gly Gln Pro Arg Glu Pro Gln Val Tyr Thr Leu
    370                 375                 380
Pro Pro Ser Gln Glu Glu Met Thr Lys Asn Gln Val Ser Leu Trp Cys
385                 390                 395                 400
Leu Val Lys Gly Phe Tyr Pro Ser Asp Ile Ala Val Glu Trp Glu Ser
                405                 410                 415
Asn Gly Gln Pro Glu Asn Asn Tyr Lys Thr Thr Pro Pro Val Leu Asp
            420                 425                 430
Ser Asp Gly Ser Phe Phe Leu Tyr Ser Arg Leu Thr Val Asp Lys Ser
        435                 440                 445
Arg Trp Gln Glu Gly Asn Val Phe Ser Cys Ser Val Met His Glu Ala
    450                 455                 460
Leu His Asn His Tyr Thr Gln Lys Ser Leu Ser Leu Ser Leu Gly Lys
465                 470                 475                 480

<210> SEQ ID NO 9
<211> LENGTH: 461
<212> TYPE: PRT
<213> ORGANISM: Homo sapiens

<400> SEQUENCE: 9
```

```
Gln Lys Glu Val Glu Gln Asn Ser Gly Pro Leu Ser Val Pro Glu Gly
  1               5                  10                 15

Ala Ile Ala Ser Leu Asn Cys Thr Tyr Ser Asp Arg Gly Ser Gln Ser
             20                  25                  30

Phe Phe Trp Tyr Arg Gln Tyr Ser Gly Lys Ser Pro Glu Leu Ile Met
         35                  40                  45

Ser Ile Tyr Ser Asn Gly Asp Lys Glu Asp Gly Arg Phe Thr Ala Gln
     50                  55                  60

Leu Asn Lys Ala Ser Gln Tyr Ile Ser Leu Leu Ile Arg Asp Ser Lys
 65                  70                  75                  80

Leu Ser Asp Ser Ala Thr Tyr Leu Cys Ala Val Arg Gly Ala His Asp
                 85                  90                  95

Tyr Ala Leu Asn Phe Gly Lys Gly Thr Ser Leu Leu Val Thr Pro His
             100                 105                 110

Ile Gly Gly Gly Ser Gly Gly Gly Asp Ile Gln Met Thr Gln Ser
             115                 120                 125

Pro Ser Ser Leu Ser Ala Ser Val Gly Asp Arg Val Thr Ile Thr Cys
         130                 135                 140

Arg Ala Ser Gln Asp Ile Arg Asn Tyr Leu Asn Trp Tyr Gln Gln Lys
145                 150                 155                 160

Pro Gly Lys Ala Pro Lys Leu Leu Ile Tyr Tyr Thr Ser Arg Leu Glu
             165                 170                 175

Ser Gly Val Pro Ser Arg Phe Ser Gly Ser Gly Ser Gly Thr Asp Tyr
             180                 185                 190

Thr Leu Thr Ile Ser Ser Leu Gln Pro Glu Asp Phe Ala Thr Tyr Tyr
         195                 200                 205

Cys Gln Gln Gly Asn Thr Leu Pro Trp Thr Phe Gly Gln Gly Thr Lys
    210                 215                 220

Val Glu Ile Lys Gly Glu Pro Lys Ser Ser Asp Lys Thr His Thr Cys
225                 230                 235                 240

Pro Pro Cys Pro Ala Pro Glu Phe Leu Gly Gly Pro Ser Val Phe Leu
             245                 250                 255

Phe Pro Pro Lys Pro Lys Asp Thr Leu Met Ile Ser Arg Thr Pro Glu
             260                 265                 270

Val Thr Cys Val Val Val Asp Val Ser Gln Glu Asp Pro Glu Val Gln
         275                 280                 285

Phe Asn Trp Tyr Val Asp Gly Val Glu Val His Asn Ala Lys Thr Lys
    290                 295                 300

Pro Arg Glu Glu Gln Phe Gln Ser Thr Tyr Arg Val Val Ser Val Leu
305                 310                 315                 320

Thr Val Leu His Gln Asp Trp Leu Asn Gly Lys Glu Tyr Lys Cys Lys
             325                 330                 335

Val Ser Asn Lys Gly Leu Pro Ser Ser Ile Glu Lys Thr Ile Ser Lys
             340                 345                 350

Ala Lys Gly Gln Pro Arg Glu Pro Gln Val Tyr Thr Leu Pro Pro Ser
         355                 360                 365

Gln Glu Glu Met Thr Lys Asn Gln Val Ser Leu Ser Cys Ala Val Lys
    370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
             405                 410                 415

Ser Phe Phe Leu Val Ser Arg Leu Thr Val Asp Lys Ser Arg Trp Gln
```

```
            420             425             430
Glu Gly Asn Val Phe Ser Cys Ser Val Met His Glu Ala Leu His Asn
        435                 440                 445
His Tyr Thr Gln Lys Ser Leu Ser Leu Ser Leu Gly Lys
    450                 455                 460

<210> SEQ ID NO 10
<211> LENGTH: 478
<212> TYPE: PRT
<213> ORGANISM: Homo sapiens

<400> SEQUENCE: 10

Glu Val Gln Leu Val Glu Ser Gly Gly Gly Leu Val Gln Pro Gly Gly
1               5                   10                  15
Ser Leu Arg Leu Ser Cys Ala Ala Ser Gly Tyr Ser Phe Thr Gly Tyr
            20                  25                  30
Thr Met Asn Trp Val Arg Gln Ala Pro Gly Lys Gly Leu Glu Trp Val
        35                  40                  45
Ala Leu Ile Asn Pro Tyr Lys Gly Val Ser Thr Tyr Asn Gln Lys Phe
    50                  55                  60
Lys Asp Arg Phe Thr Ile Ser Val Asp Lys Ser Lys Asn Thr Ala Tyr
65                  70                  75                  80
Leu Gln Met Asn Ser Leu Arg Ala Glu Asp Thr Ala Val Tyr Tyr Cys
                85                  90                  95
Ala Arg Ser Gly Tyr Tyr Gly Asp Ser Asp Trp Tyr Phe Asp Val Trp
            100                 105                 110
Gly Gln Gly Thr Leu Val Thr Val Ser Ser Gly Gly Gly Ser Gly Gly
        115                 120                 125
Gly Gly Glu Ala Gly Val Thr Gln Ser Pro Thr His Leu Ile Lys Thr
    130                 135                 140
Arg Gly Gln Gln Val Thr Leu Arg Cys Ser Pro Lys Ser Gly His Asp
145                 150                 155                 160
Thr Val Ser Trp Tyr Gln Gln Ala Leu Gly Gln Gly Pro Gln Phe Ile
                165                 170                 175
Phe Gln Tyr Val Arg Gly Glu Glu Arg Gln Arg Gly Asn Phe Pro Asp
            180                 185                 190
Arg Phe Ser Gly His Gln Tyr Pro Asn Tyr Ser Ser Glu Leu Asn Ile
        195                 200                 205
Asn Ala Leu Leu Leu Gly Asp Ser Ala Leu Tyr Leu Cys Ala Ser Ser
    210                 215                 220
Asp Thr Val Ser Tyr Glu Gln Tyr Phe Gly Pro Gly Ile Arg Leu Thr
225                 230                 235                 240
Val Thr Glu Asp Leu Lys Asn Glu Pro Lys Ser Ser Asp Lys Thr His
                245                 250                 255
Thr Cys Pro Pro Cys Pro Ala Pro Val Ala Gly Pro Ser Val Phe
            260                 265                 270
Leu Phe Pro Pro Lys Pro Lys Asp Thr Leu Met Ile Ser Arg Thr Pro
        275                 280                 285
Glu Val Thr Cys Val Val Val Asp Val Ser His Glu Asp Pro Glu Val
    290                 295                 300
Lys Phe Asn Trp Tyr Val Asp Gly Val Glu Val His Asn Ala Lys Thr
305                 310                 315                 320
Lys Pro Arg Glu Glu Gln Tyr Gln Ser Thr Tyr Arg Val Val Ser Val
                325                 330                 335
```

Leu Thr Val Leu His Gln Asp Trp Leu Asn Gly Lys Glu Tyr Lys Cys
            340                 345                 350

Lys Val Ser Asn Lys Ala Leu Pro Ala Ser Ile Glu Lys Thr Ile Ser
            355                 360                 365

Lys Ala Lys Gly Gln Pro Arg Glu Pro Gln Val Tyr Thr Leu Pro Pro
            370                 375                 380

Ser Arg Asp Glu Leu Thr Lys Asn Gln Val Ser Leu Trp Cys Leu Val
385                 390                 395                 400

Lys Gly Phe Tyr Pro Ser Asp Ile Ala Val Glu Trp Glu Ser Asn Gly
                    405                 410                 415

Gln Pro Glu Asn Asn Tyr Lys Thr Thr Pro Pro Val Leu Asp Ser Asp
            420                 425                 430

Gly Ser Phe Phe Leu Tyr Ser Lys Leu Thr Val Asp Lys Ser Arg Trp
            435                 440                 445

Gln Gln Gly Asn Val Phe Ser Cys Ser Val Met His Glu Ala Leu His
            450                 455                 460

Asn His Tyr Thr Gln Lys Ser Leu Ser Leu Ser Pro Gly Lys
465                 470                 475

<210> SEQ ID NO 11
<211> LENGTH: 459
<212> TYPE: PRT
<213> ORGANISM: Homo sapiens

<400> SEQUENCE: 11

Gln Lys Glu Val Glu Gln Asn Ser Gly Pro Leu Ser Val Pro Glu Gly
1               5                   10                  15

Ala Ile Ala Ser Leu Asn Cys Thr Tyr Ser Asp Arg Gly Ser Gln Ser
            20                  25                  30

Phe Phe Trp Tyr Arg Gln Tyr Ser Gly Lys Ser Pro Glu Leu Ile Met
            35                  40                  45

Ser Ile Tyr Ser Asn Gly Asp Lys Glu Asp Gly Arg Phe Thr Ala Gln
        50                  55                  60

Leu Asn Lys Ala Ser Gln Tyr Ile Ser Leu Leu Ile Arg Asp Ser Lys
65                  70                  75                  80

Leu Ser Asp Ser Ala Thr Tyr Leu Cys Ala Val Arg Gly Ala His Asp
                85                  90                  95

Tyr Ala Leu Asn Phe Gly Lys Gly Thr Ser Leu Leu Val Thr Pro His
            100                 105                 110

Ile Gly Gly Gly Ser Gly Gly Gly Gly Asp Ile Gln Met Thr Gln Ser
            115                 120                 125

Pro Ser Ser Leu Ser Ala Ser Val Gly Asp Arg Val Thr Ile Thr Cys
            130                 135                 140

Arg Ala Ser Gln Asp Ile Arg Asn Tyr Leu Asn Trp Tyr Gln Gln Lys
145                 150                 155                 160

Pro Gly Lys Ala Pro Lys Leu Leu Ile Tyr Tyr Thr Ser Arg Leu Glu
                165                 170                 175

Ser Gly Val Pro Ser Arg Phe Ser Gly Ser Gly Ser Gly Thr Asp Tyr
            180                 185                 190

Thr Leu Thr Ile Ser Ser Leu Gln Pro Glu Asp Phe Ala Thr Tyr Tyr
            195                 200                 205

Cys Gln Gln Gly Asn Thr Leu Pro Trp Thr Phe Gly Gln Gly Thr Lys
            210                 215                 220

Val Glu Ile Lys Glu Pro Lys Ser Ser Asp Lys Thr His Thr Cys Pro
225                 230                 235                 240

```
Pro Cys Pro Ala Pro Val Ala Gly Pro Ser Val Phe Leu Phe Pro
            245                 250                 255

Pro Lys Pro Lys Asp Thr Leu Met Ile Ser Arg Thr Pro Glu Val Thr
        260                 265                 270

Cys Val Val Val Asp Val Ser His Glu Asp Pro Glu Val Lys Phe Asn
    275                 280                 285

Trp Tyr Val Asp Gly Val Glu Val His Asn Ala Lys Thr Lys Pro Arg
    290                 295                 300

Glu Glu Gln Tyr Gln Ser Thr Tyr Arg Val Val Ser Val Leu Thr Val
305                 310                 315                 320

Leu His Gln Asp Trp Leu Asn Gly Lys Glu Tyr Lys Cys Lys Val Ser
                325                 330                 335

Asn Lys Ala Leu Pro Ala Ser Ile Glu Lys Thr Ile Ser Lys Ala Lys
                340                 345                 350

Gly Gln Pro Arg Glu Pro Gln Val Tyr Thr Leu Pro Pro Ser Arg Asp
                355                 360                 365

Glu Leu Thr Lys Asn Gln Val Ser Leu Ser Cys Ala Val Lys Gly Phe
370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
                405                 410                 415

Phe Leu Val Ser Lys Leu Thr Val Asp Lys Ser Arg Trp Gln Gln Gly
                420                 425                 430

Asn Val Phe Ser Cys Ser Val Met His Glu Ala Leu His Asn His Tyr
                435                 440                 445

Thr Gln Lys Ser Leu Ser Leu Ser Pro Gly Lys
                450                 455

<210> SEQ ID NO 12
<211> LENGTH: 478
<212> TYPE: PRT
<213> ORGANISM: Homo sapiens

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
            20                  25                  30

Thr Met Asn Trp Val Arg Gln Ala Pro Gly Lys Gly Leu Glu Trp Val
        35                  40                  45

Ala Leu Ile Asn Pro Tyr Lys Gly Val Ser Thr Tyr Asn Gln Lys Phe
    50                  55                  60

Lys Asp Arg Phe Thr Ile Ser Val Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Gly Tyr Tyr Gly Asp Ser Asp Trp Tyr Phe Asp Val Trp
            100                 105                 110

Gly Gln Gly Thr Leu Val Thr Val Ser Ser Gly Gly Ser Gly Gly
        115                 120                 125

Gly Gly Glu Ala Gly Val Thr Gln Ser Pro Thr His Leu Ile Lys Thr
    130                 135                 140

Arg Gly Gln Gln Val Thr Leu Arg Cys Ser Pro Lys Ser Gly His Asp
```

```
145                 150                 155                 160
Thr Val Ser Trp Tyr Gln Gln Ala Leu Gly Gln Gly Pro Gln Phe Ile
                165                 170                 175

Phe Gln Tyr Val Arg Gly Glu Glu Arg Gln Arg Gly Asn Phe Pro Asp
            180                 185                 190

Arg Phe Ser Gly His Gln Tyr Pro Asn Tyr Ser Ser Glu Leu Asn Ile
        195                 200                 205

Asn Ala Leu Leu Leu Gly Asp Ser Ala Leu Tyr Leu Cys Ala Ser Ser
    210                 215                 220

Asp Thr Val Ser Tyr Glu Gln Tyr Phe Gly Pro Gly Ile Arg Leu Thr
225                 230                 235                 240

Val Thr Glu Asp Leu Lys Asn Glu Pro Lys Ser Ser Asp Lys Thr His
                245                 250                 255

Thr Cys Pro Pro Cys Pro Ala Pro Pro Val Ala Gly Pro Ser Val Phe
            260                 265                 270

Leu Phe Pro Pro Lys Pro Lys Asp Thr Leu Met Ile Ser Arg Thr Pro
        275                 280                 285

Glu Val Thr Cys Val Val Val Asp Val Ser His Glu Asp Pro Glu Val
    290                 295                 300

Lys Phe Asn Trp Tyr Val Asp Gly Val Glu Val His Asn Ala Lys Thr
305                 310                 315                 320

Lys Pro Arg Glu Glu Gln Tyr Gln Ser Thr Tyr Arg Val Val Ser Val
                325                 330                 335

Leu Thr Val Leu His Gln Asp Trp Leu Asn Gly Lys Glu Tyr Lys Cys
            340                 345                 350

Lys Val Ser Asn Lys Ala Leu Pro Ala Ser Ile Glu Lys Thr Ile Ser
        355                 360                 365

Lys Ala Lys Gly Gln Pro Arg Glu Pro Gln Val Tyr Thr Leu Pro Pro
    370                 375                 380

Cys Arg Asp Glu Leu Thr Lys Asn Gln Val Ser Leu Trp Cys Leu Val
385                 390                 395                 400

Lys Gly Phe Tyr Pro Ser Asp Ile Ala Val Glu Trp Glu Ser Asn Gly
                405                 410                 415

Gln Pro Glu Asn Asn Tyr Lys Thr Thr Pro Pro Val Leu Asp Ser Asp
            420                 425                 430

Gly Ser Phe Phe Leu Tyr Ser Lys Leu Thr Val Asp Lys Ser Arg Trp
        435                 440                 445

Gln Gln Gly Asn Val Phe Ser Cys Ser Val Met His Glu Ala Leu His
    450                 455                 460

Asn His Tyr Thr Gln Lys Ser Leu Ser Leu Ser Pro Gly Lys
465                 470                 475

<210> SEQ ID NO 13
<211> LENGTH: 459
<212> TYPE: PRT
<213> ORGANISM: Homo sapiens

<400> SEQUENCE: 13

Gln Lys Glu Val Glu Gln Asn Ser Gly Pro Leu Ser Val Pro Glu Gly
1               5                   10                  15

Ala Ile Ala Ser Leu Asn Cys Thr Tyr Ser Asp Arg Gly Ser Gln Ser
            20                  25                  30

Phe Phe Trp Tyr Arg Gln Tyr Ser Gly Lys Ser Pro Glu Leu Ile Met
        35                  40                  45
```

```
Ser Ile Tyr Ser Asn Gly Asp Lys Glu Asp Gly Arg Phe Thr Ala Gln
     50                  55                  60

Leu Asn Lys Ala Ser Gln Tyr Ile Ser Leu Leu Ile Arg Asp Ser Lys
 65                  70                  75                  80

Leu Ser Asp Ser Ala Thr Tyr Leu Cys Ala Val Arg Gly Ala His Asp
                 85                  90                  95

Tyr Ala Leu Asn Phe Gly Lys Gly Thr Ser Leu Leu Val Thr Pro His
                100                 105                 110

Ile Gly Gly Gly Ser Gly Gly Gly Asp Ile Gln Met Thr Gln Ser
            115                 120                 125

Pro Ser Ser Leu Ser Ala Ser Val Gly Asp Arg Val Thr Ile Thr Cys
130                 135                 140

Arg Ala Ser Gln Asp Ile Arg Asn Tyr Leu Asn Trp Tyr Gln Gln Lys
145                 150                 155                 160

Pro Gly Lys Ala Pro Lys Leu Leu Ile Tyr Tyr Thr Ser Arg Leu Glu
                165                 170                 175

Ser Gly Val Pro Ser Arg Phe Ser Gly Ser Gly Ser Gly Thr Asp Tyr
                180                 185                 190

Thr Leu Thr Ile Ser Ser Leu Gln Pro Glu Asp Phe Ala Thr Tyr Tyr
        195                 200                 205

Cys Gln Gln Gly Asn Thr Leu Pro Trp Thr Phe Gly Gln Gly Thr Lys
210                 215                 220

Val Glu Ile Lys Glu Pro Lys Ser Ser Asp Lys Thr His Thr Cys Pro
225                 230                 235                 240

Pro Cys Pro Ala Pro Pro Val Ala Gly Pro Ser Val Phe Leu Phe Pro
                245                 250                 255

Pro Lys Pro Lys Asp Thr Leu Met Ile Ser Arg Thr Pro Glu Val Thr
                260                 265                 270

Cys Val Val Val Asp Val Ser His Glu Asp Pro Glu Val Lys Phe Asn
        275                 280                 285

Trp Tyr Val Asp Gly Val Glu Val His Asn Ala Lys Thr Lys Pro Arg
        290                 295                 300

Glu Glu Gln Tyr Gln Ser Thr Tyr Arg Val Val Ser Val Leu Thr Val
305                 310                 315                 320

Leu His Gln Asp Trp Leu Asn Gly Lys Glu Tyr Lys Cys Lys Val Ser
                325                 330                 335

Asn Lys Ala Leu Pro Ala Ser Ile Glu Lys Thr Ile Ser Lys Ala Lys
                340                 345                 350

Gly Gln Pro Arg Glu Pro Gln Val Cys Thr Leu Pro Pro Ser Arg Asp
                355                 360                 365

Glu Leu Thr Lys Asn Gln Val Ser Leu Ser Cys Ala Val Lys Gly Phe
        370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
                405                 410                 415

Phe Leu Val Ser Lys Leu Thr Val Asp Lys Ser Arg Trp Gln Gln Gly
                420                 425                 430

Asn Val Phe Ser Cys Ser Val Met His Glu Ala Leu His Asn His Tyr
            435                 440                 445

Thr Gln Lys Ser Leu Ser Leu Ser Pro Gly Lys
        450                 455
```

<210> SEQ ID NO 14
<211> LENGTH: 478
<212> TYPE: PRT
<213> ORGANISM: Homo sapiens

<400> SEQUENCE: 14

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
            20                  25                  30

Thr Met Asn Trp Val Arg Gln Ala Pro Gly Lys Cys Leu Glu Trp Val
        35                  40                  45

Ala Leu Ile Asn Pro Tyr Lys Gly Val Ser Thr Tyr Asn Gln Lys Phe
    50                  55                  60

Lys Asp Arg Phe Thr Ile Ser Val Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Gly Tyr Tyr Gly Asp Ser Asp Trp Tyr Phe Asp Val Trp
            100                 105                 110

Gly Gln Gly Thr Leu Val Thr Val Ser Ser Gly Gly Gly Ser Gly Gly
        115                 120                 125

Gly Gly Glu Ala Gly Val Thr Gln Ser Pro Thr His Leu Ile Lys Thr
    130                 135                 140

Arg Gly Gln Gln Val Thr Leu Arg Cys Ser Pro Lys Ser Gly His Asp
145                 150                 155                 160

Thr Val Ser Trp Tyr Gln Gln Ala Leu Gly Gln Gly Pro Gln Phe Ile
                165                 170                 175

Phe Gln Tyr Val Arg Gly Glu Glu Arg Gln Arg Gly Asn Phe Pro Asp
            180                 185                 190

Arg Phe Ser Gly His Gln Tyr Pro Asn Tyr Ser Ser Glu Leu Asn Ile
        195                 200                 205

Asn Ala Leu Leu Leu Gly Asp Ser Ala Leu Tyr Leu Cys Ala Ser Ser
    210                 215                 220

Asp Thr Val Ser Tyr Glu Gln Tyr Phe Gly Pro Gly Ile Arg Leu Thr
225                 230                 235                 240

Val Thr Glu Asp Leu Lys Asn Glu Pro Lys Ser Ser Asp Lys Thr His
                245                 250                 255

Thr Cys Pro Pro Cys Pro Ala Pro Pro Val Ala Gly Pro Ser Val Phe
            260                 265                 270

Leu Phe Pro Pro Lys Pro Lys Asp Thr Leu Met Ile Ser Arg Thr Pro
        275                 280                 285

Glu Val Thr Cys Val Val Val Asp Val Ser His Glu Asp Pro Glu Val
    290                 295                 300

Lys Phe Asn Trp Tyr Val Asp Gly Val Glu Val His Asn Ala Lys Thr
305                 310                 315                 320

Lys Pro Arg Glu Glu Gln Tyr Gln Ser Thr Tyr Arg Val Val Ser Val
                325                 330                 335

Leu Thr Val Leu His Gln Asp Trp Leu Asn Gly Lys Glu Tyr Lys Cys
            340                 345                 350

Lys Val Ser Asn Lys Ala Leu Pro Ala Ser Ile Glu Lys Thr Ile Ser
        355                 360                 365

Lys Ala Lys Gly Gln Pro Arg Glu Pro Gln Val Tyr Thr Leu Pro Pro
    370                 375                 380
```

```
Cys Arg Asp Glu Leu Thr Lys Asn Gln Val Ser Leu Trp Cys Leu Val
385                 390                 395                 400

Lys Gly Phe Tyr Pro Ser Asp Ile Ala Val Glu Trp Glu Ser Asn Gly
            405                 410                 415

Gln Pro Glu Asn Asn Tyr Lys Thr Thr Pro Pro Val Leu Asp Ser Asp
        420                 425                 430

Gly Ser Phe Phe Leu Tyr Ser Lys Leu Thr Val Asp Lys Ser Arg Trp
    435                 440                 445

Gln Gln Gly Asn Val Phe Ser Cys Ser Val Met His Glu Ala Leu His
450                 455                 460

Asn His Tyr Thr Gln Lys Ser Leu Ser Leu Ser Pro Gly Lys
465                 470                 475

<210> SEQ ID NO 15
<211> LENGTH: 459
<212> TYPE: PRT
<213> ORGANISM: Homo sapiens

<400> SEQUENCE: 15

Gln Lys Glu Val Glu Gln Asn Ser Gly Pro Leu Ser Val Pro Glu Gly
1               5                   10                  15

Ala Ile Ala Ser Leu Asn Cys Thr Tyr Ser Asp Arg Gly Ser Gln Ser
            20                  25                  30

Phe Phe Trp Tyr Arg Gln Tyr Ser Gly Lys Ser Pro Glu Leu Ile Met
        35                  40                  45

Ser Ile Tyr Ser Asn Gly Asp Lys Glu Asp Gly Arg Phe Thr Ala Gln
    50                  55                  60

Leu Asn Lys Ala Ser Gln Tyr Ile Ser Leu Leu Ile Arg Asp Ser Lys
65                  70                  75                  80

Leu Ser Asp Ser Ala Thr Tyr Leu Cys Ala Val Arg Gly Ala His Asp
                85                  90                  95

Tyr Ala Leu Asn Phe Gly Lys Gly Thr Ser Leu Leu Val Thr Pro His
            100                 105                 110

Ile Gly Gly Gly Ser Gly Gly Gly Gly Asp Ile Gln Met Thr Gln Ser
        115                 120                 125

Pro Ser Ser Leu Ser Ala Ser Val Gly Asp Arg Val Thr Ile Thr Cys
    130                 135                 140

Arg Ala Ser Gln Asp Ile Arg Asn Tyr Leu Asn Trp Tyr Gln Gln Lys
145                 150                 155                 160

Pro Gly Lys Ala Pro Lys Leu Leu Ile Tyr Tyr Thr Ser Arg Leu Glu
                165                 170                 175

Ser Gly Val Pro Ser Arg Phe Ser Gly Ser Gly Ser Gly Thr Asp Tyr
            180                 185                 190

Thr Leu Thr Ile Ser Ser Leu Gln Pro Glu Asp Phe Ala Thr Tyr Tyr
        195                 200                 205

Cys Gln Gln Gly Asn Thr Leu Pro Trp Thr Phe Gly Cys Gly Thr Lys
    210                 215                 220

Val Glu Ile Lys Glu Pro Lys Ser Ser Asp Lys Thr His Thr Cys Pro
225                 230                 235                 240

Pro Cys Pro Ala Pro Pro Val Ala Gly Pro Ser Val Phe Leu Phe Pro
                245                 250                 255

Pro Lys Pro Lys Asp Thr Leu Met Ile Ser Arg Thr Pro Glu Val Thr
            260                 265                 270

Cys Val Val Val Asp Val Ser His Glu Asp Pro Glu Val Lys Phe Asn
        275                 280                 285
```

Trp Tyr Val Asp Gly Val Glu Val His Asn Ala Lys Thr Lys Pro Arg
            290                 295                 300
Glu Glu Gln Tyr Gln Ser Thr Tyr Arg Val Val Ser Val Leu Thr Val
305                 310                 315                 320
Leu His Gln Asp Trp Leu Asn Gly Lys Glu Tyr Lys Cys Lys Val Ser
                325                 330                 335
Asn Lys Ala Leu Pro Ala Ser Ile Glu Lys Thr Ile Ser Lys Ala Lys
                340                 345                 350
Gly Gln Pro Arg Glu Pro Gln Val Cys Thr Leu Pro Pro Ser Arg Asp
                355                 360                 365
Glu Leu Thr Lys Asn Gln Val Ser Leu Ser Cys Ala Val Lys Gly Phe
                370                 375                 380
Tyr Pro Ser Asp Ile Ala Val Glu Trp Glu Ser Asn Gly Gln Pro Glu
385                 390                 395                 400
Asn Asn Tyr Lys Thr Thr Pro Pro Val Leu Asp Ser Asp Gly Ser Phe
                405                 410                 415
Phe Leu Val Ser Lys Leu Thr Val Asp Lys Ser Arg Trp Gln Gln Gly
                420                 425                 430
Asn Val Phe Ser Cys Ser Val Met His Glu Ala Leu His Asn His Tyr
                435                 440                 445
Thr Gln Lys Ser Leu Ser Leu Ser Pro Gly Lys
        450                 455

<210> SEQ ID NO 16
<211> LENGTH: 474
<212> TYPE: PRT
<213> ORGANISM: Homo sapiens

<400> SEQUENCE: 16

Gln Lys Glu Val Glu Gln Asn Ser Gly Pro Leu Ser Val Pro Glu Gly
1               5                   10                  15
Ala Ile Ala Ser Leu Asn Cys Thr Tyr Ser Asp Arg Gly Ser Gln Ser
                20                  25                  30
Phe Phe Trp Tyr Arg Gln Tyr Ser Gly Lys Ser Pro Glu Leu Ile Met
            35                  40                  45
Ser Ile Tyr Ser Asn Gly Asp Lys Glu Asp Gly Arg Phe Thr Ala Gln
        50                  55                  60
Leu Asn Lys Ala Ser Gln Tyr Ile Ser Leu Leu Ile Arg Asp Ser Lys
65                  70                  75                  80
Leu Ser Asp Ser Ala Thr Tyr Leu Cys Ala Val Arg Gly Ala His Asp
                85                  90                  95
Tyr Ala Leu Asn Phe Gly Lys Gly Thr Ser Leu Leu Val Thr Pro His
                100                 105                 110
Ile Gly Gly Gly Ser Gly Gly Gly Gly Glu Val Gln Leu Val Glu Ser
            115                 120                 125
Gly Gly Gly Leu Val Gln Pro Gly Gly Ser Leu Arg Leu Ser Cys Ala
        130                 135                 140
Ala Ser Gly Tyr Ser Phe Thr Gly Tyr Thr Met Asn Trp Val Arg Gln
145                 150                 155                 160
Ala Pro Gly Lys Cys Leu Glu Trp Val Ala Leu Ile Asn Pro Tyr Lys
                165                 170                 175
Gly Val Ser Thr Tyr Asn Gln Lys Phe Lys Asp Arg Phe Thr Ile Ser
                180                 185                 190
Val Asp Lys Ser Lys Asn Thr Ala Tyr Leu Gln Met Asn Ser Leu Arg

```
            195                 200                 205
Ala Glu Asp Thr Ala Val Tyr Tyr Cys Ala Arg Ser Gly Tyr Tyr Gly
210                 215                 220

Asp Ser Asp Trp Tyr Phe Asp Val Trp Gly Gln Gly Thr Leu Val Thr
225                 230                 235                 240

Val Ser Ser Glu Pro Lys Ser Ser Asp Lys Thr His Thr Cys Pro Pro
            245                 250                 255

Cys Pro Ala Pro Pro Val Ala Gly Pro Ser Val Phe Leu Phe Pro Pro
            260                 265                 270

Lys Pro Lys Asp Thr Leu Met Ile Ser Arg Thr Pro Glu Val Thr Cys
            275                 280                 285

Val Val Val Asp Val Ser His Glu Asp Pro Glu Val Lys Phe Asn Trp
290                 295                 300

Tyr Val Asp Gly Val Glu Val His Asn Ala Lys Thr Lys Pro Arg Glu
305                 310                 315                 320

Glu Gln Tyr Gln Ser Thr Tyr Arg Val Val Ser Val Leu Thr Val Leu
            325                 330                 335

His Gln Asp Trp Leu Asn Gly Lys Glu Tyr Lys Cys Lys Val Ser Asn
            340                 345                 350

Lys Ala Leu Pro Ala Ser Ile Glu Lys Thr Ile Ser Lys Ala Lys Gly
            355                 360                 365

Gln Pro Arg Glu Pro Gln Val Cys Thr Leu Pro Pro Ser Arg Asp Glu
370                 375                 380

Leu Thr Lys Asn Gln Val Ser Leu Ser Cys Ala Val Lys Gly Phe Tyr
385                 390                 395                 400

Pro Ser Asp Ile Ala Val Glu Trp Glu Ser Asn Gly Gln Pro Glu Asn
            405                 410                 415

Asn Tyr Lys Thr Thr Pro Pro Val Leu Asp Ser Asp Gly Ser Phe Phe
            420                 425                 430

Leu Val Ser Lys Leu Thr Val Asp Lys Ser Arg Trp Gln Gln Gly Asn
            435                 440                 445

Val Phe Ser Cys Ser Val Met His Glu Ala Leu His Asn His Tyr Thr
450                 455                 460

Gln Lys Ser Leu Ser Leu Ser Pro Gly Lys
465                 470

<210> SEQ ID NO 17
<211> LENGTH: 463
<212> TYPE: PRT
<213> ORGANISM: Homo sapiens

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
            20                  25                  30

Leu Asn Trp Tyr Gln Gln Lys Pro Gly Lys Ala Pro Lys Leu Leu Ile
            35                  40                  45

Tyr Tyr Thr Ser Arg Leu Glu Ser Gly Val Pro Ser Arg Phe Ser Gly
        50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95
```

-continued

```
Thr Phe Gly Cys Gly Thr Lys Val Glu Ile Lys Gly Gly Ser Gly
                100                 105                 110

Gly Gly Gly Glu Ala Gly Val Thr Gln Ser Pro Thr His Leu Ile Lys
            115                 120                 125

Thr Arg Gly Gln Gln Val Thr Leu Arg Cys Ser Pro Lys Ser Gly His
130                 135                 140

Asp Thr Val Ser Trp Tyr Gln Gln Ala Leu Gly Gln Gly Pro Gln Phe
145                 150                 155                 160

Ile Phe Gln Tyr Val Arg Gly Glu Glu Arg Gln Arg Gly Asn Phe Pro
                165                 170                 175

Asp Arg Phe Ser Gly His Gln Tyr Pro Asn Tyr Ser Ser Glu Leu Asn
            180                 185                 190

Ile Asn Ala Leu Leu Leu Gly Asp Ser Ala Leu Tyr Leu Cys Ala Ser
        195                 200                 205

Ser Asp Thr Val Ser Tyr Glu Gln Tyr Phe Gly Pro Gly Ile Arg Leu
    210                 215                 220

Thr Val Thr Glu Asp Leu Lys Asn Glu Pro Lys Ser Ser Asp Lys Thr
225                 230                 235                 240

His Thr Cys Pro Pro Cys Pro Ala Pro Pro Val Ala Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
        275                 280                 285

Val Lys Phe Asn Trp Tyr Val Asp Gly Val Glu Val His Asn Ala Lys
    290                 295                 300

Thr Lys Pro Arg Glu Glu Gln Tyr Gln Ser Thr Tyr Arg Val Val Ser
305                 310                 315                 320

Val Leu Thr Val Leu His Gln Asp Trp Leu Asn Gly Lys Glu Tyr Lys
                325                 330                 335

Cys Lys Val Ser Asn Lys Ala Leu Pro Ala Ser Ile Glu Lys Thr Ile
            340                 345                 350

Ser Lys Ala Lys Gly Gln Pro Arg Glu Pro Gln Val Tyr Thr Leu Pro
        355                 360                 365

Pro Cys Arg Asp Glu Leu Thr Lys Asn Gln Val Ser Leu Trp Cys Leu
    370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415

Asp Gly Ser Phe Phe Leu Tyr Ser Lys Leu Thr Val Asp Lys Ser Arg
            420                 425                 430

Trp Gln Gln Gly Asn Val Phe Ser Cys Ser Val Met His Glu Ala Leu
        435                 440                 445

His Asn His Tyr Thr Gln Lys Ser Leu Ser Leu Ser Pro Gly Lys
    450                 455                 460

<210> SEQ ID NO 18
<211> LENGTH: 462
<212> TYPE: PRT
<213> ORGANISM: Homo sapiens

<400> SEQUENCE: 18

Glu Ala Gly Val Thr Gln Ser Pro Thr His Leu Ile Lys Thr Arg Gly
1               5                   10                  15
```

```
Gln Gln Val Thr Leu Arg Cys Ser Pro Lys Ser Gly His Asp Thr Val
                20                  25                  30

Ser Trp Tyr Gln Gln Ala Leu Gly Gln Gly Pro Gln Phe Ile Phe Gln
            35                  40                  45

Tyr Val Arg Gly Glu Glu Arg Gln Arg Gly Asn Phe Pro Asp Arg Phe
 50                  55                  60

Ser Gly His Gln Tyr Pro Asn Tyr Ser Ser Glu Leu Asn Ile Asn Ala
 65                  70                  75                  80

Leu Leu Leu Gly Asp Ser Ala Leu Tyr Leu Cys Ala Ser Ser Asp Thr
                85                  90                  95

Val Ser Tyr Glu Gln Tyr Phe Gly Pro Gly Ile Arg Leu Thr Val Thr
            100                 105                 110

Glu Asp Leu Lys Asn Gly Gly Gly Ser Gly Gly Gly Gly Gln Ile Gln
            115                 120                 125

Met Thr Gln Ser Pro Ser Ser Leu Ser Ala Ser Val Gly Asp Arg Val
 130                 135                 140

Thr Ile Thr Cys Ser Ala Thr Ser Ser Val Ser Tyr Met His Trp Tyr
145                 150                 155                 160

Gln Gln Lys Pro Gly Lys Ala Pro Lys Arg Trp Ile Tyr Asp Thr Ser
                165                 170                 175

Lys Leu Ala Ser Gly Val Pro Ser Arg Phe Ser Gly Ser Gly Ser Gly
            180                 185                 190

Thr Asp Tyr Thr Leu Thr Ile Ser Ser Leu Gln Pro Glu Asp Ala Ala
        195                 200                 205

Thr Tyr Tyr Cys Gln Gln Trp Ser Ser Asn Pro Leu Thr Phe Gly Gly
    210                 215                 220

Gly Thr Lys Val Glu Ile Lys Glu Pro Lys Ser Ser Asp Lys Thr His
225                 230                 235                 240

Thr Cys Pro Pro Cys Pro Ala Pro Pro Val Ala Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
    290                 295                 300

Lys Pro Arg Glu Glu Gln Tyr Gln Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Ser Ile Glu Lys Thr Ile Ser
            340                 345                 350

Lys Ala Lys Gly Gln Pro Arg Glu Pro Gln Val Tyr Thr Leu Pro Pro
        355                 360                 365

Cys Arg Asp Glu Leu Thr Lys Asn Gln Val Ser Leu Trp Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430
```

```
Gln Gln Gly Asn Val Phe Ser Cys Ser Val Met His Glu Ala Leu His
            435                 440                 445

Asn His Tyr Thr Gln Lys Ser Leu Ser Leu Ser Pro Gly Lys
    450                 455                 460

<210> SEQ ID NO 19
<211> LENGTH: 472
<212> TYPE: PRT
<213> ORGANISM: Homo sapiens

<400> SEQUENCE: 19

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Lys Phe Thr Ser Tyr
            20                  25                  30

Val Met His Trp Val Arg Gln Ala Pro Gly Gln Gly Leu Glu Trp Met
        35                  40                  45

Gly Tyr Ile Asn Pro Tyr Asn Asp Val Thr Lys Tyr Ala Glu Lys Phe
    50                  55                  60

Gln Gly Arg Val Thr Leu Thr Ser Asp Thr Ser Thr Ser Thr Ala Tyr
65                  70                  75                  80

Met Glu Leu Ser Ser Leu Arg Ser Glu Asp Thr Ala Val His Tyr Cys
                85                  90                  95

Ala Arg Gly Ser Tyr Tyr Asp Tyr Asp Gly Phe Val Tyr Trp Gly Gln
            100                 105                 110

Gly Thr Leu Val Thr Val Ser Ser Gly Gly Gly Ser Gly Gly Gly Gly
        115                 120                 125

Gln Lys Glu Val Glu Gln Asn Ser Gly Pro Leu Ser Val Pro Glu Gly
    130                 135                 140

Ala Ile Ala Ser Leu Asn Cys Thr Tyr Ser Asp Arg Gly Ser Gln Ser
145                 150                 155                 160

Phe Phe Trp Tyr Arg Gln Tyr Ser Gly Lys Ser Pro Glu Leu Ile Met
                165                 170                 175

Ser Ile Tyr Ser Asn Gly Asp Lys Glu Asp Gly Arg Phe Thr Ala Gln
            180                 185                 190

Leu Asn Lys Ala Ser Gln Tyr Ile Ser Leu Leu Ile Arg Asp Ser Lys
        195                 200                 205

Leu Ser Asp Ser Ala Thr Tyr Leu Cys Ala Val Arg Gly Ala His Asp
    210                 215                 220

Tyr Ala Leu Asn Phe Gly Lys Gly Thr Ser Leu Leu Val Thr Pro His
225                 230                 235                 240

Ile Glu Pro Lys Ser Ser Asp Lys Thr His Thr Cys Pro Pro Cys Pro
                245                 250                 255

Ala Pro Pro Val Ala Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Arg Glu Glu Gln
305                 310                 315                 320

Tyr Gln Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350
```

```
Leu Pro Ala Ser Ile Glu Lys Thr Ile Ser Lys Ala Lys Gly Gln Pro
            355                 360                 365

Arg Glu Pro Gln Val Cys Thr Leu Pro Pro Ser Arg Asp Glu Leu Thr
        370                 375                 380

Lys Asn Gln Val Ser Leu Ser Cys Ala Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Val
            420                 425                 430

Ser Lys Leu Thr Val Asp Lys Ser Arg Trp Gln Gln Gly Asn Val Phe
        435                 440                 445

Ser Cys Ser Val Met His Glu Ala Leu His Asn His Tyr Thr Gln Lys
    450                 455                 460

Ser Leu Ser Leu Ser Pro Gly Lys
465                 470

<210> SEQ ID NO 20
<211> LENGTH: 467
<212> TYPE: PRT
<213> ORGANISM: Homo sapiens

<400> SEQUENCE: 20

Glu Ala Gly Val Thr Gln Ser Pro Thr His Leu Ile Lys Thr Arg Gly
1               5                   10                  15

Gln Gln Val Thr Leu Arg Cys Ser Pro Lys Ser Gly His Asp Thr Val
            20                  25                  30

Ser Trp Tyr Gln Gln Ala Leu Gly Gln Gly Pro Gln Phe Ile Phe Gln
        35                  40                  45

Tyr Val Arg Gly Glu Glu Arg Gln Arg Gly Asn Phe Pro Asp Arg Phe
    50                  55                  60

Ser Gly His Gln Tyr Pro Asn Tyr Ser Ser Glu Leu Asn Ile Asn Ala
65                  70                  75                  80

Leu Leu Leu Gly Asp Ser Ala Leu Tyr Leu Cys Ala Ser Ser Asp Thr
                85                  90                  95

Val Ser Tyr Glu Gln Tyr Phe Gly Pro Gly Ile Arg Leu Thr Val Thr
            100                 105                 110

Glu Asp Leu Lys Asn Gly Gly Gly Ser Gly Gly Gly Gly Ser Gly
            115                 120                 125

Gly Gly Gln Ile Gln Met Thr Gln Ser Pro Ser Ser Leu Ser Ala Ser
    130                 135                 140

Val Gly Asp Arg Val Thr Ile Thr Cys Ser Ala Thr Ser Ser Val Ser
145                 150                 155                 160

Tyr Met His Trp Tyr Gln Gln Lys Pro Gly Lys Ala Pro Lys Arg Trp
                165                 170                 175

Ile Tyr Asp Thr Ser Lys Leu Ala Ser Gly Val Pro Ser Arg Phe Ser
            180                 185                 190

Gly Ser Gly Ser Gly Thr Asp Tyr Thr Leu Thr Ile Ser Ser Leu Gln
        195                 200                 205

Pro Glu Asp Ala Ala Thr Tyr Tyr Cys Gln Gln Trp Ser Ser Asn Pro
    210                 215                 220

Leu Thr Phe Gly Gly Gly Thr Lys Val Glu Ile Lys Glu Pro Lys Ser
225                 230                 235                 240

Ser Asp Lys Thr His Thr Cys Pro Pro Cys Pro Ala Pro Pro Val Ala
```

```
                    245                 250                 255
Gly Pro Ser Val Phe Leu Phe Pro Pro Lys Pro Lys Asp Thr Leu Met
                260                 265                 270

Ile Ser Arg Thr Pro Glu Val Thr Cys Val Val Val Asp Val Ser His
            275                 280                 285

Glu Asp Pro Glu Val Lys Phe Asn Trp Tyr Val Asp Gly Val Glu Val
        290                 295                 300

His Asn Ala Lys Thr Lys Pro Arg Glu Glu Gln Tyr Gln Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Ser Ile
            340                 345                 350

Glu Lys Thr Ile Ser Lys Ala Lys Gly Gln Pro Arg Glu Pro Gln Val
        355                 360                 365

Tyr Thr Leu Pro Pro Cys Arg Asp Glu Leu Thr Lys Asn Gln Val Ser
    370                 375                 380

Leu Trp Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465

<210> SEQ ID NO 21
<211> LENGTH: 472
<212> TYPE: PRT
<213> ORGANISM: Homo sapiens

<400> SEQUENCE: 21

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Lys Phe Thr Ser Tyr
            20                  25                  30

Val Met His Trp Val Arg Gln Ala Pro Gly Gln Gly Leu Glu Trp Met
        35                  40                  45

Gly Tyr Ile Asn Pro Tyr Asn Asp Val Thr Lys Tyr Ala Glu Lys Phe
    50                  55                  60

Gln Gly Arg Val Thr Leu Thr Ser Asp Thr Ser Thr Ser Thr Ala Tyr
65                  70                  75                  80

Met Glu Leu Ser Ser Leu Arg Ser Glu Asp Thr Ala Val His Tyr Cys
                85                  90                  95

Ala Arg Gly Ser Tyr Tyr Asp Tyr Asp Gly Phe Val Tyr Trp Gly Gln
            100                 105                 110

Gly Thr Leu Val Thr Val Ser Ser Gly Gly Gly Ser Gly Gly Gly Gly
        115                 120                 125

Gln Lys Glu Val Glu Gln Asn Ser Gly Pro Leu Ser Val Pro Glu Gly
    130                 135                 140
```

-continued

```
Ala Ile Ala Ser Leu Asn Cys Thr Tyr Ser Asp Arg Gly Ser Gln Ser
145                 150                 155                 160

Phe Phe Trp Tyr Arg Gln Tyr Ser Gly Lys Ser Pro Glu Leu Ile Met
                165                 170                 175

Ser Ile Tyr Ser Asn Gly Asp Lys Glu Asp Gly Arg Phe Thr Ala Gln
            180                 185                 190

Leu Asn Lys Ala Ser Gln Tyr Ile Ser Leu Leu Ile Arg Asp Ser Lys
        195                 200                 205

Leu Ser Asp Ser Ala Thr Tyr Leu Cys Ala Val Arg Gly Ala His Asp
    210                 215                 220

Tyr Ala Leu Asn Phe Gly Lys Gly Thr Ser Leu Leu Val Thr Pro His
225                 230                 235                 240

Ile Glu Pro Lys Ser Ser Asp Lys Thr His Thr Cys Pro Pro Cys Pro
                245                 250                 255

Ala Pro Pro Val Ala Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Arg Glu Glu Gln
305                 310                 315                 320

Tyr Gln Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Ser Ile Glu Lys Thr Ile Ser Lys Ala Lys Gly Gln Pro
        355                 360                 365

Arg Glu Pro Gln Val Cys Thr Leu Pro Pro Ser Arg Asp Glu Leu Thr
    370                 375                 380

Lys Asn Gln Val Ser Leu Ser Cys Ala Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Val
            420                 425                 430

Ser Lys Leu Thr Val Asp Lys Ser Arg Trp Gln Gln Gly Asn Val Phe
        435                 440                 445

Ser Cys Ser Val Met His Glu Ala Leu His Asn His Tyr Thr Gln Lys
    450                 455                 460

Ser Leu Ser Leu Ser Pro Gly Lys
465                 470
```

<210> SEQ ID NO 22
<211> LENGTH: 462
<212> TYPE: PRT
<213> ORGANISM: Homo sapiens

<400> SEQUENCE: 22

```
Gln Ile Gln Met Thr Gln Ser Pro Ser Ser Leu Ser Ala Ser Val Gly
1               5                   10                  15

Asp Arg Val Thr Ile Thr Cys Ser Ala Thr Ser Ser Val Ser Tyr Met
            20                  25                  30

His Trp Tyr Gln Gln Lys Pro Gly Lys Ala Pro Lys Arg Trp Ile Tyr
        35                  40                  45
```

```
Asp Thr Ser Lys Leu Ala Ser Gly Val Pro Ser Arg Phe Ser Gly Ser
 50                  55                  60

Gly Ser Gly Thr Asp Tyr Thr Leu Thr Ile Ser Ser Leu Gln Pro Glu
 65                  70                  75                  80

Asp Ala Ala Thr Tyr Tyr Cys Gln Gln Trp Ser Ser Asn Pro Leu Thr
                 85                  90                  95

Phe Gly Gly Gly Thr Lys Val Glu Ile Lys Gly Gly Ser Gly Gly
            100                 105                 110

Gly Gly Glu Ala Gly Val Thr Gln Ser Pro Thr His Leu Ile Lys Thr
        115                 120                 125

Arg Gly Gln Gln Val Thr Leu Arg Cys Ser Pro Lys Ser Gly His Asp
    130                 135                 140

Thr Val Ser Trp Tyr Gln Gln Ala Leu Gly Gln Gly Pro Gln Phe Ile
145                 150                 155                 160

Phe Gln Tyr Val Arg Gly Glu Arg Gln Arg Gly Asn Phe Pro Asp
                165                 170                 175

Arg Phe Ser Gly His Gln Tyr Pro Asn Tyr Ser Ser Glu Leu Asn Ile
            180                 185                 190

Asn Ala Leu Leu Leu Gly Asp Ser Ala Leu Tyr Leu Cys Ala Ser Ser
    195                 200                 205

Asp Thr Val Ser Tyr Glu Gln Tyr Phe Gly Pro Gly Ile Arg Leu Thr
    210                 215                 220

Val Thr Glu Asp Leu Lys Asn Glu Pro Lys Ser Ser Asp Lys Thr His
225                 230                 235                 240

Thr Cys Pro Pro Cys Pro Ala Pro Pro Val Ala Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
            275                 280                 285

Lys Phe Asn Trp Tyr Val Asp Gly Val Glu Val His Asn Ala Lys Thr
    290                 295                 300

Lys Pro Arg Glu Glu Gln Tyr Gln Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Ser Ile Glu Lys Thr Ile Ser
            340                 345                 350

Lys Ala Lys Gly Gln Pro Arg Glu Pro Gln Val Tyr Thr Leu Pro Pro
        355                 360                 365

Cys Arg Asp Glu Leu Thr Lys Asn Gln Val Ser Leu Trp Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys
    450                 455                 460
```

<210> SEQ ID NO 23
<211> LENGTH: 472
<212> TYPE: PRT
<213> ORGANISM: Homo sapiens

<400> SEQUENCE: 23

Gln Lys Glu Val Glu Gln Asn Ser Gly Pro Leu Ser Val Pro Glu Gly
1               5                   10                  15

Ala Ile Ala Ser Leu Asn Cys Thr Tyr Ser Asp Arg Gly Ser Gln Ser
            20                  25                  30

Phe Phe Trp Tyr Arg Gln Tyr Ser Gly Lys Ser Pro Glu Leu Ile Met
        35                  40                  45

Ser Ile Tyr Ser Asn Gly Asp Lys Glu Asp Gly Arg Phe Thr Ala Gln
50                  55                  60

Leu Asn Lys Ala Ser Gln Tyr Ile Ser Leu Leu Ile Arg Asp Ser Lys
65                  70                  75                  80

Leu Ser Asp Ser Ala Thr Tyr Leu Cys Ala Val Arg Gly Ala His Asp
                85                  90                  95

Tyr Ala Leu Asn Phe Gly Lys Gly Thr Ser Leu Leu Val Thr Pro His
            100                 105                 110

Ile Gly Gly Ser Gly Gly Gly Gly Glu Val Gln Leu Val Gln Ser
        115                 120                 125

Gly Ala Glu Val Lys Lys Pro Gly Ala Ser Val Lys Val Ser Cys Lys
130                 135                 140

Ala Ser Gly Tyr Lys Phe Thr Ser Tyr Val Met His Trp Val Arg Gln
145                 150                 155                 160

Ala Pro Gly Gln Gly Leu Glu Trp Met Gly Tyr Ile Asn Pro Tyr Asn
                165                 170                 175

Asp Val Thr Lys Tyr Ala Glu Lys Phe Gln Gly Arg Val Thr Leu Thr
            180                 185                 190

Ser Asp Thr Ser Thr Ser Thr Ala Tyr Met Glu Leu Ser Ser Leu Arg
        195                 200                 205

Ser Glu Asp Thr Ala Val His Tyr Cys Ala Arg Gly Ser Tyr Tyr Asp
210                 215                 220

Tyr Asp Gly Phe Val Tyr Trp Gly Gln Gly Thr Leu Val Thr Val Ser
225                 230                 235                 240

Ser Glu Pro Lys Ser Ser Asp Lys Thr His Thr Cys Pro Pro Cys Pro
                245                 250                 255

Ala Pro Pro Val Ala Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
290                 295                 300

Asp Gly Val Glu Val His Asn Ala Lys Thr Lys Pro Arg Glu Glu Gln
305                 310                 315                 320

Tyr Gln Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Ser Ile Glu Lys Thr Ile Ser Lys Ala Lys Gly Gln Pro
        355                 360                 365

Arg Glu Pro Gln Val Cys Thr Leu Pro Pro Ser Arg Asp Glu Leu Thr
370                 375                 380

```
Lys Asn Gln Val Ser Leu Ser Cys Ala Val Lys Gly Phe Tyr Pro Ser
385                 390                 395                 400

Asp Ile Ala Val Glu Trp Glu Ser Asn Gly Gln Pro Glu Asn Asn Tyr
            405                 410                 415

Lys Thr Thr Pro Pro Val Leu Asp Ser Asp Gly Ser Phe Phe Leu Val
        420                 425                 430

Ser Lys Leu Thr Val Asp Lys Ser Arg Trp Gln Gln Gly Asn Val Phe
    435                 440                 445

Ser Cys Ser Val Met His Glu Ala Leu His Asn His Tyr Thr Gln Lys
450                 455                 460

Ser Leu Ser Leu Ser Pro Gly Lys
465                 470

<210> SEQ ID NO 24
<211> LENGTH: 468
<212> TYPE: PRT
<213> ORGANISM: Homo sapiens

<400> SEQUENCE: 24

Gln Ile Gln Met Thr Gln Ser Pro Ser Ser Leu Ser Ala Ser Val Gly
1               5                   10                  15

Asp Arg Val Thr Ile Thr Cys Ser Ala Thr Ser Ser Val Ser Tyr Met
            20                  25                  30

His Trp Tyr Gln Gln Lys Pro Gly Lys Ala Pro Lys Arg Trp Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Ala Ala Thr Tyr Tyr Cys Gln Gln Trp Ser Ser Asn Pro Leu Thr
                85                  90                  95

Phe Gly Gly Gly Thr Lys Val Glu Ile Lys Gly Gly Gly Gly Ser Gly
            100                 105                 110

Gly Gly Gly Ser Gly Gly Gly Gly Glu Ala Gly Val Thr Gln Ser Pro
        115                 120                 125

Thr His Leu Ile Lys Thr Arg Gly Gln Gln Val Thr Leu Arg Cys Ser
    130                 135                 140

Pro Lys Ser Gly His Asp Thr Val Ser Trp Tyr Gln Gln Ala Leu Gly
145                 150                 155                 160

Gln Gly Pro Gln Phe Ile Phe Gln Tyr Val Arg Gly Glu Glu Arg Gln
                165                 170                 175

Arg Gly Asn Phe Pro Asp Arg Phe Ser Gly His Gln Tyr Pro Asn Tyr
            180                 185                 190

Ser Ser Glu Leu Asn Ile Asn Ala Leu Leu Leu Gly Asp Ser Ala Leu
        195                 200                 205

Tyr Leu Cys Ala Ser Ser Asp Thr Val Ser Tyr Glu Gln Tyr Phe Gly
    210                 215                 220

Pro Gly Ile Arg Leu Thr Val Thr Glu Asp Leu Lys Asn Glu Pro Lys
225                 230                 235                 240

Ser Ser Asp Lys Thr His Thr Cys Pro Pro Cys Pro Ala Pro Pro Val
                245                 250                 255

Ala Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
```

```
                        275                 280                 285
His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Gln Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Ser
            340                 345                 350

Ile Glu Lys Thr Ile Ser Lys Ala Lys Gly Gln Pro Arg Glu Pro Gln
        355                 360                 365

Val Tyr Thr Leu Pro Pro Cys Arg Asp Glu Leu Thr Lys Asn Gln Val
    370                 375                 380

Ser Leu Trp Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly Lys
465

<210> SEQ ID NO 25
<211> LENGTH: 472
<212> TYPE: PRT
<213> ORGANISM: Homo sapiens

<400> SEQUENCE: 25

Gln Lys Glu Val Glu Gln Asn Ser Gly Pro Leu Ser Val Pro Glu Gly
1               5                   10                  15

Ala Ile Ala Ser Leu Asn Cys Thr Tyr Ser Asp Arg Gly Ser Gln Ser
            20                  25                  30

Phe Phe Trp Tyr Arg Gln Tyr Ser Gly Lys Ser Pro Glu Leu Ile Met
        35                  40                  45

Ser Ile Tyr Ser Asn Gly Asp Lys Glu Asp Gly Arg Phe Thr Ala Gln
    50                  55                  60

Leu Asn Lys Ala Ser Gln Tyr Ile Ser Leu Leu Ile Arg Asp Ser Lys
65                  70                  75                  80

Leu Ser Asp Ser Ala Thr Tyr Leu Cys Ala Val Arg Gly Ala His Asp
                85                  90                  95

Tyr Ala Leu Asn Phe Gly Lys Gly Thr Ser Leu Leu Val Thr Pro His
            100                 105                 110

Ile Gly Gly Gly Ser Gly Gly Gly Glu Val Gln Leu Val Gln Ser
        115                 120                 125

Gly Ala Glu Val Lys Lys Pro Gly Ala Ser Val Lys Val Ser Cys Lys
    130                 135                 140

Ala Ser Gly Tyr Lys Phe Thr Ser Tyr Val Met His Trp Val Arg Gln
145                 150                 155                 160

Ala Pro Gly Gln Gly Leu Glu Trp Met Gly Tyr Ile Asn Pro Tyr Asn
                165                 170                 175
```

```
Asp Val Thr Lys Tyr Ala Glu Lys Phe Gln Gly Arg Val Thr Leu Thr
            180                 185                 190

Ser Asp Thr Ser Thr Ser Thr Ala Tyr Met Glu Leu Ser Ser Leu Arg
        195                 200                 205

Ser Glu Asp Thr Ala Val His Tyr Cys Ala Arg Gly Ser Tyr Tyr Asp
    210                 215                 220

Tyr Asp Gly Phe Val Tyr Trp Gly Gln Gly Thr Leu Val Thr Val Ser
225                 230                 235                 240

Ser Glu Pro Lys Ser Ser Asp Lys Thr His Thr Cys Pro Pro Cys Pro
                245                 250                 255

Ala Pro Pro Val Ala Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Arg Glu Glu Gln
305                 310                 315                 320

Tyr Gln Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Ser Ile Glu Lys Thr Ile Ser Lys Ala Lys Gly Gln Pro
        355                 360                 365

Arg Glu Pro Gln Val Cys Thr Leu Pro Pro Ser Arg Asp Glu Leu Thr
    370                 375                 380

Lys Asn Gln Val Ser Leu Ser Cys Ala Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Val
            420                 425                 430

Ser Lys Leu Thr Val Asp Lys Ser Arg Trp Gln Gln Gly Asn Val Phe
        435                 440                 445

Ser Cys Ser Val Met His Glu Ala Leu His Asn His Tyr Thr Gln Lys
    450                 455                 460

Ser Leu Ser Leu Ser Pro Gly Lys
465                 470

<210> SEQ ID NO 26
<211> LENGTH: 231
<212> TYPE: PRT
<213> ORGANISM: Homo sapiens

<400> SEQUENCE: 26

Glu Pro Lys Ser Ser Asp Lys Thr His Thr Cys Pro Pro Cys Pro Ala
1               5                   10                  15

Pro Pro Val Ala Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Ser His Glu Asp Pro Glu Val Lys Phe Asn Trp Tyr Val Asp
    50                  55                  60

Gly Val Glu Val His Asn Ala Lys Thr Lys Pro Arg Glu Glu Gln Tyr
65                  70                  75                  80
```

```
Gln Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Ser Ile Glu Lys Thr Ile Ser Lys Ala Lys Gly Gln Pro Arg
        115                 120                 125

Glu Pro Gln Val Cys Thr Leu Pro Pro Ser Arg Asp Glu Leu Thr Lys
    130                 135                 140

Asn Gln Val Ser Leu Ser Cys Ala Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Val Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys
225                 230

<210> SEQ ID NO 27
<211> LENGTH: 231
<212> TYPE: PRT
<213> ORGANISM: Homo sapiens

<400> SEQUENCE: 27

Glu Pro Lys Ser Ser Asp Lys Thr His Thr Cys Pro Pro Cys Pro Ala
1               5                   10                  15

Pro Pro Val Ala Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Ser His Glu Asp Pro Glu Val Lys Phe Asn Trp Tyr Val Asp
50                  55                  60

Gly Val Glu Val His Asn Ala Lys Thr Lys Pro Arg Glu Glu Gln Tyr
65                  70                  75                  80

Gln Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Ser Ile Glu Lys Thr Ile Ser Lys Ala Lys Gly Gln Pro Arg
        115                 120                 125

Glu Pro Gln Val Tyr Thr Leu Pro Pro Cys Arg Asp Glu Leu Thr Lys
    130                 135                 140

Asn Gln Val Ser Leu Trp Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
```

```
                210                 215                 220

Leu Ser Leu Ser Pro Gly Lys
225                 230

<210> SEQ ID NO 28
<211> LENGTH: 113
<212> TYPE: PRT
<213> ORGANISM: Homo sapiens

<400> SEQUENCE: 28

Gln Lys Glu Val Glu Gln Asn Ser Gly Pro Leu Ser Val Pro Glu Gly
1               5                   10                  15

Ala Ile Ala Ser Leu Asn Cys Thr Tyr Ser Asp Arg Gly Ser Gln Ser
            20                  25                  30

Phe Phe Trp Tyr Arg Gln Tyr Ser Gly Lys Ser Pro Glu Leu Ile Met
        35                  40                  45

Ser Ile Tyr Ser Asn Gly Asp Lys Glu Asp Gly Arg Phe Thr Ala Gln
    50                  55                  60

Leu Asn Lys Ala Ser Gln Tyr Ile Ser Leu Leu Ile Arg Asp Ser Lys
65                  70                  75                  80

Leu Ser Asp Ser Ala Thr Tyr Leu Cys Ala Val Arg Gly Ala His Asp
                85                  90                  95

Tyr Ala Leu Asn Phe Gly Lys Gly Thr Ser Leu Leu Val Thr Pro His
            100                 105                 110

Ile

<210> SEQ ID NO 29
<211> LENGTH: 122
<212> TYPE: PRT
<213> ORGANISM: Homo sapiens

<400> SEQUENCE: 29

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
            20                  25                  30

Thr Met Asn Trp Val Arg Gln Ala Pro Gly Lys Cys Leu Glu Trp Val
        35                  40                  45

Ala Leu Ile Asn Pro Tyr Lys Gly Val Ser Thr Tyr Asn Gln Lys Phe
    50                  55                  60

Lys Asp Arg Phe Thr Ile Ser Val Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Gly Tyr Tyr Gly Asp Ser Asp Trp Tyr Phe Asp Val Trp
            100                 105                 110

Gly Gln Gly Thr Leu Val Thr Val Ser Ser
        115                 120

<210> SEQ ID NO 30
<211> LENGTH: 8
<212> TYPE: PRT
<213> ORGANISM: Homo sapiens

<400> SEQUENCE: 30

Gly Gly Gly Ser Gly Gly Gly Gly
1               5
```

```
<210> SEQ ID NO 31
<211> LENGTH: 117
<212> TYPE: PRT
<213> ORGANISM: Homo sapiens

<400> SEQUENCE: 31

Glu Ala Gly Val Thr Gln Ser Pro Thr His Leu Ile Lys Thr Arg Gly
1               5                   10                  15

Gln Gln Val Thr Leu Arg Cys Ser Pro Lys Ser Gly His Asp Thr Val
            20                  25                  30

Ser Trp Tyr Gln Gln Ala Leu Gly Gln Gly Pro Gln Phe Ile Phe Gln
        35                  40                  45

Tyr Val Arg Gly Glu Glu Arg Gln Arg Gly Asn Phe Pro Asp Arg Phe
    50                  55                  60

Ser Gly His Gln Tyr Pro Asn Tyr Ser Ser Glu Leu Asn Ile Asn Ala
65                  70                  75                  80

Leu Leu Leu Gly Asp Ser Ala Leu Tyr Leu Cys Ala Ser Ser Asp Thr
                85                  90                  95

Val Ser Tyr Glu Gln Tyr Phe Gly Pro Gly Ile Arg Leu Thr Val Thr
            100                 105                 110

Glu Asp Leu Lys Asn
            115

<210> SEQ ID NO 32
<211> LENGTH: 107
<212> TYPE: PRT
<213> ORGANISM: Homo sapiens

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Glu Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Cys Gly Thr Lys Val Glu Ile Lys
            100                 105

<210> SEQ ID NO 33
<211> LENGTH: 478
<212> TYPE: PRT
<213> ORGANISM: Homo sapiens

<400> SEQUENCE: 33

Glu Ala Gly Val Thr Gln Ser Pro Thr His Leu Ile Lys Thr Arg Gly
1               5                   10                  15

Gln Gln Val Thr Leu Arg Cys Ser Pro Lys Ser Gly His Asp Thr Val
            20                  25                  30

Ser Trp Tyr Gln Gln Ala Leu Gly Gln Gly Pro Gln Phe Ile Phe Gln
        35                  40                  45

Tyr Val Arg Gly Glu Glu Arg Gln Arg Gly Asn Phe Pro Asp Arg Phe
```

-continued

```
                50                  55                  60
Ser Gly His Gln Tyr Pro Asn Tyr Ser Ser Glu Leu Asn Ile Asn Ala
 65                  70                  75                  80

Leu Leu Leu Gly Asp Ser Ala Leu Tyr Leu Cys Ala Ser Ser Asp Thr
                 85                  90                  95

Val Ser Tyr Glu Gln Tyr Phe Gly Pro Gly Ile Arg Leu Thr Val Thr
                100                 105                 110

Glu Asp Leu Lys Asn Gly Ser Ala Asp Ala Lys Lys Asp Ala Ala
            115                 120                 125

Lys Lys Asp Gly Lys Ser Gln Lys Glu Val Glu Gln Asn Ser Gly Pro
130                 135                 140

Leu Ser Val Pro Glu Gly Ala Ile Ala Ser Leu Asn Cys Thr Tyr Ser
145                 150                 155                 160

Asp Arg Gly Ser Gln Ser Phe Phe Trp Tyr Arg Gln Tyr Ser Gly Lys
                165                 170                 175

Ser Pro Glu Leu Ile Met Ser Ile Tyr Ser Asn Gly Asp Lys Glu Asp
                180                 185                 190

Gly Arg Phe Thr Ala Gln Leu Asn Lys Ala Ser Gln Tyr Ile Ser Leu
            195                 200                 205

Leu Ile Arg Asp Ser Lys Leu Ser Asp Ser Ala Thr Tyr Leu Cys Ala
210                 215                 220

Val Arg Gly Ala His Asp Tyr Ala Leu Asn Phe Gly Lys Gly Thr Ser
225                 230                 235                 240

Leu Leu Val Thr Pro His Ile Glu Pro Lys Ser Ser Asp Lys Thr His
                245                 250                 255

Thr Cys Pro Pro Cys Pro Ala Pro Pro Val Ala Gly Pro Ser Val Phe
                260                 265                 270

Leu Phe Pro Pro Lys Pro Lys Asp Thr Leu Met Ile Ser Arg Thr Pro
            275                 280                 285

Glu Val Thr Cys Val Val Val Asp Val Ser His Glu Asp Pro Glu Val
290                 295                 300

Lys Phe Asn Trp Tyr Val Asp Gly Val Glu Val His Asn Ala Lys Thr
305                 310                 315                 320

Lys Pro Arg Glu Glu Gln Tyr Gln Ser Thr Tyr Arg Val Val Ser Val
                325                 330                 335

Leu Thr Val Leu His Gln Asp Trp Leu Asn Gly Lys Glu Tyr Lys Cys
            340                 345                 350

Lys Val Ser Asn Lys Ala Leu Pro Ala Ser Ile Glu Lys Thr Ile Ser
            355                 360                 365

Lys Ala Lys Gly Gln Pro Arg Glu Pro Gln Val Tyr Thr Leu Pro Pro
370                 375                 380

Ser Arg Asp Glu Leu Thr Lys Asn Gln Val Ser Leu Ser Cys Ala Val
385                 390                 395                 400

Lys Gly Phe Tyr Pro Ser Asp Ile Ala Val Glu Trp Glu Ser Asn Gly
                405                 410                 415

Gln Pro Glu Asn Asn Tyr Lys Thr Thr Pro Pro Val Leu Asp Ser Asp
            420                 425                 430

Gly Ser Phe Phe Leu Val Ser Lys Leu Thr Val Asp Lys Ser Arg Trp
            435                 440                 445

Gln Gln Gly Asn Val Phe Ser Cys Ser Val Met His Glu Ala Leu His
        450                 455                 460

Asn His Tyr Thr Gln Lys Ser Leu Ser Leu Ser Pro Gly Lys
465                 470                 475
```

<210> SEQ ID NO 34
<211> LENGTH: 451
<212> TYPE: PRT
<213> ORGANISM: Homo sapiens

<400> SEQUENCE: 34

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Tyr Ser Phe Thr Gly Tyr
            20                  25                  30

Thr Met Asn Trp Val Arg Gln Ala Pro Gly Lys Gly Leu Glu Trp Val
        35                  40                  45

Ala Leu Ile Asn Pro Tyr Lys Gly Val Ser Thr Tyr Asn Gln Lys Phe
    50                  55                  60

Lys Asp Arg Phe Thr Ile Ser Val Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Gly Tyr Tyr Gly Asp Ser Asp Trp Tyr Phe Asp Val Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Pro Val Ala
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Gln Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Trp Cys Leu Val Lys Gly Phe Tyr Pro Ser Asp Ile Ala Val Glu
```

-continued

```
                    370                 375                 380
Trp Glu Ser Asn Gly Gln Pro Glu Asn Tyr Lys Thr Thr Pro Pro
385                 390                 395                 400

Val Leu Asp Ser Asp Gly Ser Phe Phe Leu Tyr Ser Lys Leu Thr Val
                    405                 410                 415

Asp Lys Ser Arg Trp Gln Gln Gly Asn Val Phe Ser Cys Ser Val Met
                    420                 425                 430

His Glu Ala Leu His Asn His Tyr Thr Gln Lys Ser Leu Ser Leu Ser
                    435                 440                 445

Pro Gly Lys
450

<210> SEQ ID NO 35
<211> LENGTH: 698
<212> TYPE: PRT
<213> ORGANISM: Homo sapiens

<400> SEQUENCE: 35

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
                20                  25                  30

Thr Met Asn Trp Val Arg Gln Ala Pro Gly Lys Gly Leu Glu Trp Val
            35                  40                  45

Ala Leu Ile Asn Pro Tyr Lys Gly Val Ser Thr Tyr Asn Gln Lys Phe
        50                  55                  60

Lys Asp Arg Phe Thr Ile Ser Val Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Gly Tyr Tyr Gly Asp Ser Asp Trp Tyr Phe Asp Val Trp
                100                 105                 110

Gly Gln Gly Thr Leu Val Thr Val Ser Ser Ala Ser Thr Lys Gly Pro
            115                 120                 125

Ser Val Phe Pro Leu Ala Pro Ser Ser Lys Ser Thr Ser Gly Gly Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Ser Asp Lys Thr His Thr Cys Pro Pro Cys Pro Ala Pro Pro Val Ala
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285
```

```
His Asn Ala Lys Thr Lys Pro Arg Glu Glu Gln Tyr Gln Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Ser Cys Ala Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Val Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys Glu Ala Gly Val Thr Gln Ser Pro Thr His Leu Ile Lys
    450                 455                 460

Thr Arg Gly Gln Gln Val Thr Leu Arg Cys Ser Pro Lys Ser Gly His
465                 470                 475                 480

Asp Thr Val Ser Trp Tyr Gln Gln Ala Leu Gly Gln Gly Pro Gln Phe
                485                 490                 495

Ile Phe Gln Tyr Val Arg Gly Glu Glu Arg Gln Arg Gly Asn Phe Pro
            500                 505                 510

Asp Arg Phe Ser Gly His Gln Tyr Pro Asn Tyr Ser Ser Glu Leu Asn
        515                 520                 525

Ile Asn Ala Leu Leu Leu Gly Asp Ser Ala Leu Tyr Leu Cys Ala Ser
    530                 535                 540

Ser Asp Thr Val Ser Tyr Glu Gln Tyr Phe Gly Pro Gly Ile Arg Leu
545                 550                 555                 560

Thr Val Thr Glu Asp Leu Lys Asn Gly Ser Ala Asp Ala Lys Lys
                565                 570                 575

Asp Ala Ala Lys Lys Asp Gly Lys Ser Gln Lys Glu Val Glu Gln Asn
            580                 585                 590

Ser Gly Pro Leu Ser Val Pro Glu Gly Ala Ile Ala Ser Leu Asn Cys
        595                 600                 605

Thr Tyr Ser Asp Arg Gly Ser Gln Ser Phe Phe Trp Tyr Arg Gln Tyr
    610                 615                 620

Ser Gly Lys Ser Pro Glu Leu Ile Met Ser Ile Tyr Ser Asn Gly Asp
625                 630                 635                 640

Lys Glu Asp Gly Arg Phe Thr Ala Gln Leu Asn Lys Ala Ser Gln Tyr
                645                 650                 655

Ile Ser Leu Leu Ile Arg Asp Ser Lys Leu Ser Asp Ser Ala Thr Tyr
            660                 665                 670

Leu Cys Ala Val Arg Gly Ala His Asp Tyr Ala Leu Asn Phe Gly Lys
        675                 680                 685

Gly Thr Ser Leu Leu Val Thr Pro His Ile
690                 695
```

<210> SEQ ID NO 36
<211> LENGTH: 692
<212> TYPE: PRT
<213> ORGANISM: Homo sapiens

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Glu Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Glu Pro Lys Ser Ser Asp Lys Thr His Thr
210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Gln Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Trp Cys Leu Val Lys
        355                 360                 365

Gly Phe Tyr Pro Ser Asp Ile Ala Val Glu Trp Glu Ser Asn Gly Gln
370                 375                 380

```
Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
            405                 410                 415

Gln Gly Asn Val Phe Ser Cys Ser Val Met His Glu Ala Leu His Asn
        420                 425                 430

His Tyr Thr Gln Lys Ser Leu Ser Leu Ser Pro Gly Lys Glu Ala Gly
    435                 440                 445

Val Thr Gln Ser Pro Thr His Leu Ile Lys Thr Arg Gly Gln Gln Val
450                 455                 460

Thr Leu Arg Cys Ser Pro Lys Ser Gly His Asp Thr Val Ser Trp Tyr
465                 470                 475                 480

Gln Gln Ala Leu Gly Gln Gly Pro Gln Phe Ile Phe Gln Tyr Val Arg
            485                 490                 495

Gly Glu Glu Arg Gln Arg Gly Asn Phe Pro Asp Arg Phe Ser Gly His
            500                 505                 510

Gln Tyr Pro Asn Tyr Ser Ser Glu Leu Asn Ile Asn Ala Leu Leu Leu
        515                 520                 525

Gly Asp Ser Ala Leu Tyr Leu Cys Ala Ser Ser Asp Thr Val Ser Tyr
530                 535                 540

Glu Gln Tyr Phe Gly Pro Gly Ile Arg Leu Thr Val Thr Glu Asp Leu
545                 550                 555                 560

Lys Asn Gly Ser Ala Asp Ala Lys Lys Asp Ala Ala Lys Lys Asp
            565                 570                 575

Gly Lys Ser Gln Lys Glu Val Glu Gln Asn Ser Gly Pro Leu Ser Val
            580                 585                 590

Pro Glu Gly Ala Ile Ala Ser Leu Asn Cys Thr Tyr Ser Asp Arg Gly
            595                 600                 605

Ser Gln Ser Phe Phe Trp Tyr Arg Gln Tyr Ser Gly Lys Ser Pro Glu
            610                 615                 620

Leu Ile Met Ser Ile Tyr Ser Asn Gly Asp Lys Glu Asp Gly Arg Phe
625                 630                 635                 640

Thr Ala Gln Leu Asn Lys Ala Ser Gln Tyr Ile Ser Leu Leu Ile Arg
            645                 650                 655

Asp Ser Lys Leu Ser Asp Ser Ala Thr Tyr Leu Cys Ala Val Arg Gly
            660                 665                 670

Ala His Asp Tyr Ala Leu Asn Phe Gly Lys Gly Thr Ser Leu Leu Val
    675                 680                 685

Thr Pro His Ile
    690

<210> SEQ ID NO 37
<211> LENGTH: 698
<212> TYPE: PRT
<213> ORGANISM: Homo sapiens

<400> SEQUENCE: 37

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
            20                  25                  30

Thr Met Asn Trp Val Arg Gln Ala Pro Gly Lys Gly Leu Glu Trp Val
        35                  40                  45

Ala Leu Ile Asn Pro Tyr Lys Gly Val Ser Thr Tyr Asn Gln Lys Phe
50                  55                  60
```

```
Lys Asp Arg Phe Thr Ile Ser Val Asp Lys Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Ser Gly Tyr Tyr Gly Asp Ser Asp Trp Tyr Phe Asp Val Trp
            100                 105                 110

Gly Gln Gly Thr Leu Val Thr Val Ser Ser Ala Ser Thr Lys Gly Pro
            115                 120                 125

Ser Val Phe Pro Leu Ala Pro Ser Ser Lys Ser Thr Ser Gly Gly Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Ser Leu Gly Thr Gln Thr Tyr Ile Cys Asn Val Asn
                195                 200                 205

His Lys Pro Ser Asn Thr Lys Val Asp Lys Val Glu Pro Lys Ser
            210                 215                 220

Cys Asp Lys Thr His Thr Cys Pro Pro Cys Pro Ala Pro Val Ala
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Gln Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys Glu Ala Gly Val Thr Gln Ser Pro Thr His Leu Ile Lys
            450                 455                 460

Thr Arg Gly Gln Gln Val Thr Leu Arg Cys Ser Pro Lys Ser Gly His
465                 470                 475                 480
```

Asp Thr Val Ser Trp Tyr Gln Gln Ala Leu Gly Gln Gly Pro Gln Phe
            485                 490                 495

Ile Phe Gln Tyr Val Arg Gly Glu Glu Arg Gln Arg Gly Asn Phe Pro
        500                 505                 510

Asp Arg Phe Ser Gly His Gln Tyr Pro Asn Tyr Ser Ser Glu Leu Asn
    515                 520                 525

Ile Asn Ala Leu Leu Leu Gly Asp Ser Ala Leu Tyr Leu Cys Ala Ser
530                 535                 540

Ser Asp Thr Val Ser Tyr Glu Gln Tyr Phe Gly Pro Gly Ile Arg Leu
545                 550                 555                 560

Thr Val Thr Glu Asp Leu Lys Asn Gly Ser Ala Asp Ala Lys Lys
                565                 570                 575

Asp Ala Ala Lys Lys Asp Gly Lys Ser Gln Lys Glu Val Glu Gln Asn
                580                 585                 590

Ser Gly Pro Leu Ser Val Pro Glu Gly Ala Ile Ala Ser Leu Asn Cys
                595                 600                 605

Thr Tyr Ser Asp Arg Gly Ser Gln Ser Phe Phe Trp Tyr Arg Gln Tyr
            610                 615                 620

Ser Gly Lys Ser Pro Glu Leu Ile Met Ser Ile Tyr Ser Asn Gly Asp
625                 630                 635                 640

Lys Glu Asp Gly Arg Phe Thr Ala Gln Leu Asn Lys Ala Ser Gln Tyr
                645                 650                 655

Ile Ser Leu Leu Ile Arg Asp Ser Lys Leu Ser Asp Ser Ala Thr Tyr
                660                 665                 670

Leu Cys Ala Val Arg Gly Ala His Asp Tyr Ala Leu Asn Phe Gly Lys
            675                 680                 685

Gly Thr Ser Leu Leu Val Thr Pro His Ile
    690                 695

<210> SEQ ID NO 38
<211> LENGTH: 696
<212> TYPE: PRT
<213> ORGANISM: Homo sapiens

<400> SEQUENCE: 38

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
            20                  25                  30

Thr Met Asn Trp Val Arg Gln Ala Pro Gly Lys Gly Leu Glu Trp Val
        35                  40                  45

Ala Leu Ile Asn Pro Tyr Lys Gly Val Ser Thr Tyr Asn Gln Lys Phe
    50                  55                  60

Lys Asp Arg Phe Thr Ile Ser Val Asp Lys Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Gly Tyr Tyr Gly Asp Ser Asp Trp Tyr Phe Asp Val Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

-continued

Val Ser Trp Asn Ser Gly Ala Leu Thr Ser Val His Thr Phe Pro
                165                 170                 175

Ala Val Leu Gln Ser Ser Gly Leu Tyr Ser Leu Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Gln Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Ser
        355                 360                 365

Cys Ala Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys Glu Ala Gly Val Thr Gln Ser Pro Thr His Leu Ile Lys Thr Arg
450                 455                 460

Gly Gln Gln Val Thr Leu Arg Cys Ser Pro Lys Ser Gly His Asp Thr
465                 470                 475                 480

Val Ser Trp Tyr Gln Gln Ala Leu Gly Gln Gly Pro Gln Phe Ile Phe
                485                 490                 495

Gln Tyr Val Arg Gly Glu Glu Arg Gln Arg Gly Asn Phe Pro Asp Arg
            500                 505                 510

Phe Ser Gly His Gln Tyr Pro Asn Tyr Ser Ser Glu Leu Asn Ile Asn
        515                 520                 525

Ala Leu Leu Leu Gly Asp Ser Ala Leu Tyr Leu Cys Ala Ser Ser Asp
530                 535                 540

Thr Val Ser Tyr Glu Gln Tyr Phe Gly Pro Gly Ile Arg Leu Thr Val
545                 550                 555                 560

Thr Glu Asp Leu Lys Asn Gly Ser Ala Asp Asp Ala Lys Lys Asp Ala
                565                 570                 575

```
Ala Lys Lys Asp Gly Lys Ser Gln Lys Glu Val Glu Gln Asn Ser Gly
                580                 585                 590

Pro Leu Ser Val Pro Glu Gly Ala Ile Ala Ser Leu Asn Cys Thr Tyr
            595                 600                 605

Ser Asp Arg Gly Ser Gln Ser Phe Phe Trp Tyr Arg Gln Tyr Ser Gly
        610                 615                 620

Lys Ser Pro Glu Leu Ile Met Ser Ile Tyr Ser Asn Gly Asp Lys Glu
625                 630                 635                 640

Asp Gly Arg Phe Thr Ala Gln Leu Asn Lys Ala Ser Gln Tyr Ile Ser
                645                 650                 655

Leu Leu Ile Arg Asp Ser Lys Leu Ser Asp Ser Ala Thr Tyr Leu Cys
            660                 665                 670

Ala Val Arg Gly Ala His Asp Tyr Ala Leu Asn Phe Gly Lys Gly Thr
        675                 680                 685

Ser Leu Leu Val Thr Pro His Ile
    690                 695

<210> SEQ ID NO 39
<211> LENGTH: 690
<212> TYPE: PRT
<213> ORGANISM: Homo sapiens

<400> SEQUENCE: 39

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Glu Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Asn Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Glu Ser Lys Tyr Gly Pro Pro Cys Pro Pro
    210                 215                 220

Cys Pro Ala Pro Glu Phe Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255
```

```
Cys Val Val Asp Val Ser Gln Glu Asp Pro Glu Val Gln Phe Asn
        260                 265                 270

Trp Tyr Val Asp Gly Val Glu Val His Asn Ala Lys Thr Lys Pro Arg
            275                 280                 285

Glu Glu Gln Phe Gln Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Trp Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
                405                 410                 415

Asn Val Phe Ser Cys Ser Val Met His Glu Ala Leu His Asn His Tyr
            420                 425                 430

Thr Gln Lys Ser Leu Ser Leu Ser Leu Gly Lys Glu Ala Gly Val Thr
        435                 440                 445

Gln Ser Pro Thr His Leu Ile Lys Thr Arg Gly Gln Gln Val Thr Leu
    450                 455                 460

Arg Cys Ser Pro Lys Ser Gly His Asp Thr Val Ser Trp Tyr Gln Gln
465                 470                 475                 480

Ala Leu Gly Gln Gly Pro Gln Phe Ile Phe Gln Tyr Val Arg Gly Glu
                485                 490                 495

Glu Arg Gln Arg Gly Asn Phe Pro Asp Arg Phe Ser Gly His Gln Tyr
            500                 505                 510

Pro Asn Tyr Ser Ser Glu Leu Asn Ile Asn Ala Leu Leu Leu Gly Asp
        515                 520                 525

Ser Ala Leu Tyr Leu Cys Ala Ser Ser Asp Thr Val Ser Tyr Glu Gln
    530                 535                 540

Tyr Phe Gly Pro Gly Ile Arg Leu Thr Val Thr Glu Asp Leu Lys Asn
545                 550                 555                 560

Gly Ser Ala Asp Asp Ala Lys Lys Asp Ala Lys Lys Asp Gly Lys
                565                 570                 575

Ser Gln Lys Glu Val Glu Gln Asn Ser Gly Pro Leu Ser Val Pro Glu
            580                 585                 590

Gly Ala Ile Ala Ser Leu Asn Cys Thr Tyr Ser Asp Arg Gly Ser Gln
        595                 600                 605

Ser Phe Phe Trp Tyr Arg Gln Tyr Ser Gly Lys Ser Pro Glu Leu Ile
    610                 615                 620

Met Ser Ile Tyr Ser Asn Gly Asp Lys Glu Asp Gly Arg Phe Thr Ala
625                 630                 635                 640

Gln Leu Asn Lys Ala Ser Gln Tyr Ile Ser Leu Leu Ile Arg Asp Ser
                645                 650                 655

Lys Leu Ser Asp Ser Ala Thr Tyr Leu Cys Ala Val Arg Gly Ala His
            660                 665                 670
```

```
Asp Tyr Ala Leu Asn Phe Gly Lys Gly Thr Ser Leu Leu Val Thr Pro
            675                 680                 685

His Ile
    690

<210> SEQ ID NO 40
<211> LENGTH: 428
<212> TYPE: PRT
<213> ORGANISM: Homo sapiens

<400> SEQUENCE: 40

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Glu Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Asn Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Asp Ile Gln Met Thr Gln Ser Pro Ser Ser
210                 215                 220

Leu Ser Ala Ser Val Gly Asp Arg Val Thr Ile Thr Cys Arg Ala Ser
225                 230                 235                 240

Gln Asp Ile Arg Asn Tyr Leu Asn Trp Tyr Gln Gln Lys Pro Gly Lys
                245                 250                 255

Ala Pro Lys Leu Leu Ile Tyr Tyr Thr Ser Arg Leu Glu Ser Gly Val
            260                 265                 270

Pro Ser Arg Phe Ser Gly Ser Gly Ser Gly Thr Asp Tyr Thr Leu Thr
        275                 280                 285

Ile Ser Ser Leu Gln Pro Glu Asp Phe Ala Thr Tyr Tyr Cys Gln Gln
290                 295                 300

Gly Asn Thr Leu Pro Trp Thr Phe Gly Gln Gly Thr Lys Val Glu Ile
305                 310                 315                 320

Lys Arg Thr Val Ala Ala Pro Ser Val Phe Ile Phe Pro Pro Ser Asp
                325                 330                 335

Glu Gln Leu Lys Ser Gly Thr Ala Ser Val Val Cys Leu Leu Asn Asn
            340                 345                 350
```

Phe Tyr Pro Arg Glu Ala Lys Val Gln Trp Lys Val Asp Asn Ala Leu
                355                 360                 365

Gln Ser Gly Asn Ser Gln Glu Ser Val Thr Glu Gln Asp Ser Lys Asp
    370                 375                 380

Ser Thr Tyr Ser Leu Ser Asn Thr Leu Thr Leu Ser Lys Ala Asp Tyr
385                 390                 395                 400

Glu Lys His Lys Val Tyr Ala Cys Glu Val Thr His Gln Gly Leu Ser
                405                 410                 415

Ser Pro Val Thr Lys Ser Phe Asn Arg Gly Glu Cys
                420                 425

<210> SEQ ID NO 41
<211> LENGTH: 1392
<212> TYPE: PRT
<213> ORGANISM: Homo sapiens

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
                20                  25                  30

Thr Met Asn Trp Val Arg Gln Ala Pro Gly Lys Gly Leu Glu Trp Val
            35                  40                  45

Ala Leu Ile Asn Pro Tyr Lys Gly Val Ser Thr Tyr Asn Gln Lys Phe
        50                  55                  60

Lys Asp Arg Phe Thr Ile Ser Val Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Gly Tyr Tyr Gly Asp Ser Asp Trp Tyr Phe Asp Val Trp
                100                 105                 110

Gly Gln Gly Thr Leu Val Thr Val Ser Ser Ala Ser Thr Lys Gly Pro
            115                 120                 125

Ser Val Phe Pro Leu Ala Pro Cys Ser Arg Ser Thr Ser Glu Ser Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Gln Ser Thr Tyr Arg Val

```
            290                 295                 300
Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Gln Glu Glu Met Thr Lys Asn Gln Val Ser Leu Thr
                355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
                420                 425                 430

Ala Leu His Asn His Tyr Thr Gln Lys Ser Leu Ser Leu Ser Leu Gly
                435                 440                 445

Lys Glu Ala Gly Val Thr Gln Ser Pro Thr His Leu Ile Lys Thr Arg
450                 455                 460

Gly Gln Gln Val Thr Leu Arg Cys Ser Pro Lys Ser Gly His Asp Thr
465                 470                 475                 480

Val Ser Trp Tyr Gln Gln Ala Leu Gly Gln Gly Pro Gln Phe Ile Phe
                485                 490                 495

Gln Tyr Val Arg Gly Glu Glu Arg Gln Arg Gly Asn Phe Pro Asp Arg
                500                 505                 510

Phe Ser Gly His Gln Tyr Pro Asn Tyr Ser Ser Glu Leu Asn Ile Asn
                515                 520                 525

Ala Leu Leu Leu Gly Asp Ser Ala Leu Tyr Leu Cys Ala Ser Ser Asp
                530                 535                 540

Thr Val Ser Tyr Glu Gln Tyr Phe Gly Pro Gly Ile Arg Leu Thr Val
545                 550                 555                 560

Thr Glu Asp Leu Lys Asn Gly Ser Ala Asp Ala Lys Lys Asp Ala
                565                 570                 575

Ala Lys Lys Asp Gly Lys Ser Gln Lys Glu Val Glu Gln Asn Ser Gly
                580                 585                 590

Pro Leu Ser Val Pro Glu Gly Ala Ile Ala Ser Leu Asn Cys Thr Tyr
                595                 600                 605

Ser Asp Arg Gly Ser Gln Ser Phe Phe Trp Tyr Arg Gln Tyr Ser Gly
                610                 615                 620

Lys Ser Pro Glu Leu Ile Met Ser Ile Tyr Ser Asn Gly Asp Lys Glu
625                 630                 635                 640

Asp Gly Arg Phe Thr Ala Gln Leu Asn Lys Ala Ser Gln Tyr Ile Ser
                645                 650                 655

Leu Leu Ile Arg Asp Ser Lys Leu Ser Asp Ser Ala Thr Tyr Leu Cys
                660                 665                 670

Ala Val Arg Gly Ala His Asp Tyr Ala Leu Asn Phe Gly Lys Gly Thr
                675                 680                 685

Ser Leu Leu Val Thr Pro His Ile Glu Val Gln Leu Val Glu Ser Gly
                690                 695                 700

Gly Gly Leu Val Gln Pro Gly Gly Ser Leu Arg Leu Ser Cys Ala Ala
705                 710                 715                 720
```

-continued

Ser Gly Tyr Ser Phe Thr Gly Tyr Thr Met Asn Trp Val Arg Gln Ala
                725                 730                 735
Pro Gly Lys Gly Leu Glu Trp Val Ala Leu Ile Asn Pro Tyr Lys Gly
            740                 745                 750
Val Ser Thr Tyr Asn Gln Lys Phe Lys Asp Arg Phe Thr Ile Ser Val
        755                 760                 765
Asp Lys Ser Lys Asn Thr Ala Tyr Leu Gln Met Asn Ser Leu Arg Ala
770                 775                 780
Glu Asp Thr Ala Val Tyr Tyr Cys Ala Arg Ser Gly Tyr Tyr Gly Asp
785                 790                 795                 800
Ser Asp Trp Tyr Phe Asp Val Trp Gly Gln Gly Thr Leu Val Thr Val
                805                 810                 815
Ser Ser Ala Ser Thr Lys Gly Pro Ser Val Phe Pro Leu Ala Pro Cys
            820                 825                 830
Ser Arg Ser Thr Ser Glu Ser Thr Ala Ala Leu Gly Cys Leu Val Lys
        835                 840                 845
Asp Tyr Phe Pro Glu Pro Val Thr Val Ser Trp Asn Ser Gly Ala Leu
850                 855                 860
Thr Ser Gly Val His Thr Phe Pro Ala Val Leu Gln Ser Ser Gly Leu
865                 870                 875                 880
Tyr Ser Leu Ser Ser Val Val Thr Val Pro Ser Ser Ser Leu Gly Thr
                885                 890                 895
Lys Thr Tyr Thr Cys Asn Val Asp His Lys Pro Ser Asn Thr Lys Val
            900                 905                 910
Asp Lys Arg Val Glu Ser Lys Tyr Gly Pro Pro Cys Pro Pro Cys Pro
        915                 920                 925
Ala Pro Glu Phe Leu Gly Gly Pro Ser Val Phe Leu Phe Pro Pro Lys
930                 935                 940
Pro Lys Asp Thr Leu Met Ile Ser Arg Thr Pro Glu Val Thr Cys Val
945                 950                 955                 960
Val Val Asp Val Ser Gln Glu Asp Pro Glu Val Gln Phe Asn Trp Tyr
                965                 970                 975
Val Asp Gly Val Glu Val His Asn Ala Lys Thr Lys Pro Arg Glu Glu
            980                 985                 990
Gln Phe Gln Ser Thr Tyr Arg Val Val Ser Val Leu Thr Val Leu His
        995                 1000                1005
Gln Asp Trp Leu Asn Gly Lys Glu Tyr Lys Cys Lys Val Ser Asn
    1010                1015                1020
Lys Gly Leu Pro Ser Ser Ile Glu Lys Thr Ile Ser Lys Ala Lys
    1025                1030                1035
Gly Gln Pro Arg Glu Pro Gln Val Tyr Thr Leu Pro Pro Ser Gln
    1040                1045                1050
Glu Glu Met Thr Lys Asn Gln Val Ser Leu Thr Cys Leu Val Lys
    1055                1060                1065
Gly Phe Tyr Pro Ser Asp Ile Ala Val Glu Trp Glu Ser Asn Gly
    1070                1075                1080
Gln Pro Glu Asn Asn Tyr Lys Thr Thr Pro Pro Val Leu Asp Ser
    1085                1090                1095
Asp Gly Ser Phe Phe Leu Tyr Ser Arg Leu Thr Val Asp Lys Ser
    1100                1105                1110
Arg Trp Gln Glu Gly Asn Val Phe Ser Cys Ser Val Met His Glu
    1115                1120                1125

```
Ala Leu His Asn His Tyr Thr Gln Lys Ser Leu Ser Leu Ser Leu
    1130                1135                1140

Gly Lys Glu Ala Gly Val Thr Gln Ser Pro Thr His Leu Ile Lys
    1145                1150                1155

Thr Arg Gly Gln Gln Val Thr Leu Arg Cys Ser Pro Lys Ser Gly
    1160                1165                1170

His Asp Thr Val Ser Trp Tyr Gln Gln Ala Leu Gly Gln Gly Pro
    1175                1180                1185

Gln Phe Ile Phe Gln Tyr Val Arg Gly Glu Glu Arg Gln Arg Gly
    1190                1195                1200

Asn Phe Pro Asp Arg Phe Ser Gly His Gln Tyr Pro Asn Tyr Ser
    1205                1210                1215

Ser Glu Leu Asn Ile Asn Ala Leu Leu Leu Gly Asp Ser Ala Leu
    1220                1225                1230

Tyr Leu Cys Ala Ser Ser Asp Thr Val Ser Tyr Glu Gln Tyr Phe
    1235                1240                1245

Gly Pro Gly Ile Arg Leu Thr Val Thr Glu Asp Leu Lys Asn Gly
    1250                1255                1260

Ser Ala Asp Asp Ala Lys Lys Asp Ala Ala Lys Lys Asp Gly Lys
    1265                1270                1275

Ser Gln Lys Glu Val Glu Gln Asn Ser Gly Pro Leu Ser Val Pro
    1280                1285                1290

Glu Gly Ala Ile Ala Ser Leu Asn Cys Thr Tyr Ser Asp Arg Gly
    1295                1300                1305

Ser Gln Ser Phe Phe Trp Tyr Arg Gln Tyr Ser Gly Lys Ser Pro
    1310                1315                1320

Glu Leu Ile Met Ser Ile Tyr Ser Asn Gly Asp Lys Glu Asp Gly
    1325                1330                1335

Arg Phe Thr Ala Gln Leu Asn Lys Ala Ser Gln Tyr Ile Ser Leu
    1340                1345                1350

Leu Ile Arg Asp Ser Lys Leu Ser Asp Ser Ala Thr Tyr Leu Cys
    1355                1360                1365

Ala Val Arg Gly Ala His Asp Tyr Ala Leu Asn Phe Gly Lys Gly
    1370                1375                1380

Thr Ser Leu Leu Val Thr Pro His Ile
    1385                1390

<210> SEQ ID NO 42
<211> LENGTH: 214
<212> TYPE: PRT
<213> ORGANISM: Homo sapiens

<400> SEQUENCE: 42

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Glu Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95
```

```
Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 43
<211> LENGTH: 461
<212> TYPE: PRT
<213> ORGANISM: Homo sapiens

<400> SEQUENCE: 43

Gln Lys Glu Val Glu Gln Asn Ser Gly Pro Leu Ser Val Pro Glu Gly
1               5                   10                  15

Ala Ile Ala Ser Leu Asn Cys Thr Tyr Ser Asp Arg Gly Ser Gln Ser
            20                  25                  30

Phe Phe Trp Tyr Arg Gln Tyr Ser Gly Lys Ser Pro Glu Leu Ile Met
        35                  40                  45

Ser Ile Tyr Ser Asn Gly Asp Lys Glu Asp Gly Arg Phe Thr Ala Gln
    50                  55                  60

Leu Asn Lys Ala Ser Gln Tyr Phe Ser Leu Leu Ile Arg Asp Ser Gln
65                  70                  75                  80

Pro Ser Asp Ser Ala Thr Tyr Leu Cys Ala Ala Val Ile Asp Asn Ser
                85                  90                  95

Asn Gly Gly Ile Leu Thr Phe Gly Thr Gly Thr Arg Leu Thr Ile Ile
            100                 105                 110

Pro Asn Ile Gln Asn Gly Gly Ser Gly Gly Gly Asp Ile Gln
        115                 120                 125

Met Thr Gln Ser Pro Ser Ser Leu Ser Ala Ser Val Gly Asp Arg Val
130                 135                 140

Thr Ile Thr Cys Arg Ala Ser Gln Asp Ile Arg Asn Tyr Leu Asn Trp
145                 150                 155                 160

Tyr Gln Gln Lys Pro Gly Lys Ala Pro Lys Leu Leu Ile Tyr Tyr Thr
                165                 170                 175

Ser Arg Leu His Ser Gly Val Pro Ser Arg Phe Ser Gly Ser Gly Ser
            180                 185                 190

Gly Thr Asp Tyr Thr Leu Thr Ile Ser Ser Leu Gln Pro Glu Asp Ile
        195                 200                 205

Ala Thr Tyr Phe Cys Gln Gln Gly Gln Thr Leu Pro Trp Thr Phe Gly
    210                 215                 220

Gln Gly Thr Lys Val Glu Ile Lys Glu Pro Lys Ser Ser Asp Lys Thr
225                 230                 235                 240

His Thr Cys Pro Pro Cys Pro Ala Pro Pro Val Ala Gly Pro Ser Val
```

-continued

```
                    245                 250                 255
Phe Leu Phe Pro Pro Lys Pro Lys Asp Thr Leu Met Ile Ser Arg Thr
            260                 265                 270

Pro Glu Val Thr Cys Val Val Asp Val Ser His Glu Asp Pro Glu
        275                 280                 285

Val Lys Phe Asn Trp Tyr Val Asp Gly Val Glu Val His Asn Ala Lys
        290                 295                 300

Thr Lys Pro Arg Glu Glu Gln Tyr Gln Ser Thr Tyr Arg Val Val Ser
305                 310                 315                 320

Val Leu Thr Val Leu His Gln Asp Trp Leu Asn Gly Lys Glu Tyr Lys
                325                 330                 335

Cys Lys Val Ser Asn Lys Ala Leu Pro Ala Ser Ile Glu Lys Thr Ile
                340                 345                 350

Ser Lys Ala Lys Gly Gln Pro Arg Glu Pro Gln Val Tyr Thr Leu Pro
                355                 360                 365

Pro Cys Arg Asp Glu Leu Thr Lys Asn Gln Val Ser Leu Trp Cys Leu
        370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415

Asp Gly Ser Phe Phe Leu Tyr Ser Lys Leu Thr Val Asp Lys Ser Arg
            420                 425                 430

Trp Gln Gln Gly Asn Val Phe Ser Cys Ser Val Met His Glu Ala Leu
        435                 440                 445

His Asn His Tyr Thr Gln Lys Ser Leu Ser Leu Ser Pro
        450                 455                 460
```

<210> SEQ ID NO 44
<211> LENGTH: 477
<212> TYPE: PRT
<213> ORGANISM: Homo sapiens

<400> SEQUENCE: 44

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Thr Met Asn Trp Val Arg Gln Ala Pro Gly Gln Gly Leu Glu Trp Met
        35                  40                  45

Gly Leu Ile Asn Pro Tyr Lys Gly Val Ser Thr Tyr Ala Gln Lys Phe
    50                  55                  60

Gln Asp Arg Val Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Tyr Tyr Gly Asp Ser Asp Trp Tyr Phe Asp Val Trp
            100                 105                 110

Gly Gln Gly Thr Leu Val Thr Val Ser Ser Gly Gly Ser Gly Gly
        115                 120                 125

Gly Gly Lys Ala Gly Val Thr Gln Thr Pro Arg Tyr Leu Ile Lys Thr
    130                 135                 140

Arg Gly Gln Gln Val Thr Leu Ser Cys Ser Pro Ile Pro Gly His Arg
145                 150                 155                 160
```

```
Ser Val Ser Trp Tyr Gln Gln Thr Pro Gly Gln Gly Leu Gln Phe Leu
            165                 170                 175

Phe Glu Tyr Val His Gly Ala Glu Arg Asn Lys Gly Asn Phe Pro Gly
        180                 185                 190

Arg Phe Ser Gly Arg Gln Phe Ser Asn Ser Ser Glu Met Asn Ile
        195                 200                 205

Ser Asn Leu Glu Leu Gly Asp Ser Ala Leu Tyr Leu Cys Ala Ser Ser
    210                 215                 220

Pro Trp Asp Ser Pro Asn Glu Gln Tyr Phe Gly Pro Gly Thr Arg Leu
225                 230                 235                 240

Thr Val Thr Glu Asp Leu Lys Asn Glu Pro Lys Ser Ser Asp Lys Thr
                245                 250                 255

His Thr Cys Pro Pro Cys Pro Ala Pro Pro Val Ala Gly Pro Ser Val
            260                 265                 270

Phe Leu Phe Pro Pro Lys Pro Lys Asp Thr Leu Met Ile Ser Arg Thr
        275                 280                 285

Pro Glu Val Thr Cys Val Val Asp Val Ser His Glu Asp Pro Glu
    290                 295                 300

Val Lys Phe Asn Trp Tyr Val Asp Gly Val Glu Val His Asn Ala Lys
305                 310                 315                 320

Thr Lys Pro Arg Glu Glu Gln Tyr Gln Ser Thr Tyr Arg Val Val Ser
                325                 330                 335

Val Leu Thr Val Leu His Gln Asp Trp Leu Asn Gly Lys Glu Tyr Lys
            340                 345                 350

Cys Lys Val Ser Asn Lys Ala Leu Pro Ala Ser Ile Glu Lys Thr Ile
        355                 360                 365

Ser Lys Ala Lys Gly Gln Pro Arg Glu Pro Gln Val Cys Thr Leu Pro
    370                 375                 380

Pro Ser Arg Asp Glu Leu Thr Lys Asn Gln Val Ser Leu Ser Cys Ala
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
            420                 425                 430

Asp Gly Ser Phe Phe Leu Val Ser Lys Leu Thr Val Asp Lys Ser Arg
        435                 440                 445

Trp Gln Gln Gly Asn Val Phe Ser Cys Ser Val Met His Glu Ala Leu
    450                 455                 460

His Asn His Tyr Thr Gln Lys Ser Leu Ser Leu Ser Pro
465                 470                 475

<210> SEQ ID NO 45
<211> LENGTH: 463
<212> TYPE: PRT
<213> ORGANISM: Homo sapiens

<400> SEQUENCE: 45

Gln Lys Glu Val Glu Gln Asn Ser Gly Pro Leu Ser Val Pro Glu Gly
1               5                   10                  15

Ala Ile Ala Ser Leu Asn Cys Thr Tyr Ser Asp Arg Gly Ser Gln Ser
            20                  25                  30

Phe Phe Trp Tyr Arg Gln Tyr Ser Gly Lys Ser Pro Glu Leu Ile Met
        35                  40                  45

Ser Ile Tyr Ser Asn Gly Asp Lys Glu Asp Gly Arg Phe Thr Ala Gln
    50                  55                  60
```

Leu Asn Lys Ala Ser Gln Tyr Val Ser Leu Ile Arg Asp Ser Gln
65                  70                  75                  80

Pro Ser Asp Ser Ala Thr Tyr Leu Cys Ala Ala Val Ile Asp Asn Asp
                85                  90                  95

Gln Gly Gly Ile Leu Thr Phe Gly Thr Gly Thr Arg Leu Thr Ile Ile
            100                 105                 110

Pro Asn Ile Gln Asn Gly Gly Ser Gly Gly Gly Gly Asp Ile Gln
        115                 120                 125

Met Thr Gln Ser Pro Ser Ser Leu Ser Ala Ser Val Gly Asp Arg Val
130                 135                 140

Thr Ile Thr Cys Arg Ala Ser Gln Asp Ile Arg Asn Tyr Leu Asn Trp
145                 150                 155                 160

Tyr Gln Gln Lys Pro Gly Lys Ala Pro Lys Leu Leu Ile Tyr Tyr Thr
                165                 170                 175

Ser Arg Leu His Ser Gly Val Pro Ser Arg Phe Ser Gly Ser Gly Ser
            180                 185                 190

Gly Thr Asp Tyr Thr Leu Thr Ile Ser Ser Leu Gln Pro Glu Asp Ile
        195                 200                 205

Ala Thr Tyr Phe Cys Gln Gln Gly Gln Thr Leu Pro Trp Thr Phe Gly
210                 215                 220

Gln Gly Thr Lys Val Glu Ile Lys Glu Pro Lys Ser Ser Asp Lys Thr
225                 230                 235                 240

His Thr Cys Pro Pro Cys Pro Ala Pro Pro Val Ala Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
        275                 280                 285

Val Lys Phe Asn Trp Tyr Val Asp Gly Val Glu Val His Asn Ala Lys
290                 295                 300

Thr Lys Pro Arg Glu Glu Gln Tyr Gln Ser Thr Tyr Arg Val Val Ser
305                 310                 315                 320

Val Leu Thr Val Leu His Gln Asp Trp Leu Asn Gly Lys Glu Tyr Lys
                325                 330                 335

Cys Lys Val Ser Asn Lys Ala Leu Pro Ala Ser Ile Glu Lys Thr Ile
            340                 345                 350

Ser Lys Ala Lys Gly Gln Pro Arg Glu Pro Gln Val Tyr Thr Leu Pro
        355                 360                 365

Pro Cys Arg Asp Glu Leu Thr Lys Asn Gln Val Ser Leu Trp Cys Leu
370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415

Asp Gly Ser Phe Phe Leu Tyr Ser Lys Leu Thr Val Asp Lys Ser Arg
            420                 425                 430

Trp Gln Gln Gly Asn Val Phe Ser Cys Ser Val Met His Glu Ala Leu
        435                 440                 445

His Asn His Tyr Thr Gln Lys Ser Leu Ser Leu Ser Pro Gly Lys
450                 455                 460

<210> SEQ ID NO 46
<211> LENGTH: 479

<212> TYPE: PRT
<213> ORGANISM: Homo sapiens

<400> SEQUENCE: 46

| | | | | | | | | | | | | | | | |
|---|---|---|---|---|---|---|---|---|---|---|---|---|---|---|---|
| Glu | Val | Gln | Leu | Val | Gln | Ser | Gly | Ala | Glu | Val | Lys | Lys | Pro | Gly | Ala |
| 1 | | | | 5 | | | | | 10 | | | | | 15 | |
| Ser | Val | Lys | Val | Ser | Cys | Lys | Ala | Ser | Gly | Tyr | Ser | Phe | Thr | Gly | Tyr |
| | | | 20 | | | | | 25 | | | | | 30 | | |
| Thr | Met | Asn | Trp | Val | Arg | Gln | Ala | Pro | Gly | Gln | Gly | Leu | Glu | Trp | Met |
| | | 35 | | | | | 40 | | | | | 45 | | | |
| Gly | Leu | Ile | Asn | Pro | Tyr | Lys | Gly | Val | Ser | Thr | Tyr | Ala | Gln | Lys | Phe |
| | 50 | | | | | 55 | | | | | 60 | | | | |
| Gln | Asp | Arg | Val | Thr | Leu | Thr | Val | Asp | Lys | Ser | Thr | Ser | Thr | Ala | Tyr |
| 65 | | | | | 70 | | | | | 75 | | | | | 80 |
| Met | Glu | Leu | Ser | Ser | Leu | Arg | Ser | Glu | Asp | Thr | Ala | Val | Tyr | Tyr | Cys |
| | | | | 85 | | | | | 90 | | | | | 95 | |
| Ala | Arg | Ser | Gly | Tyr | Tyr | Gly | Asp | Ser | Asp | Trp | Tyr | Phe | Asp | Val | Trp |
| | | | 100 | | | | | 105 | | | | | 110 | | |
| Gly | Gln | Gly | Thr | Leu | Val | Thr | Val | Ser | Ser | Gly | Gly | Ser | Gly | Gly | |
| | | 115 | | | | | 120 | | | | | 125 | | | |
| Gly | Gly | Lys | Ala | Gly | Val | Thr | Gln | Thr | Pro | Arg | Tyr | Leu | Ile | Lys | Thr |
| | 130 | | | | | 135 | | | | | 140 | | | | |
| Arg | Gly | Gln | Gln | Val | Thr | Leu | Ser | Cys | Ser | Pro | Ile | Pro | Gly | His | Arg |
| 145 | | | | | 150 | | | | | 155 | | | | | 160 |
| Ala | Val | Ser | Trp | Tyr | Gln | Gln | Thr | Pro | Gly | Gln | Gly | Leu | Gln | Phe | Leu |
| | | | | 165 | | | | | 170 | | | | | 175 | |
| Phe | Glu | Tyr | Val | His | Gly | Glu | Glu | Arg | Asn | Lys | Gly | Asn | Phe | Pro | Gly |
| | | | 180 | | | | | 185 | | | | | 190 | | |
| Arg | Phe | Ser | Gly | Arg | Gln | Phe | Ser | Asn | Ser | Ser | Glu | Met | Asn | Ile | |
| | | | 195 | | | | | 200 | | | | | 205 | | |
| Ser | Asn | Leu | Glu | Leu | Gly | Asp | Ser | Ala | Leu | Tyr | Leu | Cys | Ala | Ser | Ser |
| | | 210 | | | | | 215 | | | | | 220 | | | |
| Pro | Trp | Asp | Ser | Pro | Asn | Val | Gln | Tyr | Phe | Gly | Pro | Gly | Thr | Arg | Leu |
| 225 | | | | | 230 | | | | | 235 | | | | | 240 |
| Thr | Val | Thr | Glu | Asp | Leu | Lys | Asn | Glu | Pro | Lys | Ser | Ser | Asp | Lys | Thr |
| | | | | 245 | | | | | 250 | | | | | 255 | |
| His | Thr | Cys | Pro | Pro | Cys | Pro | Ala | Pro | Pro | Val | Ala | Gly | Pro | Ser | Val |
| | | | 260 | | | | | 265 | | | | | 270 | | |
| Phe | Leu | Phe | Pro | Pro | Lys | Pro | Lys | Asp | Thr | Leu | Met | Ile | Ser | Arg | Thr |
| | | 275 | | | | | 280 | | | | | 285 | | | |
| Pro | Glu | Val | Thr | Cys | Val | Val | Val | Asp | Val | Ser | His | Glu | Asp | Pro | Glu |
| | 290 | | | | | 295 | | | | | 300 | | | | |
| Val | Lys | Phe | Asn | Trp | Tyr | Val | Asp | Gly | Val | Glu | Val | His | Asn | Ala | Lys |
| 305 | | | | | 310 | | | | | 315 | | | | | 320 |
| Thr | Lys | Pro | Arg | Glu | Glu | Gln | Tyr | Gln | Ser | Thr | Tyr | Arg | Val | Val | Ser |
| | | | | 325 | | | | | 330 | | | | | 335 | |
| Val | Leu | Thr | Val | Leu | His | Gln | Asp | Trp | Leu | Asn | Gly | Lys | Glu | Tyr | Lys |
| | | | 340 | | | | | 345 | | | | | 350 | | |
| Cys | Lys | Val | Ser | Asn | Lys | Ala | Leu | Pro | Ala | Ser | Ile | Glu | Lys | Thr | Ile |
| | | 355 | | | | | 360 | | | | | 365 | | | |
| Ser | Lys | Ala | Lys | Gly | Gln | Pro | Arg | Glu | Pro | Val | Cys | Thr | Leu | Pro | |
| 370 | | | | | 375 | | | | | 380 | | | | | |
| Pro | Ser | Arg | Asp | Glu | Leu | Thr | Lys | Asn | Gln | Val | Ser | Leu | Ser | Cys | Ala |
| 385 | | | | | 390 | | | | | 395 | | | | | 400 |

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
            420                 425                 430

Asp Gly Ser Phe Phe Leu Val Ser Lys Leu Thr Val Asp Lys Ser Arg
            435                 440                 445

Trp Gln Gln Gly Asn Val Phe Ser Cys Ser Val Met His Glu Ala Leu
    450                 455                 460

His Asn His Tyr Thr Gln Lys Ser Leu Ser Leu Ser Pro Gly Lys
465                 470                 475

<210> SEQ ID NO 47
<211> LENGTH: 229
<212> TYPE: PRT
<213> ORGANISM: Homo sapiens

<400> SEQUENCE: 47

Glu Pro Lys Ser Ser Asp Lys Thr His Thr Cys Pro Pro Cys Pro Ala
1               5                   10                  15

Pro Pro Val Ala Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Ser His Glu Asp Pro Glu Val Lys Phe Asn Trp Tyr Val Asp
    50                  55                  60

Gly Val Glu Val His Asn Ala Lys Thr Lys Pro Arg Glu Glu Gln Tyr
65                  70                  75                  80

Gln Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Ser Ile Glu Lys Thr Ile Ser Lys Ala Lys Gly Gln Pro Arg
        115                 120                 125

Glu Pro Gln Val Cys Thr Leu Pro Pro Ser Arg Asp Glu Leu Thr Lys
    130                 135                 140

Asn Gln Val Ser Leu Ser Cys Ala Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Val Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro
225

<210> SEQ ID NO 48
<211> LENGTH: 229
<212> TYPE: PRT
<213> ORGANISM: Homo sapiens

<400> SEQUENCE: 48

Glu Pro Lys Ser Ser Asp Lys Thr His Thr Cys Pro Pro Cys Pro Ala
1               5                   10                  15

-continued

Pro Pro Val Ala Gly Pro Ser Val Phe Leu Phe Pro Pro Lys Pro Lys
                20                  25                  30

Asp Thr Leu Met Ile Ser Arg Thr Pro Glu Val Thr Cys Val Val Val
            35                  40                  45

Asp Val Ser His Glu Asp Pro Glu Val Lys Phe Asn Trp Tyr Val Asp
50                  55                  60

Gly Val Glu Val His Asn Ala Lys Thr Lys Pro Arg Glu Glu Gln Tyr
65                  70                  75                  80

Gln Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Ser Ile Glu Lys Thr Ile Ser Lys Ala Lys Gly Gln Pro Arg
        115                 120                 125

Glu Pro Gln Val Tyr Thr Leu Pro Pro Cys Arg Asp Glu Leu Thr Lys
    130                 135                 140

Asn Gln Val Ser Leu Trp Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro
225

<210> SEQ ID NO 49
<211> LENGTH: 9
<212> TYPE: PRT
<213> ORGANISM: Homo sapiens

<400> SEQUENCE: 49

Ser Leu Leu Gln His Leu Ile Gly Leu
1               5

<210> SEQ ID NO 50
<211> LENGTH: 6
<212> TYPE: PRT
<213> ORGANISM: Homo sapiens

<400> SEQUENCE: 50

Glu Leu Leu Gly Gly Pro
1               5

<210> SEQ ID NO 51
<211> LENGTH: 457
<212> TYPE: PRT
<213> ORGANISM: Homo sapiens

<400> SEQUENCE: 51

Gln Lys Glu Val Glu Gln Asn Ser Gly Pro Leu Ser Val Pro Glu Gly
1               5                   10                  15

Ala Ile Ala Ser Leu Asn Cys Thr Tyr Ser Asp Arg Gly Ser Gln Ser
            20                  25                  30

-continued

```
Phe Phe Trp Tyr Arg Gln Tyr Ser Gly Lys Ser Pro Glu Leu Ile Met
             35                  40                  45

Ser Ile Tyr Ser Asn Gly Asp Lys Glu Asp Gly Arg Phe Thr Ala Gln
 50                  55                  60

Leu Asn Lys Ala Ser Gln Tyr Ile Ser Leu Leu Ile Arg Asp Ser Lys
 65                  70                  75                  80

Leu Ser Asp Ser Ala Thr Tyr Leu Cys Ala Val Arg Gly Ala His Asp
                 85                  90                  95

Tyr Ala Leu Asn Phe Gly Lys Gly Thr Ser Leu Leu Val Thr Pro His
            100                 105                 110

Ile Gly Gly Gly Ser Gly Gly Gly Asp Ile Gln Met Thr Gln Ser
            115                 120                 125

Pro Ser Ser Leu Ser Ala Ser Val Gly Asp Arg Val Thr Ile Thr Cys
    130                 135                 140

Arg Ala Ser Gln Asp Ile Arg Asn Tyr Leu Asn Trp Tyr Gln Gln Lys
145                 150                 155                 160

Pro Gly Lys Ala Pro Lys Leu Leu Ile Tyr Tyr Thr Ser Arg Leu His
                165                 170                 175

Ser Gly Val Pro Ser Arg Phe Ser Gly Ser Gly Ser Gly Thr Asp Tyr
            180                 185                 190

Thr Leu Thr Ile Ser Ser Leu Gln Pro Glu Asp Ile Ala Thr Tyr Phe
        195                 200                 205

Cys Gln Gln Gly Gln Thr Leu Pro Trp Thr Phe Gly Gln Gly Thr Lys
    210                 215                 220

Val Glu Ile Lys Glu Pro Lys Ser Ser Asp Lys Thr His Thr Cys Pro
225                 230                 235                 240

Pro Cys Pro Ala Pro Pro Val Ala Gly Pro Ser Val Phe Leu Phe Pro
                245                 250                 255

Pro Lys Pro Lys Asp Thr Leu Met Ile Ser Arg Thr Pro Glu Val Thr
            260                 265                 270

Cys Val Val Val Asp Val Ser His Glu Asp Pro Glu Val Lys Phe Asn
        275                 280                 285

Trp Tyr Val Asp Gly Val Glu Val His Asn Ala Lys Thr Lys Pro Arg
    290                 295                 300

Glu Glu Gln Tyr Gln Ser Thr Tyr Arg Val Val Ser Val Leu Thr Val
305                 310                 315                 320

Leu His Gln Asp Trp Leu Asn Gly Lys Glu Tyr Lys Cys Lys Val Ser
                325                 330                 335

Asn Lys Ala Leu Pro Ala Ser Ile Glu Lys Thr Ile Ser Lys Ala Lys
            340                 345                 350

Gly Gln Pro Arg Glu Pro Gln Val Tyr Thr Leu Pro Pro Cys Arg Asp
        355                 360                 365

Glu Leu Thr Lys Asn Gln Val Ser Leu Trp Cys Leu Val Lys Gly Phe
    370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
                405                 410                 415

Phe Leu Tyr Ser Lys Leu Thr Val Asp Lys Ser Arg Trp Gln Gln Gly
            420                 425                 430

Asn Val Phe Ser Cys Ser Val Met His Glu Ala Leu His Asn His Tyr
        435                 440                 445

Thr Gln Lys Ser Leu Ser Leu Ser Pro
```

-continued

```
          450                 455
```

<210> SEQ ID NO 52
<211> LENGTH: 476
<212> TYPE: PRT
<213> ORGANISM: Homo sapiens

<400> SEQUENCE: 52

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Thr Met Asn Trp Val Arg Gln Ala Pro Gly Gln Gly Leu Glu Trp Met
        35                  40                  45

Gly Leu Ile Asn Pro Tyr Lys Gly Val Ser Thr Tyr Ala Gln Lys Phe
    50                  55                  60

Gln Asp Arg Val Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Tyr Tyr Gly Asp Ser Asp Trp Tyr Phe Asp Val Trp
            100                 105                 110

Gly Gln Gly Thr Leu Val Thr Val Ser Ser Gly Gly Gly Ser Gly Gly
        115                 120                 125

Gly Gly Glu Ala Gly Val Thr Gln Ser Pro Thr His Leu Ile Lys Thr
    130                 135                 140

Arg Gly Gln Gln Val Thr Leu Arg Cys Ser Pro Lys Ser Gly His Asp
145                 150                 155                 160

Thr Val Ser Trp Tyr Gln Gln Ala Leu Gly Gln Gly Pro Gln Phe Ile
                165                 170                 175

Phe Gln Tyr Val Arg Gly Glu Arg Gln Arg Gly Asn Phe Pro Asp
            180                 185                 190

Arg Phe Ser Gly His Gln Tyr Pro Asn Tyr Ser Ser Glu Leu Asn Ile
        195                 200                 205

Asn Ala Leu Leu Leu Gly Asp Ser Ala Leu Tyr Leu Cys Ala Ser Ser
    210                 215                 220

Asp Thr Val Ser Tyr Glu Gln Tyr Phe Gly Pro Gly Ile Arg Leu Thr
225                 230                 235                 240

Val Thr Glu Asp Leu Lys Asn Glu Pro Lys Ser Ser Asp Lys Thr His
                245                 250                 255

Thr Cys Pro Pro Cys Pro Ala Pro Pro Val Ala Gly Pro Ser Val Phe
            260                 265                 270

Leu Phe Pro Pro Lys Pro Lys Asp Thr Leu Met Ile Ser Arg Thr Pro
        275                 280                 285

Glu Val Thr Cys Val Val Val Asp Val Ser His Glu Asp Pro Glu Val
    290                 295                 300

Lys Phe Asn Trp Tyr Val Asp Gly Val Glu Val His Asn Ala Lys Thr
305                 310                 315                 320

Lys Pro Arg Glu Glu Gln Tyr Gln Ser Thr Tyr Arg Val Val Ser Val
                325                 330                 335

Leu Thr Val Leu His Gln Asp Trp Leu Asn Gly Lys Glu Tyr Lys Cys
            340                 345                 350

Lys Val Ser Asn Lys Ala Leu Pro Ala Ser Ile Glu Lys Thr Ile Ser
        355                 360                 365
```

```
Lys Ala Lys Gly Gln Pro Arg Glu Pro Gln Val Cys Thr Leu Pro Pro
            370                 375                 380

Ser Arg Asp Glu Leu Thr Lys Asn Gln Val Ser Leu Ser Cys Ala Val
385                 390                 395                 400

Lys Gly Phe Tyr Pro Ser Asp Ile Ala Val Glu Trp Glu Ser Asn Gly
                405                 410                 415

Gln Pro Glu Asn Asn Tyr Lys Thr Thr Pro Pro Val Leu Asp Ser Asp
            420                 425                 430

Gly Ser Phe Phe Leu Val Ser Lys Leu Thr Val Asp Lys Ser Arg Trp
                435                 440                 445

Gln Gln Gly Asn Val Phe Ser Cys Ser Val Met His Glu Ala Leu His
450                 455                 460

Asn His Tyr Thr Gln Lys Ser Leu Ser Leu Ser Pro
465                 470                 475

<210> SEQ ID NO 53
<211> LENGTH: 457
<212> TYPE: PRT
<213> ORGANISM: Homo sapiens

<400> SEQUENCE: 53

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Ile Ala Thr Tyr Phe Cys Gln Gln Gly Gln Thr Leu Pro Trp
                85                  90                  95

Thr Phe Gly Gln Gly Thr Lys Val Glu Ile Lys Gly Gly Gly Ser Gly
            100                 105                 110

Gly Gly Gly Gln Lys Glu Val Glu Gln Asn Ser Gly Pro Leu Ser Val
        115                 120                 125

Pro Glu Gly Ala Ile Ala Ser Leu Asn Cys Thr Tyr Ser Asp Arg Gly
    130                 135                 140

Ser Gln Ser Phe Phe Trp Tyr Arg Gln Tyr Ser Gly Lys Ser Pro Glu
145                 150                 155                 160

Leu Ile Met Ser Ile Tyr Ser Asn Gly Asp Lys Glu Asp Gly Arg Phe
                165                 170                 175

Thr Ala Gln Leu Asn Lys Ala Ser Gln Tyr Ile Ser Leu Leu Ile Arg
            180                 185                 190

Asp Ser Lys Leu Ser Asp Ser Ala Thr Tyr Leu Cys Ala Val Arg Gly
        195                 200                 205

Ala His Asp Tyr Ala Leu Asn Phe Gly Lys Gly Thr Ser Leu Leu Val
    210                 215                 220

Thr Pro His Ile Glu Pro Lys Ser Ser Asp Lys Thr His Thr Cys Pro
225                 230                 235                 240

Pro Cys Pro Ala Pro Pro Val Ala Gly Pro Ser Val Phe Leu Phe Pro
                245                 250                 255

Pro Lys Pro Lys Asp Thr Leu Met Ile Ser Arg Thr Pro Glu Val Thr
            260                 265                 270
```

```
Cys Val Val Val Asp Val Ser His Glu Asp Pro Glu Val Lys Phe Asn
            275                 280                 285

Trp Tyr Val Asp Gly Val Glu Val His Asn Ala Lys Thr Lys Pro Arg
        290                 295                 300

Glu Glu Gln Tyr Gln Ser Thr Tyr Arg Val Val Ser Val Leu Thr Val
305                 310                 315                 320

Leu His Gln Asp Trp Leu Asn Gly Lys Glu Tyr Lys Cys Lys Val Ser
                325                 330                 335

Asn Lys Ala Leu Pro Ala Ser Ile Glu Lys Thr Ile Ser Lys Ala Lys
            340                 345                 350

Gly Gln Pro Arg Glu Pro Gln Val Tyr Thr Leu Pro Pro Cys Arg Asp
        355                 360                 365

Glu Leu Thr Lys Asn Gln Val Ser Leu Trp Cys Leu Val Lys Gly Phe
370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
                405                 410                 415

Phe Leu Tyr Ser Lys Leu Thr Val Asp Lys Ser Arg Trp Gln Gln Gly
            420                 425                 430

Asn Val Phe Ser Cys Ser Val Met His Glu Ala Leu His Asn His Tyr
        435                 440                 445

Thr Gln Lys Ser Leu Ser Leu Ser Pro
450                 455

<210> SEQ ID NO 54
<211> LENGTH: 476
<212> TYPE: PRT
<213> ORGANISM: Homo sapiens

<400> SEQUENCE: 54

Glu Ala Gly Val Thr Gln Ser Pro Thr His Leu Ile Lys Thr Arg Gly
1               5                   10                  15

Gln Gln Val Thr Leu Arg Cys Ser Pro Lys Ser Gly His Asp Thr Val
            20                  25                  30

Ser Trp Tyr Gln Gln Ala Leu Gly Gln Gly Pro Gln Phe Ile Phe Gln
        35                  40                  45

Tyr Val Arg Gly Glu Glu Arg Gln Arg Gly Asn Phe Pro Asp Arg Phe
    50                  55                  60

Ser Gly His Gln Tyr Pro Asn Tyr Ser Ser Glu Leu Asn Ile Asn Ala
65                  70                  75                  80

Leu Leu Leu Gly Asp Ser Ala Leu Tyr Leu Cys Ala Ser Ser Asp Thr
                85                  90                  95

Val Ser Tyr Glu Gln Tyr Phe Gly Pro Gly Ile Arg Leu Thr Val Thr
            100                 105                 110

Glu Asp Leu Lys Asn Gly Gly Ser Gly Gly Gly Gly Glu Val Gln
        115                 120                 125

Leu Val Gln Ser Gly Ala Glu Val Lys Lys Pro Gly Ala Ser Val Lys
130                 135                 140

Val Ser Cys Lys Ala Ser Gly Tyr Ser Phe Thr Gly Tyr Thr Met Asn
145                 150                 155                 160

Trp Val Arg Gln Ala Pro Gly Gln Gly Leu Glu Trp Met Gly Leu Ile
                165                 170                 175

Asn Pro Tyr Lys Gly Val Ser Thr Tyr Ala Gln Lys Phe Gln Asp Arg
```

```
            180                 185                 190
Val Thr Leu Thr Val Asp Lys Ser Thr Ser Thr Ala Tyr Met Glu Leu
        195                 200                 205

Ser Ser Leu Arg Ser Glu Asp Thr Ala Val Tyr Tyr Cys Ala Arg Ser
    210                 215                 220

Gly Tyr Tyr Gly Asp Ser Asp Trp Tyr Phe Asp Val Trp Gly Gln Gly
225                 230                 235                 240

Thr Leu Val Thr Val Ser Ser Glu Pro Lys Ser Ser Asp Lys Thr His
                245                 250                 255

Thr Cys Pro Pro Cys Pro Ala Pro Pro Val Ala Gly Pro Ser Val Phe
            260                 265                 270

Leu Phe Pro Pro Lys Pro Lys Asp Thr Leu Met Ile Ser Arg Thr Pro
        275                 280                 285

Glu Val Thr Cys Val Val Val Asp Val Ser His Glu Asp Pro Glu Val
    290                 295                 300

Lys Phe Asn Trp Tyr Val Asp Gly Val Glu Val His Asn Ala Lys Thr
305                 310                 315                 320

Lys Pro Arg Glu Glu Gln Tyr Gln Ser Thr Tyr Arg Val Val Ser Val
                325                 330                 335

Leu Thr Val Leu His Gln Asp Trp Leu Asn Gly Lys Glu Tyr Lys Cys
            340                 345                 350

Lys Val Ser Asn Lys Ala Leu Pro Ala Ser Ile Glu Lys Thr Ile Ser
        355                 360                 365

Lys Ala Lys Gly Gln Pro Arg Glu Pro Gln Val Cys Thr Leu Pro Pro
    370                 375                 380

Ser Arg Asp Glu Leu Thr Lys Asn Gln Val Ser Leu Ser Cys Ala Val
385                 390                 395                 400

Lys Gly Phe Tyr Pro Ser Asp Ile Ala Val Glu Trp Glu Ser Asn Gly
                405                 410                 415

Gln Pro Glu Asn Asn Tyr Lys Thr Thr Pro Pro Val Leu Asp Ser Asp
            420                 425                 430

Gly Ser Phe Phe Leu Val Ser Lys Leu Thr Val Asp Lys Ser Arg Trp
        435                 440                 445

Gln Gln Gly Asn Val Phe Ser Cys Ser Val Met His Glu Ala Leu His
    450                 455                 460

Asn His Tyr Thr Gln Lys Ser Leu Ser Leu Ser Pro
465                 470                 475

<210> SEQ ID NO 55
<211> LENGTH: 461
<212> TYPE: PRT
<213> ORGANISM: Homo sapiens

<400> SEQUENCE: 55

Glu Ala Gly Val Thr Gln Ser Pro Thr His Leu Ile Lys Thr Arg Gly
1               5                   10                  15

Gln Gln Val Thr Leu Arg Cys Ser Pro Lys Ser Gly His Asp Thr Val
                20                  25                  30

Ser Trp Tyr Gln Gln Ala Leu Gly Gln Gly Pro Gln Phe Ile Phe Gln
            35                  40                  45

Tyr Val Arg Gly Glu Glu Arg Gln Arg Gly Asn Phe Pro Asp Arg Phe
        50                  55                  60

Ser Gly His Gln Tyr Pro Asn Tyr Ser Ser Glu Leu Asn Ile Asn Ala
65                  70                  75                  80
```

Leu Leu Leu Gly Asp Ser Ala Leu Tyr Leu Cys Ala Ser Ser Asp Thr
            85                  90                  95

Val Ser Tyr Glu Gln Tyr Phe Gly Pro Gly Ile Arg Leu Thr Val Thr
            100                 105                 110

Glu Asp Leu Lys Asn Gly Gly Ser Gly Gly Gly Asp Ile Gln
            115                 120                 125

Met Thr Gln Ser Pro Ser Ser Leu Ser Ala Ser Val Gly Asp Arg Val
130                 135                 140

Thr Ile Thr Cys Arg Ala Ser Gln Asp Ile Arg Asn Tyr Leu Asn Trp
145                 150                 155                 160

Tyr Gln Gln Lys Pro Gly Lys Ala Pro Lys Leu Leu Ile Tyr Tyr Thr
            165                 170                 175

Ser Arg Leu His Ser Gly Val Pro Ser Arg Phe Ser Gly Ser Gly Ser
            180                 185                 190

Gly Thr Asp Tyr Thr Leu Thr Ile Ser Ser Leu Gln Pro Glu Asp Ile
            195                 200                 205

Ala Thr Tyr Phe Cys Gln Gln Gly Gln Thr Leu Pro Trp Thr Phe Gly
            210                 215                 220

Gln Gly Thr Lys Val Glu Ile Lys Glu Pro Lys Ser Ser Asp Lys Thr
225                 230                 235                 240

His Thr Cys Pro Pro Cys Pro Ala Pro Pro Val Ala Gly Pro Ser Val
            245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
            275                 280                 285

Val Lys Phe Asn Trp Tyr Val Asp Gly Val Glu Val His Asn Ala Lys
            290                 295                 300

Thr Lys Pro Arg Glu Glu Gln Tyr Gln Ser Thr Tyr Arg Val Val Ser
305                 310                 315                 320

Val Leu Thr Val Leu His Gln Asp Trp Leu Asn Gly Lys Glu Tyr Lys
            325                 330                 335

Cys Lys Val Ser Asn Lys Ala Leu Pro Ala Ser Ile Glu Lys Thr Ile
            340                 345                 350

Ser Lys Ala Lys Gly Gln Pro Arg Glu Pro Gln Val Tyr Thr Leu Pro
            355                 360                 365

Pro Cys Arg Asp Glu Leu Thr Lys Asn Gln Val Ser Leu Trp Cys Leu
            370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
            405                 410                 415

Asp Gly Ser Phe Phe Leu Tyr Ser Lys Leu Thr Val Asp Lys Ser Arg
            420                 425                 430

Trp Gln Gln Gly Asn Val Phe Ser Cys Ser Val Met His Glu Ala Leu
            435                 440                 445

His Asn His Tyr Thr Gln Lys Ser Leu Ser Leu Ser Pro
450                 455                 460

<210> SEQ ID NO 56
<211> LENGTH: 472
<212> TYPE: PRT
<213> ORGANISM: Homo sapiens

<400> SEQUENCE: 56

Glu Val Gln Leu Val Gln Ser Gly Ala Glu Lys Lys Pro Gly Ala
1               5                   10                  15

Ser Val Lys Val Ser Cys Lys Ala Ser Gly Tyr Ser Phe Thr Gly Tyr
        20                  25                  30

Thr Met Asn Trp Val Arg Gln Ala Pro Gly Gln Gly Leu Glu Trp Met
            35                  40                  45

Gly Leu Ile Asn Pro Tyr Lys Gly Val Ser Thr Tyr Ala Gln Lys Phe
    50                  55                  60

Gln Asp Arg Val Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Tyr Tyr Gly Asp Ser Asp Trp Tyr Phe Asp Val Trp
                100                 105                 110

Gly Gln Gly Thr Leu Val Thr Val Ser Gly Gly Gly Ser Gly Gly
        115                 120                 125

Gly Gly Gln Lys Glu Val Glu Gln Asn Ser Gly Pro Leu Ser Val Pro
    130                 135                 140

Glu Gly Ala Ile Ala Ser Leu Asn Cys Thr Tyr Ser Asp Arg Gly Ser
145                 150                 155                 160

Gln Ser Phe Phe Trp Tyr Arg Gln Tyr Ser Gly Lys Ser Pro Glu Leu
                165                 170                 175

Ile Met Ser Ile Tyr Ser Asn Gly Asp Lys Glu Asp Gly Arg Phe Thr
                180                 185                 190

Ala Gln Leu Asn Lys Ala Ser Gln Tyr Ile Ser Leu Leu Ile Arg Asp
            195                 200                 205

Ser Lys Leu Ser Asp Ser Ala Thr Tyr Leu Cys Ala Val Arg Gly Ala
    210                 215                 220

His Asp Tyr Ala Leu Asn Phe Gly Lys Gly Thr Ser Leu Leu Val Thr
225                 230                 235                 240

Pro His Ile Glu Pro Lys Ser Ser Asp Lys Thr His Thr Cys Pro Pro
                245                 250                 255

Cys Pro Ala Pro Pro Val Ala Gly Pro Ser Val Phe Leu Phe Pro Pro
            260                 265                 270

Lys Pro Lys Asp Thr Leu Met Ile Ser Arg Thr Pro Glu Val Thr Cys
    275                 280                 285

Val Val Val Asp Val Ser His Glu Asp Pro Glu Val Lys Phe Asn Trp
290                 295                 300

Tyr Val Asp Gly Val Glu Val His Asn Ala Lys Thr Lys Pro Arg Glu
305                 310                 315                 320

Glu Gln Tyr Gln Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Ala Leu Pro Ala Ser Ile Glu Lys Thr Ile Ser Lys Ala Lys Gly
    355                 360                 365

Gln Pro Arg Glu Pro Gln Val Cys Thr Leu Pro Pro Ser Arg Asp Glu
370                 375                 380

Leu Thr Lys Asn Gln Val Ser Leu Ser Cys Ala Val Lys Gly Phe Tyr
385                 390                 395                 400

Pro Ser Asp Ile Ala Val Glu Trp Glu Ser Asn Gly Gln Pro Glu Asn
                405                 410                 415

```
Asn Tyr Lys Thr Thr Pro Val Leu Asp Ser Asp Gly Ser Phe Phe
            420                 425                 430

Leu Val Ser Lys Leu Thr Val Asp Lys Ser Arg Trp Gln Gln Gly Asn
        435                 440                 445

Val Phe Ser Cys Ser Val Met His Glu Ala Leu His Asn His Tyr Thr
    450                 455                 460

Gln Lys Ser Leu Ser Leu Ser Pro
465                 470

<210> SEQ ID NO 57
<211> LENGTH: 462
<212> TYPE: PRT
<213> ORGANISM: Homo sapiens

<400> SEQUENCE: 57

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Ile Ala Thr Tyr Phe Cys Gln Gln Gly Gln Thr Leu Pro Trp
                85                  90                  95

Thr Phe Gly Gln Gly Thr Lys Val Glu Ile Lys Gly Gly Gly Ser Gly
            100                 105                 110

Gly Gly Gly Gly Glu Ala Gly Val Thr Gln Ser Pro Thr His Leu Ile
        115                 120                 125

Lys Thr Arg Gly Gln Gln Val Thr Leu Arg Cys Ser Pro Lys Ser Gly
130                 135                 140

His Asp Thr Val Ser Trp Tyr Gln Gln Ala Leu Gly Gln Gly Pro Gln
145                 150                 155                 160

Phe Ile Phe Gln Tyr Val Arg Gly Glu Glu Arg Gln Arg Gly Asn Phe
                165                 170                 175

Pro Asp Arg Phe Ser Gly His Gln Tyr Pro Asn Tyr Ser Ser Glu Leu
            180                 185                 190

Asn Ile Asn Ala Leu Leu Leu Gly Asp Ser Ala Leu Tyr Leu Cys Ala
        195                 200                 205

Ser Ser Asp Thr Val Ser Tyr Glu Gln Tyr Phe Gly Pro Gly Ile Arg
    210                 215                 220

Leu Thr Val Thr Glu Asp Leu Lys Asn Glu Lys Ser Ser Asp Lys
225                 230                 235                 240

Thr His Thr Cys Pro Pro Cys Pro Ala Pro Val Ala Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser His Glu Asp Pro
        275                 280                 285

Glu Val Lys Phe Asn Trp Tyr Val Asp Gly Val Glu Val His Asn Ala
    290                 295                 300

Lys Thr Lys Pro Arg Glu Glu Gln Tyr Gln Ser Thr Tyr Arg Val Val
305                 310                 315                 320
```

-continued

```
Ser Val Leu Thr Val Leu His Gln Asp Trp Leu Asn Gly Lys Glu Tyr
            325                 330                 335

Lys Cys Lys Val Ser Asn Lys Ala Leu Pro Ala Ser Ile Glu Lys Thr
            340                 345                 350

Ile Ser Lys Ala Lys Gly Gln Pro Arg Glu Pro Gln Val Tyr Thr Leu
            355                 360                 365

Pro Pro Cys Arg Asp Glu Leu Thr Lys Asn Gln Val Ser Leu Trp Cys
370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
            405                 410                 415

Ser Asp Gly Ser Phe Phe Leu Tyr Ser Lys Leu Thr Val Asp Lys Ser
            420                 425                 430

Arg Trp Gln Gln Gly Asn Val Phe Ser Cys Ser Val Met His Glu Ala
            435                 440                 445

Leu His Asn His Tyr Thr Gln Lys Ser Leu Ser Leu Ser Pro
            450                 455                 460

<210> SEQ ID NO 58
<211> LENGTH: 472
<212> TYPE: PRT
<213> ORGANISM: Homo sapiens

<400> SEQUENCE: 58

Gln Lys Glu Val Glu Gln Asn Ser Gly Pro Leu Ser Val Pro Glu Gly
1               5                   10                  15

Ala Ile Ala Ser Leu Asn Cys Thr Tyr Ser Asp Arg Gly Ser Gln Ser
            20                  25                  30

Phe Phe Trp Tyr Arg Gln Tyr Ser Gly Lys Ser Pro Glu Leu Ile Met
            35                  40                  45

Ser Ile Tyr Ser Asn Gly Asp Lys Glu Asp Gly Arg Phe Thr Ala Gln
    50                  55                  60

Leu Asn Lys Ala Ser Gln Tyr Ile Ser Leu Leu Ile Arg Asp Ser Lys
65                  70                  75                  80

Leu Ser Asp Ser Ala Thr Tyr Leu Cys Ala Val Arg Gly Ala His Asp
            85                  90                  95

Tyr Ala Leu Asn Phe Gly Lys Gly Thr Ser Leu Leu Val Thr Pro His
            100                 105                 110

Ile Gly Gly Gly Ser Gly Gly Gly Gly Glu Val Gln Leu Val Gln Ser
            115                 120                 125

Gly Ala Glu Val Lys Lys Pro Gly Ala Ser Val Lys Val Ser Cys Lys
130                 135                 140

Ala Ser Gly Tyr Ser Phe Thr Gly Tyr Thr Met Asn Trp Val Arg Gln
145                 150                 155                 160

Ala Pro Gly Gln Gly Leu Glu Trp Met Gly Leu Ile Asn Pro Tyr Lys
            165                 170                 175

Gly Val Ser Thr Tyr Ala Gln Lys Phe Gln Asp Arg Val Thr Leu Thr
            180                 185                 190

Val Asp Lys Ser Thr Ser Thr Ala Tyr Met Glu Leu Ser Ser Leu Arg
            195                 200                 205

Ser Glu Asp Thr Ala Val Tyr Tyr Cys Ala Arg Ser Gly Tyr Tyr Gly
            210                 215                 220

Asp Ser Asp Trp Tyr Phe Asp Val Trp Gly Gln Gly Thr Leu Val Thr
```

```
            225                 230                 235                 240
Val Ser Ser Glu Pro Lys Ser Asp Lys Thr His Thr Cys Pro Pro
                245                 250                 255

Cys Pro Ala Pro Pro Val Ala Gly Pro Ser Val Phe Leu Phe Pro Pro
            260                 265                 270

Lys Pro Lys Asp Thr Leu Met Ile Ser Arg Thr Pro Glu Val Thr Cys
            275                 280                 285

Val Val Val Asp Val Ser His Glu Asp Pro Glu Val Lys Phe Asn Trp
            290                 295                 300

Tyr Val Asp Gly Val Glu Val His Asn Ala Lys Thr Lys Pro Arg Glu
305                 310                 315                 320

Glu Gln Tyr Gln Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Ala Leu Pro Ala Ser Ile Glu Lys Thr Ile Ser Lys Ala Lys Gly
            355                 360                 365

Gln Pro Arg Glu Pro Gln Val Cys Thr Leu Pro Pro Ser Arg Asp Glu
            370                 375                 380

Leu Thr Lys Asn Gln Val Ser Leu Ser Cys Ala Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
            420                 425                 430

Leu Val Ser Lys Leu Thr Val Asp Lys Ser Arg Trp Gln Gln Gly Asn
            435                 440                 445

Val Phe Ser Cys Ser Val Met His Glu Ala Leu His Asn His Tyr Thr
            450                 455                 460

Gln Lys Ser Leu Ser Leu Ser Pro
465                 470

<210> SEQ ID NO 59
<211> LENGTH: 4
<212> TYPE: PRT
<213> ORGANISM: Artificial Sequence
<220> FEATURE:
<223> OTHER INFORMATION: Linker

<400> SEQUENCE: 59

Gly Gly Gly Ser
1

<210> SEQ ID NO 60
<211> LENGTH: 5
<212> TYPE: PRT
<213> ORGANISM: Artificial Sequence
<220> FEATURE:
<223> OTHER INFORMATION: Linker

<400> SEQUENCE: 60

Gly Gly Gly Gly Ser
1               5

<210> SEQ ID NO 61
<211> LENGTH: 5
<212> TYPE: PRT
<213> ORGANISM: Artificial Sequence
<220> FEATURE:
```

```
<223> OTHER INFORMATION: Linker

<400> SEQUENCE: 61

Thr Val Leu Arg Thr
1               5

<210> SEQ ID NO 62
<211> LENGTH: 6
<212> TYPE: PRT
<213> ORGANISM: Artificial Sequence
<220> FEATURE:
<223> OTHER INFORMATION: Linker

<400> SEQUENCE: 62

Thr Val Ser Ser Ala Ser
1               5

<210> SEQ ID NO 63
<211> LENGTH: 7
<212> TYPE: PRT
<213> ORGANISM: Artificial Sequence
<220> FEATURE:
<223> OTHER INFORMATION: Linker

<400> SEQUENCE: 63

Thr Val Leu Ser Ser Ala Ser
1               5
```

DUAL SPECIFICITY POLYPEPTIDE MOLECULE

CROSS REFERENCE TO RELATED APPLICATIONS

This application claims benefit to U.S. Provisional Application No. 62/658,318, filed Apr. 16, 2018, U.S. Provisional Application No. 62/532,713, filed Jul. 14, 2017, German application no. 102017115966.5 filed 14 Jul. 2017, German Application no. 102017119866.0, filed 30 Aug. 2017 and German Application No. 102018108995.3, filed Apr. 16, 2018, the content of which is incorporated herein by reference in its entirety.

This application is related to PCT/EP2018/069151 and PCT/EP2018/069157 filed Jul. 13, 2018.

REFERENCE TO SEQUENCE LISTING SUBMITTED AS A COMPLIANT ASCII TEXT FILE (.txt)

Pursuant to the EFS-Web legal framework and 37 CFR §§ 1.821-825 (see MPEP § 2442.03(a)), a Sequence Listing in the form of an ASCII-compliant text file (entitled "Sequence_Listing_3000058-009002_ST25.txt" created on 2 Dec. 2, 2020, and 194,525 bytes in size) is submitted concurrently with the instant application, and the entire contents of the Sequence Listing are incorporated herein by reference.

FIELD

The present invention relates to a bispecific polypeptide molecule comprising a first polypeptide chain and a second polypeptide chain providing a binding region derived from a T cell receptor (TCR) being specific for a major histocompatibility complex (MHC)-associated peptide epitope, and a binding region derived from an antibody capable of recruiting human immune effector cells by specifically binding to a surface antigen of said cells, as well as methods of making the bispecific polypeptide molecule, and uses thereof.

BACKGROUND OF THE INVENTION

With the development of molecular cloning technology and the deep understanding of antibody engineering, there are diverse bispecific antibody formats ("bispecifics") from which to choose in order to achieve the optimal biological activity and clinical purpose. In cancer therapy, bispecific antibodies have been developed with the purpose of redirecting the activity of immune effector cells to the site of tumor through a first binding domain specific for an epitope on tumor cells and a second binding domain specific for an epitope on the immune effector cells. Bispecific antibodies for retargeting of immune effector cells have been developed in different formats, including formats without fragment crystallizable (Fc) region and IgG-derived formats with symmetric or asymmetric design. Besides retargeting effector cells to the site of cancer, new applications were established for bispecific antibodies. Bispecifics that can inhibit two correlated signaling molecules at the same time can be developed to overcome inherent or acquired resistance and to be more efficient angiogenesis inhibitors. In addition, bispecific antibodies can be employed as promising immune-stimulatory agents to treat various diseases like cancer. Bispecific antibodies can also be used to treat hemophilia A by mimicking the function of factor VIII. Bispecific antibodies also have broad application prospects in bone disorders and infections and diseases of the central nervous system (reviewed in Yang F. et al. Bispecific Antibodies as a Development Platform for New Concepts and Treatment Strategies. Int J Mol Sci. 2016 Dec. 28; 18(1)).

T cells express T cell receptor (TCR) complexes that are able to induce antigen-specific immune responses. Engagement of antigen peptide/major histocompatibility complex (MHC) Class I on the target cell with the TCR induces the formation of an immune synapse and leads to signaling through CD3 co-receptors, which are components of the TCR signaling complex. This signaling cascade directs T cell-mediated killing of the cell expressing the antigen through the release and transfer of granzymes and perforin from the T cell to the target cell.

Historically, discovery and production of single-chain connected variable domains of antibodies (scFvs, described by Bird et al. 1988) served as major driver for the development of bispecific antibodies. This concept finally led to generation of BiTE-molecules and their clinical validation as a potent drug for the treatment of leukemia (Baeuerle, P. A.; Reinhardt, C. Bispecific T-cell engaging antibodies for cancer therapy. Cancer Res. 2009, 69, 4941-4944). In cancer, bispecific antibodies that co-engage the CD3 epsilon subunit and a surface antigen on the tumor cell trigger T cell-mediated killing of the tumor cell while circumventing the need for the direct interaction of the TCR and MHC class I in complex with antigen. This expands the repertoire of T cells able to recognize the tumor and act as effector cells (Baeuerle, P. A.; Reinhardt, C. Bispecific T-cell engaging antibodies for cancer therapy. Cancer Res. 2009, 69, 4941-4944).

Stieglmaier J., et al. (in: Utilizing the BiTE (bispecific T-cell engager) platform for immunotherapy of cancer. Expert Opin Biol Ther. 2015; 15(8):1093-9) describe that various approaches of T-cell-based cancer immunotherapy are currently under investigation, among these are BiTE® (bispecific T-cell engager) antibody constructs, which have a unique design and mechanism of action. They are constructed by genetically linking onto a single polypeptide chain the minimal binding domains of monoclonal antibodies for tumor-associated surface antigens and for the T-cell receptor-associated molecule CD3. Concurrent engagement of the target cell antigen and CD3 leads to activation of polyclonal cytotoxic T-cells, resulting in target cell lysis. Blinatumomab, a BiTE® targeting CD19, is being investigated in a broad range of B-cell malignancies and has recently been approved in the USA by the US FDA for Philadelphia chromosome-negative relapsed/refractory B-acute lymphoblastic leukemia under the trade name BLINCYTO™. The BiTE® platform is one of the clinically most advanced T-cell immunotherapy options.

However the shortcomings of small bispecific molecules, like BiTEs®, have been discovered to be poor production yields, difficult purification processes, aggregation propensity and also a very short serum half-life. To overcome the inherent limitations of this class of molecules various bispecific formats based on human IgG were developed starting with the concept of recombinant bispecific prototype immunoglobulin (Ig)-G-like antibodies as devised more than two decades ago, when Morrison and colleagues fused flexible linker peptides to the C termini of the heavy chains of IgG followed by single-chain variable domains with different binding specificities (Coloma, M. J. and Morrison, S. L. (1997) Design and production of novel tetravalent bispecific antibodies. Nat. Biotechnol. 15, 159-163). The molecules could be differentiated from 'normal' antibodies because they had dual functionalities. Technical hurdles initially hampered further development, causing bispecific antibodies (bsAbs) to remain a topic of R&D primarily in the academic and biotech environment. However, rapidly evolving technologies that enabled the engineering, production, and development of recombinant protein derivatives, combined with renewed interest from the pharmaceutical industry, jump-started the bsAb research field. Today, many different bsAb formats suitable for the development of therapeutic proteins are available (for reviews, see Gramer, mAbs. 2013; 5(6):962-973, Weidle, Cancer Genomics Proteomics. 2013 November-December; 10(6):239-50, Brinkmann, MAbs. 2017 February/March; 9(2):182-212.). In summary, the inclusion of Fc-(fragment crystallizable) parts, consisting of CH2 and CH3 domains led to increased productivity, simplified purification processes and enhanced stability. In addition the serum half-life of such IgG-based drugs was prolonged due to i) the increase in size and ii) the interaction of the Fc-part with the human Fc-receptor FcRn.

Development of IgG-based bispecific formats was further fueled by the advent and incorporation of engineered mutations to facilitate the hetero-dimerization of two differing CH3-domains thereby connecting two different polypeptide chains. The basic concept was introduced by Ridgway J B, et al. (in: 'Knobs-into-holes' engineering of antibody CH3 domains for heavy chain heterodimerization. Protein Eng. 1996 July; 9(7):617-21) who disclosed the 'knobs-into-holes' approach as a novel and effective design strategy for engineering antibody heavy chain homodimers for heterodimerization. In this approach a 'knob' variant was first obtained by replacement of a small amino acid with a larger one in the CH3 domain of a CD4-IgG immunoadhesin: T366Y. The knob was designed to insert into a 'hole' in the CH3 domain of a humanized anti-CD3 antibody created by judicious replacement of a large residue with a smaller one: Y407T. The anti-CD3/CD4-IgG hybrid represents up to 92% of the protein A purified protein pool following co-expression of these two different heavy chains together with the anti-CD3 light chain. In contrast, only up to 57% of the anti-CD3/CD4-IgG hybrid is recovered following co-expression in which heavy chains contained wild-type CH3 domains. Thus knobs-into-holes engineering facilitates the construction of an antibody/immunoadhesin hybrid and likely other Fc-containing bifunctional therapeutics including bispecific immunoadhesins and bispecific antibodies.

Atwell et al, 1997, J Mol Biol (Stable heterodimers from remodeling the domain interface of a homodimer using a phage display library) discloses a knob-into-hole mutation (knob: T366W/hole: T366S+L368A+Y407V) in the CH3 domain of the Fc domain for improved heterodimerization. This concept was further improved by the additional introduction of cysteine-residues to form a stabilizing disulfide-bond between the heterodimeric CH3-domains as described by Merchant et al. 1998, Nature Biotechnology (An Efficient Route to Human Bispecific IgG).

Further concepts to produce heterodimeric molecules were disclosed by Muda et al. 2011, PEDS (Therapeutic assessment of SEED: a new engineered antibody platform designed to generate mono- and bispecific antibodies); Gunasekaran et al. 2010, J Biol Chem (Enhancing antibody Fc heterodimer formation through electrostatic steering effects: applications to bispecific molecules and monovalent IgG); Moore et al. 2011, MAbs (A novel bispecific antibody format enables simultaneous bivalent and monovalent co-engagement of distinct target antigens); Von Kreudenstein et al. 2013, MAbs (Improving biophysical properties of a bispecific antibody scaffold to aid developability: quality by molecular design.) These concepts are summarized and reviewed by Ha et al. 2016, Front Immunol (Immunoglobulin Fc Heterodimer Platform Technology: From Design to Application in Therapeutic Antibodies and Proteins) and Liu et al. 2017, Front Immunol (Fc Engineering for Developing Therapeutic Bispecific Antibodies and Novel scaffolds).

With the inclusion of Fc-parts consisting of Hinges, CH2 and CH3 domains, or parts thereof, into bispecific molecules the problem of unspecific immobilization of these molecules, induced by Fc:Fc-gamma receptor (FcgR) interactions arose. FcgRs are composed of different cell surface molecules (FcgRI, FcgRIIa, FcgRIIb, FcgRIII) binding with differing affinities to epitopes displayed by Fc-parts of IgG-molecules. As such an unspecific (i.e. not induced by either of the two binding domains of an bispecific molecule) immobilization is unfavorable due to i) influence on pharmacokinetics of a molecule and ii) off-target activation of immune effector cells various Fc-variants and mutations to ablate FcgR-binding have been identified.

Morgan et al. 1995, Immunology (The N-terminal end of the CH2 domain of chimeric human IgG1 anti-HLA-DR is necessary for C1q, FcγRI and FcγRIII binding) disclose the exchange of the residues 233-236 of human IgG1 with the corresponding sequence derived from human IgG2 resulting in abolished FcgRI binding, abolished C1q binding and diminished FcgRIII binding.

EP1075496 discloses antibodies and other Fc-containing molecules with variations in the Fc region (233P, 234V, 235A and no residue or G in position 236 and 327G, 330S and 331S) wherein the recombinant antibody is capable of binding the target molecule without triggering significant complement dependent lysis, or cell mediated destruction of the target.

Dual affinity retargeting (DART) molecules are used in order to achieve, for example, an optimal redirected T-cell killing of B-cell lymphoma. The original DART technology is described in Moore et al. (in: Application of dual affinity retargeting molecules to achieve optimal redirected T-cell killing of B-cell lymphoma, Blood. 2011 Apr. 28; 117(17): 4542-51). Comparison with a single-chain, bispecific antibody bearing identical CD19 and CD3 antibody Fv sequences revealed DART molecules to be more potent in directing B-cell lysis. Further evolution of the DART technology was achieved by the DART-Fc-molecules as described in Root et al, 2016 antibodies (Development of PF-06671008, a Highly Potent Anti-P-cadherin/Anti-CD3 Bispecific DART Molecule with Extended Half-Life for the Treatment of Cancer). This molecule combined the high potency of the DARTs with, among other positive characteristics, the extended serum half-life of Fc-based molecules.

The αβTCR (TCR) recognizes antigenic peptides presented by MHC and is responsible for the specificity of T cells. Both α and β chains of the TCR possess variable (V) and constant domains. The V domains are involved in binding antigenic peptide and the constant domains traverse through the T cell membrane. From crystal structure analysis of TCR bound to peptide-MHC complex, complementarity determining regions (CDR) 3 of both the $V_\alpha$ and $V_\beta$ chains preferably interact with peptide, while CDRs 1 and 2 interact with MHC. However, recognition of peptide by CDR 1 and recognition of MHC by CDR 3 has also been described (Piepenbrink et al, The basis for limited specificity and MHC restriction in a T cell receptor interface, Nat Commun, 2013; 4, 1948). The TCR as heterodimer is closely associated with CD3 proteins, CD4 or CD8, and other adhesion and signal transducing proteins. Binding of antigenic peptide by the TCR V regions triggers T cell activation by signal transduction through the TCR constant domains via CD3 and CD4 or CD8 cytoplasmic proteins.

Single-chain TCRs (scTCRs) afford significant advantages in contrast to the full-length TCR format for engineering, soluble protein expression, and clinical potential. From the perspective of soluble protein expression (i.e. manufacturing), scTCRs are produced as a single polypeptide, avoiding the requirement for production of each TCR chain as separate polypeptides and allowing for production of larger quantities of the properly assembled scTCR that binds to its peptide-MHC ligand. This feature can allow for production yields that are necessary for clinical use. Finally, from the clinical perspective, scTCRs consisting of only the V regions (scTv) can be formatted as therapeutics or diagnostic reagents similar to scFv fragments.

US 2006-0166875 discloses a single chain T cell receptor (scTCR) comprising a segment constituted by a TCR alpha chain variable region sequence fused to the N terminus of a TCR alpha chain constant region extracellular sequence, a beta segment constituted by a TCR beta chain variable region fused to the N terminus of a TCR beta chain constant region extracellular sequence, and a linker sequence linking the C terminus of a segment to the N terminus of the beta segment, or vice versa, the constant region extracellular sequences of the alpha and beta segments being linked by a disulfide bond, the length of the linker sequence and the position of the disulfide bond being such that the variable region sequences of the alpha and beta segments are mutually orientated substantially as in native alpha/beta T cell receptors. Complexes of two or more such scTCRs, and use of the scTCRs in therapy and in various screening applications are also disclosed. In contrast to the scTCR described in US 2006-0166875, US 2012-0252742 discloses a soluble human single chain TCR without constant domains, consisting of only the variable fragments of the TCR (scTv), which is useful for many purposes, including the treatment of cancer, viral diseases and autoimmune diseases.

McCormack E, et al (in: Bi-specific TCR-anti CD3 redirected T-cell targeting of NY-ESO-1- and LAGE-1-positive tumors. Cancer Immunol Immunother. 2013 April; 62(4): 773-85) disclose that NY-ESO-1 and LAGE-1 are cancer testis antigens with an ideal profile for tumor immunotherapy, combining up-regulation in many cancer types with highly restricted expression in normal tissues and sharing a common HLA-A*0201 epitope, 157-165. They present data to describe the specificity and anti-tumor activity of a bifunctional ImmTAC, comprising a soluble, high-affinity T-cell receptor (TCR) specific for NY-ESO-1157-165 fused to an anti-CD3 scFv. This reagent, ImmTAC-NYE, is shown to kill HLA-A2, antigen-positive tumor cell lines, and freshly isolated HLA-A2- and LAGE-1-positive NSCLC cells. Employing in vivo optical imaging, the results show in vivo targeting of fluorescently labelled high-affinity NYESO-specific TCRs to HLA-A2-, NY-ESO-1157-165-positive tumors in xenografted mice. In vivo ImmTAC-NYE efficacy was tested in a tumor model in which human lymphocytes were stably co-engrafted into immunodeficient NSG mice harboring tumor xenografts; efficacy was observed in both tumor prevention and established tumor models using a GFP fluorescence readout. Quantitative RT-PCR was used to analyze the expression of both NY-ESO-1 and LAGE-1 antigens in 15 normal tissues, 5 cancer cell lines, 10 NSCLC, and 10 ovarian cancer samples. Overall, LAGE-1 RNA was expressed at a greater frequency and at higher levels than NY-ESO-1 in the tumor samples. ImmTACs comprise a single-chain Fv derived from anti-CD3 antibody UCHT-1 covalently linked to the C- or N-terminus of the alpha or beta chain of the TCR.

EP1868650 is directed at diabody molecules and uses thereof in the treatment of a variety of diseases and disorders, including immunological disorders, infectious disease, intoxication and cancers. The diabody molecules comprise two polypeptide chains that associate to form at least two epitope binding sites, which may recognize the same or different epitopes on the same or differing antigens. Additionally, the antigens may be from the same or different molecules. The individual polypeptide chains of the diabody molecule may be covalently bound through non-peptide bond covalent bonds, such as, but not limited to, disulfide bonding of cysteine residues located within each polypeptide chain. In particular embodiments, the diabody molecules further comprise an Fc region, which is disclosed herein as it allows engineering of antibody-like properties (e.g. long half-life) into the molecule. EP1868650 requires the presence of binding regions of light chain or heavy chain variable domains of an immunoglobulin, and extensively discusses functional Fc receptor binders.

WO 2016/184592 A1 discloses bispecific molecules in which one specificity is contributed by a TCR and the other by an antibody, which is directed against an antigen or epitope on the surface of lymphocytes, but does not disclose the specific arrangement of the elements of the TCR and the antibody variable regions as disclosed herein.

EP2258720A1 is directed to a functional T cell receptor (TCR) fusion protein (TFP) recognizing and binding to at least one MHC-presented epitope, and containing at least one amino acid sequence recognizing and binding an antigen.

It is an object of the present invention to provide improved bispecific molecules capable of targeting peptide-MHC-complexes, that can be easily produced, display high stability and also provide high potency when binding to the respective antigen epitopes. Other objects and advantages of the present invention will become apparent when studying the following description and the preferred embodiments thereof, as well as the respective examples.

In a first aspect of the invention, the above object is solved by providing a dual specificity polypeptide molecule selected from the group of molecules comprising a first polypeptide chain and a second polypeptide chain, wherein: the first polypeptide chain comprises a first binding region of a variable domain (VD1) of an antibody specifically binding to a cell surface antigen of a human immune effector cell, and
a first binding region of a variable domain (VR1) of a TCR specifically binding to an MHC-associated peptide epitope, and
a first linker (LINK1) connecting said domains;
the second polypeptide chain comprises a second binding region of a variable domain (VR2) of a TCR specifically binding to an MHC-associated peptide epitope, and
a second binding region of a variable domain (VD2) of an antibody specifically binding to a cell surface antigen of a human immune effector cell, and
a second linker (LINK2) connecting said domains;
wherein said first binding region (VD1) and said second binding region (VD2) associate to form a first binding site (VD1)(VD2) that binds the epitope of the cell surface molecule;
said first binding region (VR1) and said second binding region (VR2) associate to form a second binding site (VR1)(VR2) that binds said MHC-associated peptide epitope;

wherein said two polypeptide chains are fused to human IgG hinge domains and/or human IgG Fc domains or dimerizing portions thereof, and wherein the said two polypeptide chains are connected by covalent and/or non-covalent bonds between said hinge domains and/or Fc-domains; and wherein the Fc domain comprises at least one effector function silencing mutation at a residue selected from positions 233, 234, 235, 236, 297 and 331, optionally wherein the effector function silencing mutation is generated by replacing at least one residue in position 233, 234, 235, 236, and 331 with the corresponding residue derived from IgG2 or IgG4, and wherein said dual specificity polypeptide molecule is capable of simultaneously binding the cell surface molecule and the MHC-associated peptide epitope, and dual specificity polypeptide molecules, wherein the order of the binding regions in the polypeptide chains is selected from VD1-VR1; VD1-VR2; VD2-VR1; VD2-VR2; VR1-VD1; VR1-VD2; VR2-VD1; VR2-VD2, and wherein the domains are either connected by LINK1 or LINK2. Linker sequences LINK1 and/or LINK2 contain at least one sequence motif selected from GGGS (SEQ ID NO: 59), GGGGS (SEQ ID NO: 60), TVLRT (SEQ ID NO: 61), TVSSAS (SEQ ID NO 62), and TVLSSAS (SEQ ID NO 63a) Antibody-derived domains VD1 and VD2 display an engineered disulfide bridge introducing a covalent bond between VD1 and VD2 and where said cysteines are introduced into framework region (FR) 4 in case of VL and framework region 2 in case of VH.

Preferred is a dual specificity polypeptide molecule comprising a first polypeptide chain and a second polypeptide chain, wherein: the first polypeptide chain comprises a first binding region of a variable domain (VD1) derived from an antibody capable of recruiting human immune effector cells by specifically binding to a surface antigen of said cells, and a first binding region of a variable domain (VR1) derived from a TCR being specific for an MHC-associated peptide epitope, and a first linker portion (LINK1) connecting the two domains; the second polypeptide chain comprises a second binding region of a variable domain (VR2) derived from a TCR being specific for an MHC-associated peptide epitope, and a second binding region of a variable domain (VD2) derived from an antibody capable of recruiting human immune effector cells by specifically binding to a surface antigen of said cells, and a second linker portion (LINK2) connecting the two domains; wherein said first binding region (VD1) and said second binding region (VD2) associate to form a first binding site (VD1)(VD2) that binds the epitope of the cell surface molecule; said first binding region (VR1) and said second binding region (VR2) associate to form a second binding site (VR1)(VR2) that binds said MHC-associated peptide epitope; wherein at least one of said polypeptide chains is connected at its c-terminus to hinge-regions, CH2 and/or CH3-domains or parts thereof derived from human IgG; and wherein said dual specificity polypeptide molecule is capable of simultaneously binding the immune effector cell antigen and the MHC-associated peptide epitope.

Preferably, the dual specificity polypeptide molecule according to the present invention binds with high specificity to both the immune effector cell antigen and a specific antigen epitope presented as a peptide-MHC complex, e.g. with a binding affinity (KD) of about 100 nM or less, about 30 nM or less, about 10 nM or less, about 3 nM or less, about 1 nM or less, e.g. measured by Bio-Layer Interferometry as described in Example 6 or as determined by flow cytometry.

The inventive dual specificity polypeptide molecules according to the present invention are exemplified here by a dual specificity polypeptide molecule comprising a first polypeptide chain comprising SEQ ID No. 16 and a second polypeptide chain comprising SEQ ID No. 17.

In a second aspect of the invention, the above object is solved by providing a nucleic acid(s) encoding for a first polypeptide chain and/or a second polypeptide chain as disclosed herein, or expression vector(s) comprising such nucleic acid. In a third aspect of the invention, the above object is solved by providing a host cell comprising vector(s) as defined herein.

In a fourth aspect of the invention, the above object is solved by providing a method for producing a dual specificity polypeptide molecule according to the present invention, comprising suitable expression of said expression vector(s) comprising the nucleic acid(s) as disclosed in a suitable host cell, and suitable purification of the molecule(s) from the cell and/or the medium thereof.

In a fifth aspect of the invention, the above object is solved by providing a pharmaceutical composition comprising the dual specificity polypeptide molecule according to the invention, the nucleic acid or the expression vector(s) according to the invention, or the cell according to the invention, together with one or more pharmaceutically acceptable carriers or excipients.

In a sixth aspect of the invention, the invention relates to the dual specificity polypeptide molecule according to the invention, the nucleic acid(s) or the expression vector(s) according to the invention, the cell according to the invention, or the pharmaceutical composition according to the invention, for use in medicine.

In a seventh aspect of the invention, the invention relates to the dual specificity polypeptide molecule according to the invention, the nucleic acid or the expression vector(s) according to the invention, the cell according to the invention, or the pharmaceutical composition according to the invention, for use in the treatment of a disease or disorder as disclosed herein, in particular selected from cancer and infectious diseases.

In an eighth aspect of the invention, the invention relates to a method for the treatment of a disease or disorder comprising administering a therapeutically effective amount of the dual specificity polypeptide molecule according to the invention, the nucleic acid or the expression vector(s) according to the invention, the cell according to the invention, or the pharmaceutical composition according to the invention.

In a ninth aspect of the invention, the invention relates to a method of eliciting an immune response in a patient or subject comprising administering a therapeutically effective amount of the dual specificity polypeptide molecule according to the invention or the pharmaceutical composition according to the invention.

In a tenth aspect, the invention relates to a method of killing target cells in a patient or subject comprising administering to the patient an effective amount of the dual specificity polypeptide molecule according to the present invention.

As mentioned above, the invention provides new and improved dual specificity polypeptide molecules. The molecules generally comprise a first polypeptide chain and a second polypeptide chain, wherein the chains jointly provide a variable domain of an antibody specific for an epitope of an immune effector cell surface antigen, and a variable domain of a TCR that is specific for an MHC-associated peptide epitope, e.g. cancer epitope or epitopes presented because of infection, e.g. viral infection, such as HIV. Antibody and TCR-derived variable domains are stabilized by covalent and non-covalent bonds formed between Fc-parts or portions thereof located on both polypeptide chains. The dual specificity polypeptide molecule is then capable of simultaneously binding the cellular receptor and the MHC-associated peptide epitope.

In the context of the present invention, variable domains (VD1) and (VD2) are derived from antibodies capable of recruiting human immune effector cells by specifically binding to a surface antigen of said effector cells. In one particular embodiment, said antibodies specifically bind to epitopes of the TCR-CD3 complex of human T cells, comprising the peptide chains TCRalpha, TCRbeta, CD3gamma, CD3delta, CD3epsilon, and CD3zeta.

The dual specificity polypeptide molecule according to the present invention comprise a first polypeptide and a second polypeptide chain providing a first (VD1) and a second (VD2) binding region, respectively, of a variable domain derived from an antibody capable of recruiting human immune effector cells by specifically binding to a surface antigen of said cells. This first binding region (VD1) and said second binding region (VD2) associate to form a first binding site (VD1)(VD2) that binds the epitope of the immune effector cell surface antigen. Furthermore, the first and the second polypeptide chain of the polypeptide molecule comprises a first (VR1) and a second (VR2) binding region, respectively, of a variable domain derived from a TCR being specific for an MHC-associated peptide epitope. Said first binding region (VR1) and said second binding region (VR2) associate to form a second binding site (VR1)(VR2) that binds said MHC-associated peptide epitope. In one embodiment of the dual specificity polypeptide molecule according to the invention, the order/orientation of the regions in the first polypeptide chain is selected from VD1-LINK1-VR1, and VR1-LINK1-VD1; in another embodiment, in the order/orientation of the regions in the second polypeptide chain is selected from VD2-LINK2-VR2, and VR2-LINK2-VD2, that is, the arrangement of the binding sites can be re-arranged into a "left-handed" or "right-handed" molecule (see, for example, FIG. 5). Furthermore, the configuration of the alpha and beta chains of the TCR-related part can be switched.

In the context of the present invention, the dual affinity polypeptide molecule according to the invention is exemplified by a construct that binds the SLYNTVATL peptide (SEQ ID No. 7) when presented as a peptide-MHC complex. Nevertheless, the concept of the invention is clearly not restricted to this particular peptide, and includes basically any disease- or disorder related epitope that is presented in the context with the MHC molecule. This presentation can be both MHC class-I or -II related. Major histocompatibility complex class I (MHC-I) molecules are present on the surface of all nucleated cells and display a large array of peptide epitopes for surveillance by the $CD8^+$ T cell repertoire. $CD8^+$ T cell responses are essential for control and clearance of viral infections as well as for the elimination of transformed and tumorigenic cells. Examples for preferred peptide epitopes to be recognized can be found in the respective literature, and especially include the peptides as disclosed in tables 1 to 5 of WO 2016/170139; tables 1 to 5 of WO 2016/102272; tables 1 or 2 of WO 2016/156202; tables 1 to 4 of WO 2016/146751; table 2 of WO 2011/113819; tables 1 to 4b of WO 2016/156230; tables 1 to 4b of WO 2016/177784; tables 1 to 4 of WO 2016/202963; tables 1 and 2 of WO 2016/207164; tables 1 to 4 of WO 2017/001491; tables 1 to 4 of WO 2017/005733; tables 1 to 8 of WO 2017/021527; tables 1 to 3 of WO 2017/036936; tables 1 to 4 of PCT/EP2016/073416 for cancer treatment(s), U.S. Publication 2016-0187351, U.S. Publication 2017-0165335, U.S. Publication 2017-0035807, U.S. Publication 2016-0280759, U.S. Publication 2016-0287687, U.S. Publication 2016-0346371, U.S. Publication 2016-0368965, U.S. Publication 2017-0022251, U.S. Publication 2017-0002055, U.S. Publication 2017-0029486, U.S. Publication 2017-0037089, U.S. Publication 2017-0136108, U.S. Publication 2017-0101473, U.S. Publication 2017-0096461, U.S. Publication 2017-0165337, U.S. Publication 2017-0189505, U.S. Publication 2017-0173132, U.S. Publication 2017-0296640, U.S. Publication 2017-0253633, and U.S. Publication 2017-0260249, the contents of each of these applications are herein incorporated by reference in their entireties. In another aspect, the dual affinity polypeptide molecule according to the invention recognizes a peptide consisting of any of those peptides described in the aforementioned patent applications.

In an aspect, the dual affinity polypeptide molecule according to the invention binds or is capable of specifically being recognized/binding to one or more peptides with an overall length of from 8 to 100 amino acids, from 8 and 30 amino acids, from 8 to 16 amino acids, preferably from 8 and 14 amino acids, namely 8, 9, 10, 11, 12, 13, 14 amino acids, in case of the elongated class II binding peptides the length can also be 15, 16, 17, 18, 19, 20, 21 or 22 amino acids. In yet another aspect, the dual affinity polypeptide molecule according to the invention binds or is capable of specifically recognizing/binding to one more peptides with an overall length of from 8 to 12 amino acids, from 8 to 10 amino acids, from 9 to 15 amino acids, from 9 to 14 amino acids, from 9 to 13 amino acids, from 9 to 12 amino acids, from 9 to 11 amino acids; from 10 to 15 amino acids, from 10 to 14 amino acids, from 10 to 13 amino acids, or from 10 to 12 amino acids.

Other suitable epitopes can be identified from databases, such as, for example, the Immune Epitope Database (available at www.iedb.org).

The term "human immune effector cell(s)" refers to a cell within the natural repertoire of cells in the human immune system which, when activated, is able to bring about a change in the viability of a target cell. The term "viability of a target cell" may refer within the scope of the invention to the target cell's ability to survive, proliferate and/or interact with other cells. Such interaction may be either direct, for example when the target cell contacts another cell, or indirect, for example when the target cell secretes substances which have an influence on the functioning of another distant cell. The target cell may be either native or foreign to humans. In the event that the cell is native to humans, the target cell is advantageously a cell which has undergone transformation to become a malignant cell. The native cell may additionally be a pathologically modified native cell, for example a native cell infected with an organism such as a virus, a plasmodium or a bacterium. In the event that the cell is foreign to humans, the target cell is advantageously an invading pathogen, for example an invading bacterium or plasmodium.

Preferred is the dual specificity polypeptide molecule according to the invention, wherein said first and second polypeptide chains further comprise at least one hinge domain and/or an Fc domain or portion thereof. In antibodies, the "hinge" or "hinge region" or "hinge domain" refers to the flexible portion of a heavy chain located between the CH1 domain and the CH2 domain. It is approximately 25 amino acids long, and is divided into an "upper hinge," a "middle hinge" or "core hinge," and a "lower hinge." A "hinge subdomain" refers to the upper hinge, middle (or core) hinge or the lower hinge. The amino acids sequences of the hinges of an IgG1, IgG2, IgG3 and IgG4 molecule are (EU numbering indicated):
IgG1: $E_{216}$PKSCDKTHTCPPCPAPELLG (SEQ ID No. 1)
IgG2: $E_{216}$RKCCVECPPCPAPPVAGP (SEQ ID No. 2)
IgG3: ELKTPLGDTTHTCPRC-PEPKSCDTPPPCPRCPE$_{216}$PKSCDTPPPCPRCPAPEL LG (SEQ ID No. 3)
IgG4: $E_{216}$SKYGPPCPSCPAPEFLG (SEQ ID No. 4)

The core hinge region usually contains at least one cysteine-bridge connecting the two heavy chains. Furthermore, mutations can be made in the lower hinge region to ameliorate unwanted antibody-dependent cell-mediated cytotoxicity (ADCC).

Preferred is a dual specificity polypeptide molecule according to the present invention, comprising at least one IgG fragment crystallizable (Fc) domain, i.e. a fragment crystallizable region (Fc region), the tail region of an antibody that interacts with Fc receptors and some proteins of the complement system. Fc regions contain two or three heavy chain constant domains (CH domains 2, 3, and 4) in each polypeptide chain. The Fc regions of IgGs also bear a highly conserved N-glycosylation site. Glycosylation of the Fc fragment is essential for Fc receptor-mediated activity. The small size of bispecific antibody formats such as BiTEs® and DARTs (~50 kD) can lead to fast clearance and a short half-life. Therefore, for improved pharmacokinetic properties, the scTv-cellular receptor (e.g. CD3) dual specificity polypeptide molecule can be fused to a (human IgG1) Fc domain, thereby increasing the molecular mass. Several mutations located at the interface between the CH2 and CH3 domains, such as T250Q/M428L and M252Y/S254T/T256E+H433K/N434F, have been shown to increase the binding affinity to neonatal Fc receptor (FcRn) and the half-life of IgG1 in vivo. By this the serum half-life of an Fc-containing molecule could be further extended.

In the dual specificity polypeptide molecules of the invention, said Fc domain can comprises a CH2 domain comprising at least one effector function silencing mutation. Preferably, these mutations are introduced into the ELLGGP (SEQ ID No. 50) sequence of human IgG1 (residues 233-238) or corresponding residues of other isotypes) known to be relevant for effector functions. In principle, one or more mutations corresponding to residues derived from IgG2 and/or IgG4 are introduced into IgG1 Fc. Preferred are: E233P, L234V, L235A and no residue or G in position 236. Another mutation is P331S. EP1075496 discloses a recombinant antibody comprising a chimeric domain which is derived from two or more human immunoglobulin heavy chain CH2 domains, which human immunoglobulins are selected from IgG1, IgG2 and IgG4, and wherein the chimeric domain is a human immunoglobulin heavy chain CH2 domain which has the following blocks of amino acids at the stated positions: 233P, 234V, 235A and no residue or G in position 236 and 327G, 330S and 331S in accordance with the EU numbering system, and is at least 98% identical to a CH2 sequence (residues 231-340) from human IgG1, IgG2 or IgG4 having said modified amino acids.

Examples of preferred CH2 partial sequences to be used can be (fully or partially) as follows:
231-APP<u>VA</u>-GPSVFLFPPKPKDTLMISRTPE-VTCVVVDVSHEDPEVKFNWYVDGVE VHNAKTKPRE-EQYQSTYRVVSVLTVLHQDWLNGKEYKCKVSNKA-LPA<u>S</u>IEK-334 (SEQ ID No. 5);

and
231-APP<u>VA</u>-GPSVFLFPPKPKDTLMISRTPE-VTCVVVDVSHEDPEVKFNWYVDGVE VHNAKTKPREEQYN-STYRVVSVLTVLHQDWLNGKEYKCKVSNKAL-PA<u>S</u>IEK-334 (SEQ ID No. 6), with the changes underlined, that in position 297 carry an N (glycosylated variant) or a residue selected from the group of A, G and Q (deglycosylated variant).

In the dual specificity polypeptide molecules of the invention, said Fc domain can comprise a CH3 domain comprising at least one mutation facilitating the formation of heterodimers, wherein the mutations are located at any position selected from 366, 368, 405, and 407. To maximize yield of the desired heterodimeric dual specificity-Fc protein and to simplify purification, "knobs-into-holes" mutations can be engineered into the Fc domain. With this design, Fc domains are driven to form heterodimers instead of their normal homodimers by addition of protruding bulky hydrophobic residues ("knobs") to one chain and creation of complementary hydrophobic pockets ("holes") on the other. A 'knob' variant can be obtained by replacement of a small amino acid with a larger one to insert into a 'hole' in the opposite domain created by replacement of a large residue with a smaller one (Ridgway, J. B. B.; Presta, L. G.; Carter, P. "Knobs-into-holes" engineering of antibody CH3 domains for heavy chain heterodimerization. Protein Eng. 1996, 9, 617-621; WO 2002/002781).

Preferred is a dual specificity polypeptide molecule according to the invention, wherein said knob-into-hole mutation is selected from T366W as knob, and T366'S, L368'A, and Y407'V as hole in the CH3 domain (see, e.g. WO 98/50431). This set of mutations can be further extended by inclusion of the mutations K409A and F405'K as described by Wei et al. (Structural basis of a novel heterodimeric Fc for bispecific antibody production, Oncotarget. 2017). Another knob can be T366Y and the hole is Y407'T.

The dual specificity polypeptide molecules of the invention can furthermore comprise artificially introduced cysteine bridges between at least one cysteine residue on the first polypeptide chain and at least one cysteine residue on the second polypeptide chain in order to improve the stability of the molecules, optimally without interfering with the binding characteristics of the bivalent molecule, and/or for improved heterodimerization. For added stability, a disulfide bond can be introduced through the addition of a single cysteine in the CH3 domain of both the knob and hole chains. Preferred is the dual specificity polypeptide molecule according to the invention, wherein the Fc domain comprises a CH3 domain comprising at least one additional cysteine residue, for example S354C and/or Y349C or L242C and K334C.

Preferred is a dual specificity polypeptide molecule according to the invention wherein the cell surface molecule is known to induce the activation of immune cells, or wherein said CD molecule is selected from the group of immune response-related CD molecules, CD3, such as the CD3γ, CD3δ, and CD3ε chains, CD4, CD7, CD8, CD10, CD11b, CD11c, CD14, CD16, CD18, CD22, CD25, CD28, CD32a, CD32b, CD33, CD41, CD41b, CD42a, CD42b, CD44, CD45RA, CD49, CD55, CD56, CD61, CD64, CD68, CD94, CD90, CD117, CD123, CD125, CD134, CD137, CD152, CD163, CD193, CD203c, CD235a, CD278, CD279, CD287, Nkp46, NKG2D, GITR, FcεRI, TCRalpha/beta, TCRgamma/delta and HLA-DR.

Depending on the combination of the two antigen binding entities of the dual specificity polypeptide molecule according to the invention, specific advantages regarding the function of the molecule, in particular an enhanced activity can be achieved.

Preferred is the exemplary dual specificity polypeptide molecule according to the invention, wherein the regions in the first polypeptide chain SEQ ID No. 28 for VR1, SEQ ID No. 29 for VD1, SEQ ID No. 30 for LINK1; and the regions in the second polypeptide chain comprise SEQ ID No. 31 for VR2, SEQ ID No. 32 for VD2, and SEQ ID No. 30 for LINK2.

Further preferred is the exemplary dual specificity polypeptide molecule according to the invention, wherein the FC region in the first polypeptide chain comprises SEQ ID No. 26 (Fc1), and the FC region in the second polypeptide chain comprises SEQ ID No. 27 (Fc2).

Further preferred is the exemplary dual specificity polypeptide molecule according to the invention comprising a first polypeptide chain comprising SEQ ID No. 16 (1. chain of full molecule) and a second polypeptide chain comprising SEQ ID No. 17 (2. chain of full molecule).

Even further preferred is the exemplary dual specificity polypeptide molecule according to the invention, wherein said first binding site (VD1)(VD2) that binds the epitope of the surface antigen of human immune cells (e.g. CD3) is humanized; and/or said second binding site (VR1)(VR2) that binds said MHC-associated peptide epitope is affinity matured to achieve higher affinity, higher stability, or both.

Humanized antibodies are antibodies (or parts thereof) from non-human species whose protein sequences have been modified to increase their similarity to antibody variants produced naturally in humans. The process of "humanization" is usually applied to monoclonal antibodies developed for administration to humans (for example, antibodies developed as anti-cancer drugs). Suitable methods for humanization are known from the literature, and, for example, reviewed in Olimpieri, Pier Paolo, Paolo Marcatili, and Anna Tramontano. "Tabhu: Tools for Antibody Humanization." Bioinformatics 31.3 (2015): 434-435. PMC; Safdari Y, Farajnia S, Asgharzadeh M, Khalili M. Antibody humanization methods—a review and update. Biotechnol Genet Eng Rev. 2013; 29:175-86; or Ahmadzadeh V, Farajnia S, Feizi M A, Nejad R A. Antibody humanization methods for development of therapeutic applications. Monoclon Antib Immunodiagn Immunother. 2014 April; 33(2):67-73.

In general, in vitro affinity maturation of TCRs and antibodies can be done according to methods described in the literature, in particular using yeast or phage surface display (based on, for example, Holler P D, et al. In vitro evolution of a T cell receptor with high affinity for peptide/MHC. Proc Natl Acad Sci USA. 2000 May 9; 97(10):5387-92; Boder E T et al., Directed evolution of antibody fragments with monovalent femtomolar antigen-binding affinity. Proc Natl Acad Sci USA. 2000 Sep. 26; 97(20):10701-5; and, as a recent example, Zhao Q, et al. Affinity maturation of T-cell receptor-like antibodies for Wilms tumor 1 peptide greatly enhances therapeutic potential. *Leukemia.* 2015; 29(11):2238-2247).

The binding sites (VD1)(VD2) and (VR1)(VR2) of the present description preferably specifically bind to a surface antigen of human immune cells and a peptide-HLA molecule complex, respectively. As used herein in connection with binding sites of the present description, "specific binding" and grammatical variants thereof are used to mean a site having a binding affinity (KD) for a peptide-HLA molecule complex and/or an antibody epitope of 100 µM or less. The binding sites (VD1)(VD2) and (VR1)(VR2) of the present description bind to a CD antibody epitope or a peptide-HLA molecule complex, respectively, with a binding affinity (KD) of about 100 µM or less, about 50 µM or less, about 25 µM or less, or about 10 µM or less. More preferred are high affinity binding sites having binding affinities of about 1 µM or less, about 100 nM or less, about 50 nM or less, about 25 nM or less, about 10 nM or less, about 5 nM or less, about 2 nM or less, about 1 nM or less, about 500 µM or less, about 200 µM or less, about 100 µM or less Non-limiting examples of preferred binding affinity ranges for binding sites of the present invention include about 10 µM to about 100 µM, 100 µM to about 1 nM, 1 nM to about 10 nM; about 10 nM to about 20 nM; about 20 nM to about 30 nM; about 30 nM to about 40 nM; about 40 nM to about 50 nM; about 50 nM to about 60 nM; about 60 nM to about 70 nM; about 70 nM to about 80 nM; about 80 nM to about 90 nM; and about 90 nM to about 100 nM, e.g. measured by Bio-Layer Interferometry as described in Example 6.

In an aspect, the disclosure provides for a polypeptide having at least 50%, at least 60%, at least 70%, at least 80%, at least 90%, at least 95%, at least 96%, at least 97%, at least 98%, or at least 99% sequence identity to an amino acid sequence described herein, for example, amino acid sequences 1 to 58. In another aspect, the disclosure provides for a first or second polypeptide having at least 50%, at least 60%, at least 70%, at least 80%, at least 90%, at least 95%, at least 96%, at least 97%, at least 98%, or at least 99% sequence identity to an amino acid sequence described herein. In yet another aspect, the disclosure provides for a duel specific polypeptide molecule having a sequence identity of at least 50%, at least 60%, at least 70%, at least 80%, at least 90%, at least 95%, at least 96%, at least 97%, at least 98%, or at least 99% sequence identity to one or more amino acid sequences described herein. The disclosure further provides for aspects wherein the percent identity of at least 50%, at least 60%, at least 70%, at least 80%, at least 90%, at least 95%, at least 96%, at least 97%, at least 98%, or at least 99% applies to any of the sequences of the structural regions described in FIG. 1, for example, VD1, VR1, Link1, VR2, VD2, Link2, or hinge region, and as described or being part of the sequences as disclosed herein.

In an aspect, polypeptides or duel specific polypeptide molecules described herein may be altered in various ways including amino acid substitutions, deletions, truncations, and insertions of one or more amino acids. In another aspect, polypeptides or duel specific polypeptide molecules described herein may include 1, 2, 3, 4, 5, 6, 7, 8, 9, 10, 15, 20, 25, 30, 35, 40, 45, or 50 or more amino acid substitutions, deletions or insertions. In yet another aspect, polypeptides or duel specific polypeptide molecules described herein may include 1 to 5, 1 to 10, 1 to 20, 2 to 5, 2 to 10, 5 to 20, 5 to 50, or 10 to 100 amino acid substitutions, deletions or insertions. In an aspect, 1, 2, 3, 4, 5, 6, 7, 8, 9, 10, 15, 20, 25, 30, 35, 40, 45, or 50, or more amino acid substitutions, deletions or insertions applies to any of the structural regions described in FIG. 1, for example, VD1, VR1, Link1, VR2, VD2, Link2, or hinge regions. The disclosure further provides for aspects wherein 1 to 5, 1 to 10, 1 to 20, 2 to 5, 2 to 10, 5 to 20, 5 to 50, or 10 to 100 amino acid substitutions, deletions or insertions applies to the sequences of any of the structural regions described in FIG. 1, for example, VD1, VR1, Link1, VR2, VD2, Link2, or hinge region, and as described or being part of the sequences as disclosed herein.

In an aspect, 1, 2, 3, 4, 5, 6, 7, 8, 9, 10, 15, 20, 25, 30, 35, 40, 45, or 50 or more amino acids may be added to the N-terminus or C-Terminus of a polypeptide or duel specific polypeptide molecule described herein, for example, amino acid sequences 1 to 58.

In an aspect, VR1 may have at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the amino acid sequence of SEQ ID NO: 28.

In an aspect, VD1 may have at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the amino acid sequence of SEQ ID NO: 29.

In an aspect, LINK1 or LINK2 may have at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the amino acid sequence of SEQ ID NO: 30.

In an aspect, VR2 may have at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the amino acid sequence of SEQ ID NO: 31.

In an aspect, VD2 may have at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the amino acid sequence of SEQ ID NO: 32.

In an aspect, hinge may have at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the amino acid sequence of SEQ ID NO: 1, SEQ ID NO: 2, SEQ ID NO: 3, or SEQ ID NO: 4. In an aspect, CH2 domain may have at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the amino acid sequence of SEQ ID NO: 5 or SEQ ID NO: 6. In an aspect, Fc region may have at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the amino acid sequence of SEQ ID NO: 26 or SEQ ID NO: 27.

In an aspect, the disclosure provides for a polypeptide having at least 50%, at least 60%, at least 70%, at least 80%, at least 90%, at least 95%, at least 96%, at least 97%, at least 98%, or at least 99% sequence identity to the amino acid sequence of SEQ ID NO: 43, 44, 45, or 46.

In an aspect, the polypeptides or duel specific polypeptide molecules as disclosed herein can be modified by the substitution of one or more residues at different, possibly selective, sites within the polypeptide chain. Such substitutions may be of a conservative nature, for example, where one amino acid is replaced by an amino acid of similar structure and characteristics, such as where a hydrophobic amino acid is replaced by another hydrophobic amino acid. Even more conservative would be replacement of amino acids of the same or similar size and chemical nature, such as where leucine is replaced by isoleucine. In studies of sequence variations in families of naturally occurring homologous proteins, certain amino acid substitutions are more often tolerated than others, and these are often show correlation with similarities in size, charge, polarity, and hydrophobicity between the original amino acid and its replacement, and such is the basis for defining "conservative substitutions."

In another preferred embodiment of the dual specificity polypeptide molecule according to the invention, said molecule carries an active agent or a portion thereof that is coupled or conjugated thereto. Said active agent can be selected from the group consisting of a detectable label, an immunostimulatory molecule, and a therapeutic agent.

The detectable label can be selected from the group consisting of biotin, streptavidin, an enzyme or catalytically active fragment thereof, a radionuclide, a nanoparticle, a paramagnetic metal ion, or a fluorescent, phosphorescent, or chemiluminescent molecule. Detectable labels for diagnostic purposes include for instance, fluorescent labels, radiolabels, enzymes, nucleic acid probes and contrast reagents.

Therapeutic agents which may be associated with the molecules of the invention include immunomodulators, radioactive compounds, enzymes (perforin for example), chemotherapeutic agents (cis-platin for example), or a toxin. Other suitable therapeutic agents include small molecule cytotoxic agents, i.e. compounds with the ability to kill mammalian cells having a molecular weight of less than 700 Daltons. Such compounds could also contain toxic metals capable of having a cytotoxic effect. Furthermore, it is to be understood that these small molecule cytotoxic agents also include pro-drugs, i.e. compounds that decay or are converted under physiological conditions to release cytotoxic agents. Examples of such agents include cis-platin, maytansine derivatives, rachelmycin, calicheamicin, docetaxel, etoposide, gemcitabine, ifosfamide, irinotecan, melphalan, mitoxantrone, sorfimer sodiumphotofrin II, temozolomide, topotecan, trimetreate glucuronate, auristatin E vincristine and doxorubicin; peptide cytotoxins, i.e. proteins or fragments thereof with the ability to kill mammalian cells. For example, ricin, diphtheria toxin, pseudomonas bacterial exotoxin A, DNase and RNase; radio-nuclides, i.e. unstable isotopes of elements which decay with the concurrent emission of one or more of a or p particles, or γ rays. For example, iodine-131, rhenium-186, indium-111, yttrium-90, bismuth-210 and -213, actinium-225 and astatine-213; chelating agents may be used to facilitate the association of these radio-nuclides to the molecules, or multimers thereof; immuno-stimulants, i.e. immune effector molecules which stimulate immune response. For example, cytokines such as IL-2 and IFN-γ, chemokines such as IL-8, platelet factor 4, melanoma growth stimulatory protein, complement activators; or xenogeneic protein domains, allogeneic protein domains, viral/bacterial protein domains, viral/bacterial peptides.

Another aspect of the present invention then relates to a nucleic acid molecule encoding for a first polypeptide chain and/or a second polypeptide chain as disclosed herein, or an expression vector comprising such a nucleic acid. The nucleic acid molecule can be a DNA, cDNA, PNA, RNA, and combinations thereof. The nucleotide sequence coding for a particular peptide, oligopeptide, or polypeptide may be naturally occurring or they may be synthetically constructed. Generally, DNA segments encoding the peptides, polypeptides, and proteins of this invention are assembled from cDNA fragments and short oligonucleotide linkers, or from a series of oligonucleotides, to provide a synthetic gene that is capable of being expressed in a recombinant transcriptional unit comprising regulatory elements derived from a microbial or viral operon. The term "expression product" means the polypeptide or protein that is the natural translation product of the gene and any nucleic acid sequence coding equivalents resulting from genetic code degeneracy and thus coding for the same amino acid(s). The term "fragment", when referring to a coding sequence, means a portion of DNA comprising less than the complete coding region, whose expression product retains essentially the same biological function or activity as the expression product of the complete coding region. Depending on the intended use, the nucleic acid can be codon-optimized for expression in a suitable (e.g. microbial) host cell. Redundancy in the genetic code allows some amino acids to be encoded by more than one codon, but certain codons are less "optimal" than others because of the relative availability of matching tRNAs as well as other factors (Gustafsson et al., 2004).

The nucleic acid may be, for example, DNA, cDNA, PNA, RNA or combinations thereof, either single- and/or double-stranded, or native or stabilized forms of polynucleotides, such as, for example, polynucleotides with a phosphorothioate backbone and may or may not contain introns so long as it codes for the polypeptide chains.

The nucleic acid (e.g. DNA) may then be comprised and/or expressed in a suitable host to produce a polypeptide comprising the polypeptide chain of the invention. Thus, the nucleic acid (e.g. DNA) encoding the polypeptide chain of the invention may be used in accordance with known techniques, appropriately modified in view of the teachings contained herein, to construct an expression vector, which is then used to transform an appropriate host cell for the expression and production of the polypeptide of the invention, as is known in the art. The nucleic acid (e.g. DNA, or in the case of retroviral vectors, RNA) encoding the polypeptide chain(s) constituting the compound of the invention may be joined to a wide variety of other nucleic acid (e.g. DNA) sequences for introduction into an appropriate host. The companion nucleic acid will depend upon the nature of the host, the manner of the introduction of the DNA into the host, and whether episomal maintenance or integration is desired. Generally, the nucleic acid is inserted into an expression vector, such as a plasmid, in proper orientation and correct reading frame for expression. If necessary, the nucleic acid may be linked to the appropriate transcriptional and translational regulatory control nucleotide sequences recognized by the desired host, although such controls are generally available in the expression vector. The vector is then introduced into the host using standard techniques. Generally, not all of the hosts will be transformed by the vector. Therefore, it will be necessary to select for transformed host cells. One selection technique involves incorporating into the expression vector a nucleic acid sequence, with any necessary control elements, that codes for a selectable trait in the transformed cell, such as antibiotic resistance. Alternatively, the gene for such selectable trait can be on another vector, which is used to co-transform the desired host cell. Host cells that have been transformed by the recombinant nucleic acid of the invention are then cultured for a sufficient time and under appropriate conditions known to those skilled in the art in view of the teachings disclosed herein to permit the expression of the polypeptide, which can then be recovered.

Many expression systems are known, including bacteria (for example *E. coli* and *Bacillus subtilis*), yeasts (for example *Saccharomyces cerevisiae*), filamentous fungi (for example *Aspergillus* spec), plant cells, animal cells and insect cells. Preferably, the system can be mammalian cells such as CHO cells available from the ATCC Cell Biology Collection.

In one embodiment, the description provides a method of producing a molecule as described herein, the method comprising culturing a host cell capable of expressing the polypeptide chain(s) under conditions suitable to promote expression of said chain(s).

In one aspect, to obtain cells expressing molecules of the present description, nucleic acids encoding polypeptide chains comprising TCR-alpha and/or TCR-beta binding domains are cloned into expression vectors, such as gamma retrovirus or lentivirus. In another aspect, to obtain cells expressing molecules of the present description, RNAs are synthesized by techniques known in the art, e.g., in vitro transcription systems. The in vitro-synthesized RNAs are then introduced into suitable cells by electroporation to express polypeptide chains.

To increase the expression, nucleic acids encoding chains of the present description may be operably linked to strong promoters, such as retroviral long terminal repeats (LTRs), cytomegalovirus (CMV), murine stem cell virus (MSCV) U3, phosphoglycerate kinase (PGK), β-actin, ubiquitin, and a simian virus 40 (SV40)/CD43 composite promoter, elongation factor (EF)-1a and the spleen focus-forming virus (SFFV) promoter. In a preferred embodiment, the promoter is heterologous to the nucleic acid being expressed. In addition to strong promoters, expression cassettes of the present description may contain additional elements that can enhance transgene expression, including a central polypurine tract (cPPT), which promotes the nuclear translocation of lentiviral constructs (Follenzi et al., 2000), and the woodchuck hepatitis virus posttranscriptional regulatory element (wPRE), which increases the level of transgene expression by increasing RNA stability (Zufferey et al., 1999).

The alpha and beta binding domain chains of a molecule of the present invention may be encoded by nucleic acids located in separate vectors, or may be encoded by polynucleotides located in the same vector.

In an embodiment, a host cell is engineered to express a molecule of the present description. Host cells of the present description can be allogeneic or autologous with respect to a patient to be treated.

Yet another aspect of the invention relates to a pharmaceutical composition comprising the dual specificity polypeptide molecule according to the present invention, the nucleic acid(s) or the expression vector(s) according to the present invention, or the cell according to the present invention, together with one or more pharmaceutically acceptable carriers or excipients. The compositions of the invention include bulk drug compositions useful in the manufacture of pharmaceutical compositions (e.g., impure or non-sterile compositions) and pharmaceutical compositions (i.e., compositions that are suitable for administration to a subject or patient) which can be used in the preparation of unit dosage forms. Such compositions comprise a prophylactically or therapeutically effective amount of the prophylactic and/or therapeutic dual specificity polypeptide molecule (agent) disclosed herein or a combination of the agent and a pharmaceutically acceptable carrier. Preferably, compositions of the invention comprise a prophylactically or therapeutically effective amount of one or more molecules of the invention and a pharmaceutically acceptable carrier.

The pharmaceutical compositions preferably comprise the molecules either in the free form or as a salt. Preferably, the salts are pharmaceutical acceptable salts of the molecules, such as, for example, the chloride or acetate (trifluoroacetate) salts. It has to be noted that the salts of the molecules according to the present invention differ substantially from the molecules in their state(s) in vivo, as the molecules are not salts in vivo.

An embodiment of the present invention thus relates to a non-naturally occurring molecule according to the invention that has been synthetically produced (e.g. synthesized) as a pharmaceutically acceptable salt. Methods to synthetically produce peptides and/or polypeptides are well known in the art. The salts of the molecules according to the present invention differ substantially from the molecules in their state(s) in vivo, as the molecules as generated in vivo are no salts. Preferably, the salts are pharmaceutically acceptable salts of the molecules. These salts according to the invention include alkaline and earth alkaline salts such as salts of the Hofmeister series comprising as anions $PO_4^{3-}$, $SO_4^{2-}$, $CH_3COO^-$, $Cl^-$, $Br^-$, $NO_3^-$, $ClO_4^-$, $I^-$, $SCN^-$ and as cations $NH_4^+$, $Rb^+$, $K^+$, $Na^+$, $Cs^+$, $Li^+$, $Zn^{2+}$, $Mg^{2+}$, $Ca^{2+}$, $Mn^{2+}$, $Cu^{2+}$ and $Ba^{2+}$. Particularly salts are selected from $(NH_4)_3PO_4$, $(NH_4)_2HPO_4$, $(NH_4)H_2PO_4$, $(NH_4)_2SO_4$, $NH_4CH_3COO$, $NH_4Cl$, $NH_4Br$, $NH_4NO_3$, $NH_4ClO_4$, $NH_4I$, $NH_4SCN$, $Rb_3PO_4$, $Rb_2HPO_4$, $RbH_2PO_4$, $Rb_2SO_4$, $Rb_4CH_3COO$, $Rb_4Cl$, $Rb_4Br$, $Rb_4NO_3$, $Rb_4ClO_4$, $Rb_4I$, $Rb_4SCN$, $K_3PO_4$, $K_2HPO_4$, $KH_2PO_4$, $K_2SO_4$, $KCH_3COO$, $KCl$, $KBr$, $KNO_3$, $KClO_4$, $KI$, $KSCN$, $Na_3PO_4$, $Na_2HPO_4$, $NaH_2PO_4$, $Na_2SO_4$, $NaCH_3COO$, $NaCl$, $NaBr$, $NaNO_3$, $NaClO_4$, $NaI$, $NaSCN$, $ZnCl_2$ $Cs_3PO_4$, $Cs_2HPO_4$, $CsH_2PO_4$, $CS_2SO_4$, $CsCH_3COO$, $CsCl$, $CsBr$, $CsNO_3$, $CsClO_4$, $CsI$, $CsSCN$, $Li_3PO_4$, $Li_2HPO_4$, $LiH_2PO_4$, $Li_2SO_4$, $LiCH_3COO$, $LiCl$, $LiBr$, $LiNO_3$, $LiClO_4$, $LiI$, $LiSCN$, $Cu_2SO_4$, $Mg_3(PO_4)_2$, $Mg_2HPO_4$, $Mg(H_2PO_4)_2$, $Mg_2SO_4$, $Mg(CH_3COO)_2$, $MgCl_2$, $MgBr_2$, $Mg(NO_3)_2$, $Mg(ClO_4)_2$, $Mg_2$, $Mg(SCN)_2$, $MnCl_2$, $Ca_3(PO_4)$, $Ca_2HPO_4$, $Ca(H_2PO_4)_2$, $CaSO_4$, $Ca(CH_3COO)_2$, $CaCl_2$, $CaBr_2$, $Ca(NO_3)_2$, $Ca(ClO_4)_2$, $CaI_2$, $Ca(SCN)_2$, $Ba_3(PO_4)_2$, $Ba_2HPO_4$, $Ba(H_2PO_4)_2$, $BaSO_4$, $Ba(CH_3COO)_2$, $BaCl_2$, $BaBr_2$, $Ba(NO_3)_2$, $Ba(ClO_4)_2$, $BaI_2$, and $Ba(SCN)_2$. Particularly preferred are NH acetate, $MgCl_2$, $KH_2PO_4$, $Na_2SO_4$, KCl, NaCl, and $CaCl_2$, such as, for example, the chloride or acetate (trifluoroacetate) salts.

In an aspect, a polypeptide described herein is in the form of a pharmaceutically acceptable salt. In another aspect, a polypeptide in the form of a pharmaceutical salt is in crystalline form.

In an aspect, a pharmaceutically acceptable salt described herein refers to salts which possess toxicity profiles within a range that is acceptable for pharmaceutical applications.

As used herein, "a pharmaceutically acceptable salt" refers to a derivative of the disclosed peptides wherein the peptide is modified by making acid or base salts of the agent. For example, acid salts are prepared from the free base (typically wherein the neutral form of the drug has a neutral —NH2 group) involving reaction with a suitable acid. Suitable acids for preparing acid salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methane sulfonic acid, ethane sulfonic acid, p-toluenesulfonic acid, salicylic acid, and the like, as well as inorganic acids, e.g., hydrochloric acid, hydrobromic acid, sulfuric acid, nitric acid phosphoric acid and the like. Conversely, preparation of basic salts of acid moieties which may be present on a peptide are prepared using a pharmaceutically acceptable base such as sodium hydroxide, potassium hydroxide, ammonium hydroxide, calcium hydroxide, trimethylamine or the like.

In an aspect, pharmaceutically acceptable salts may increase the solubility and/or stability of peptides of described herein. In another aspect, pharmaceutical salts described herein may be prepared by conventional means from the corresponding carrier peptide or complex by reacting, for example, the appropriate acid or base with peptides or complexes as described herein. In another aspect, the pharmaceutically acceptable salts are in crystalline form or semi-crystalline form. In yet another aspect, pharmaceutically acceptable salts may include, for example, those described in Handbook of Pharmaceutical Salts: Properties, Selection, and Use by P. H. Stahl and C. G. Wermuth (Wiley-VCH 2002) and L. D. Bighley, S. M. Berge, D. C. Monkhouse, in "Encyclopedia of Pharmaceutical Technology". Eds. J. Swarbrick and J. C. Boylan, Vol. 13, Marcel Dekker, Inc., New York, Basel, Hong Kong 1995, pp. 453-499, each of these references is herein incorporated by reference in its entirety.

The invention also encompasses pharmaceutical compositions comprising a dual specificity polypeptide molecule of the invention and a therapeutic antibody (e.g., tumor specific monoclonal antibody) that is specific for a particular cancer antigen, and a pharmaceutically acceptable carrier.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, sodium phosphate, sodium acetate, L-Histidine, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Generally, the ingredients of compositions of the invention are supplied either separately or mixed together in unit dosage form, for example, as a dry lyophilized powder or water free concentrate in a hermetically sealed container such as an ampoule or sachet indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Another aspect of the present invention then relates to the dual specificity polypeptide molecule according to the invention, the nucleic acid or the expression vector according to the invention, the cell according to the invention, or the pharmaceutical composition according to the invention, for use in medicine. In general, the use of the dual specificity polypeptide molecule depends on the medical context of the peptide-antigen(s) that is/are recognized by said molecule, as is also described further below.

Preferred is the dual specificity polypeptide molecule according to the invention, the nucleic acid or the expression vector according to the invention, or the cell according to the invention, or the pharmaceutical composition according to the invention, for use in the treatment or prevention of a disease or disorder selected from immunological disorders, infectious disease, intoxication and cancers, including treatment or prevention of a variety of cancers or other abnormal proliferative diseases, including (but not limited to) the following: carcinoma, including that of the bladder, breast, colon, kidney, liver, lung, ovary, pancreas, stomach, prostate, cervix, thyroid and skin; including squamous cell carcinoma; hematopoietic tumors of lymphoid lineage, including leukemia, acute lymphocytic leukemia, acute lymphoblastic leukemia, B-cell lymphoma, T-cell lymphoma, Burketts' lymphoma; hematopoietic tumors of myeloid lineage, including acute and chronic myelogenous leukemias and promyelocytic leukemia; tumors of mesenchymal origin, including fibrosarcoma and rhabdomyosarcoma; other tumors, including melanoma, seminoma, teratocarcinoma, neuroblastoma and glioma; tumors of the central and peripheral nervous system, including astrocytoma, neuroblastoma, glioma, schwannomas, and osteosarcoma; and other tumors, including melanoma, xeroderma pigmentosum, keratoacanthoma, seminoma, thyroid follicular cancer, and teratocarcinoma. Additional cancers may include but not be limited to follicular lymphomas, carcinomas with p53 mutations, hormone dependent tumors of the breast, prostate and ovary, and precancerous lesions such as familial adenomatous polyposis, and myelodysplastic syndromes. In specific embodiments, malignancy or dysproliferative changes (such as metaplasias and dysplasias), or hyperproliferative disorders, are treated or prevented by the methods and compositions of the invention in the ovary, bladder, breast, colon, lung, skin, pancreas, or uterus. In other specific embodiments, sarcoma, melanoma, or leukemia is treated or prevented by the methods and compositions of the invention.

The invention further relates to methods of eliciting an immune response in a patient or subject comprising administering a therapeutically effective amount of the dual specificity polypeptide molecule according to the invention or the pharmaceutical composition according to the invention. In an aspect, a population of the dual specificity polypeptide molecule according to the invention or the pharmaceutical composition according to the invention is administered to a patient or subject in need thereof.

The invention further relates to a method of killing target cells in a patient or subject comprising administering to the patient an effective amount of the dual specificity polypeptide molecule according to the present invention.

The invention also provides methods for preventing, treating, or managing one or more symptoms associated with an inflammatory disorder in a subject further comprising, administering to said subject a therapeutically or prophylactically effective amount of one or more anti-inflammatory agents according to the invention. The invention also provides methods for preventing, treating, or managing one or more symptoms associated with an autoimmune disease further comprising, administering to said subject a therapeutically or prophylactically effective amount of one or more immunomodulatory agents according to the invention. Infectious diseases that can be treated or prevented by the molecules of the invention are caused by infectious agents including but not limited to viruses, bacteria, fungi, protozoae, and viruses. Viral diseases that can be treated or prevented using the molecules of the invention in conjunction with the methods of the present invention include, but are not limited to, those caused by hepatitis type A, hepatitis type B, hepatitis type C, influenza, varicella, adenovirus, herpes simplex type I (HSV-I), herpes simplex type II (HSV-II), rinderpest, rhinovirus, echovirus, rotavirus, respiratory syncytial virus, papilloma virus, papova virus, cytomegalovirus, echinovirus, arbovirus, hantavirus, coxsackie virus, mumps virus, measles virus, rubella virus, polio virus, small pox, Epstein Barr virus, human immunodeficiency virus type I (HIV-I), human immunodeficiency virus type II (HIV-II), and agents of viral diseases such as viral meningitis, encephalitis, dengue or small pox.

Bacterial diseases that can be treated or prevented using the molecules of the invention in conjunction with the methods of the present invention, that are caused by bacteria include, but are not limited to, mycobacteria rickettsia, mycoplasma, Neisseria, *S. pneumonia, Borrelia burgdorferi* (Lyme disease), *Bacillus antracis* (anthrax), tetanus, streptococcus, staphylococcus, mycobacterium, tetanus, pertussis, cholera, plague, diphtheria, chlamydia, S. aureus and legionella.

Protozoal diseases that can be treated or prevented using the molecules of the invention in conjunction with the methods of the present invention, that are caused by protozoa include, but are not limited to, leishmania, kokzidioa, trypanosoma or malaria. Parasitic diseases that can be treated or prevented using the molecules of the invention in conjunction with the methods of the present invention, that are caused by parasites include, but are not limited to, chlamydia and rickettsia.

Examples of infectious agents and diseases include but are not limited to bacteria (e.g., *Escherichia coli, Klebsiella pneumoniae, Staphylococcus aureus, Enterococcus faecalis, Candida albicans, Proteus vulgaris, Staphylococcus viridans,* and *Pseudomonas aeruginosa*), a pathogen (e.g., B-lymphotropic papovavirus (LPV); *Bordetella pertussis*; Borna Disease virus (BDV); Bovine coronavirus; Choriomeningitis virus; Dengue virus; a virus, *E. coli*; Ebola; Echovirus 1; Echovirus-11 (EV); Endotoxin (LPS); Enteric bacteria; Enteric Orphan virus; Enteroviruses; Feline leukemia virus; Foot and mouth disease virus; Gibbon ape leukemia virus (GALV); Gram-negative bacteria; *Helicobacter pylori*; Hepatitis B virus (HBV); Herpes Simplex Virus; HIV-I; Human cytomegalovirus; Human coronovirus; Influenza A, B and C; *Legionella; Leishmania mexicana; Listeria monocytogenes*; Measles virus; Meningococcus; Morbilliviruses; Mouse hepatitis virus; Murine leukemia virus; Murine gamma herpes virus; Murine retrovirus; Murine coronavirus mouse hepatitis virus; *Mycobacterium avium*-M; *Neisseria gonorrhoeae*; Newcastle disease virus; Parvovirus B 19; *Plasmodium falciparum*; Pox Virus; *Pseudomonas*; Rotavirus; *Salmonella* typhiurium; *Shigella*; Streptococci; T-cell lymphotropic virus 1; Vaccinia virus).

Yet another aspect of the present invention then relates to a method for the treatment of a disease or disorder comprising administering a therapeutically effective amount of the dual specificity polypeptide molecule according to the invention, the nucleic acid or the expression vector according to the invention, the cell according to the invention, or the pharmaceutical composition according to the invention.

The dual specificity polypeptide molecule of the invention may be used in a method of preventing or treating a disease or condition which is ameliorated by administration of the dual specificity polypeptide molecule. Such treatments may be provided in a pharmaceutical composition together with one or more pharmaceutically acceptable carriers or excipients. Therapeutic dual specificity polypeptide molecules will usually be supplied as part of a sterile, pharmaceutical composition which will normally include a pharmaceutically acceptable carrier. This pharmaceutical composition may be in any suitable form, (depending upon the desired method of administering it to a patient). It may be provided in unit dosage form, will generally be provided in a sealed container and may be provided as part of a kit. Such a kit would normally (although not necessarily) include instructions for use. It may include a plurality of said unit dosage forms. The pharmaceutical composition may be adapted for administration by any appropriate route, such as a parenteral (including subcutaneous, intramuscular, or intravenous) route. Such compositions may be prepared by any method known in the art of pharmacy, for example by mixing the active ingredient with the carrier(s) or excipient(s) under sterile conditions.

In an aspect, peptides or other molecules described herein may be combined with an aqueous carrier. In an aspect, the aqueous carrier is selected from ion exchangers, alumina, aluminum stearate, magnesium stearate, lecithin, serum proteins, such as human serum albumin, buffer substances such as phosphates, glycine, sorbic acid, potassium sorbate, partial glyceride mixtures of saturated vegetable fatty acids, salts or electrolytes, such as protamine sulfate, disodium hydrogen phosphate, dicalcium phosphate, potassium hydrogen phosphate, sodium chloride, zinc salts, colloidal silica, magnesium trisilicate, polyvinyl pyrrolidone, polyvinylpyrrolidone-vinyl acetate, cellulose-based substances (e.g., microcrystalline cellulose, hydroxypropyl methylcellulose, hydroxypropyl methylcellulose acetate succinate, hydroxypropyl methylcellulose Phthalate), starch, lactose monohydrate, mannitol, trehalose sodium lauryl sulfate, and crosscarmellose sodium, polyethylene glycol, sodium carboxymethylcellulose, polyacrylates, polymethacrylate, waxes, polyethylene-polyoxypropylene-block polymers, polyethylene glycol and wool fat.

In an aspect, the aqueous carrier contains multiple components, such as water together with a non-water carrier component, such as those components described herein. In another aspect, the aqueous carrier is capable of imparting improved properties when combined with a peptide or other molecule described herein, for example, improved solubility, efficacy, and/or improved immunotherapy. In addition, the composition can contain excipients, such as buffers, binding agents, blasting agents, diluents, flavors, lubricants, etc. A "pharmaceutically acceptable diluent," for example, may include solvents, bulking agents, stabilizing agents, dispersion media, coatings, antibacterial and antifungal agents, isotonic and absorption delaying agents, and the like which are physiologically compatible. Examples of pharmaceutically acceptable diluents include one or more of saline, phosphate buffered saline, dextrose, glycerol, ethanol, and the like as well as combinations thereof. In many cases it will be preferable to include one or more isotonic agents, for example, sugars such as trehalose and sucrose, polyalcohols such as mannitol, sorbitol, or sodium chloride in the composition. Pharmaceutically acceptable substances such as wetting or minor amounts of auxiliary substances such as wetting or emulsifying agents, preservatives or buffers, are also within the scope of the present invention. In addition, the composition can contain excipients, such as buffers, binding agents, blasting agents, diluents, flavors, and lubricants.

Dosages of the dual specificity polypeptide molecules of the present invention can vary between wide limits, depending upon the disease or disorder to be treated, the age and condition of the individual to be treated, etc.; for example, a suitable dose range for a dual specificity polypeptide molecule may be between 25 ng/kg and 50 µg/kg. A physician will ultimately determine appropriate dosages to be used.

Pharmaceutical compositions, vectors, nucleic acids and cells of the invention may be provided in substantially pure form, for example at least 80%, at least 85%, at least 90%, at least 91%, at least 92%, at least 93%, at least 94%, at least 95%, at least 96%, at least 97%, at least 98%, at least 99% or 100% pure.

Preferred features of each aspect of the invention are as for each of the other aspects mutatis mutandis. The prior art documents mentioned herein are incorporated to the fullest extent permitted by law. Although the present invention and its advantages have been described in detail, it should be understood that various changes, substitutions and alterations can be made herein without departing from the spirit and scope of the invention as defined in the appended claims. The present invention will be further illustrated in the following Examples which are given for illustration purposes only and are not intended to limit the invention in any way.

EXAMPLES

Example 1

Design of Fc-Containing Bispecific TCR/mAb Diabodies and Control Molecules.

Figure 1:
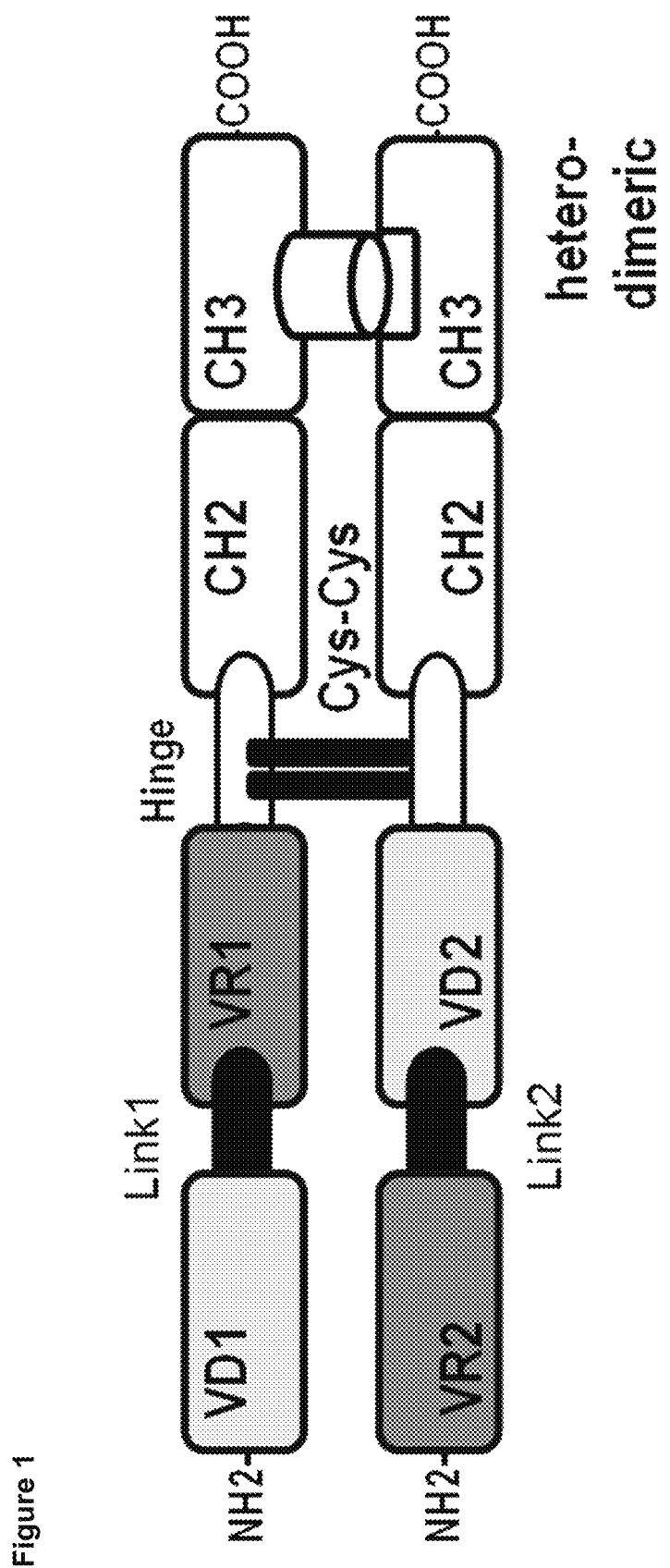
FIG. 1 shows a schematic overview over a preferred embodiment of the present invention, the human IgG1 Fc-containing dual specificity polypeptide molecule. VD1, VD2=variable domains derived from antibody; VR1, VR2=variable domains derived from TCR; Link1, Link2=connecting linkers; Cys-Cys=cysteine bridges.
Figure 2:
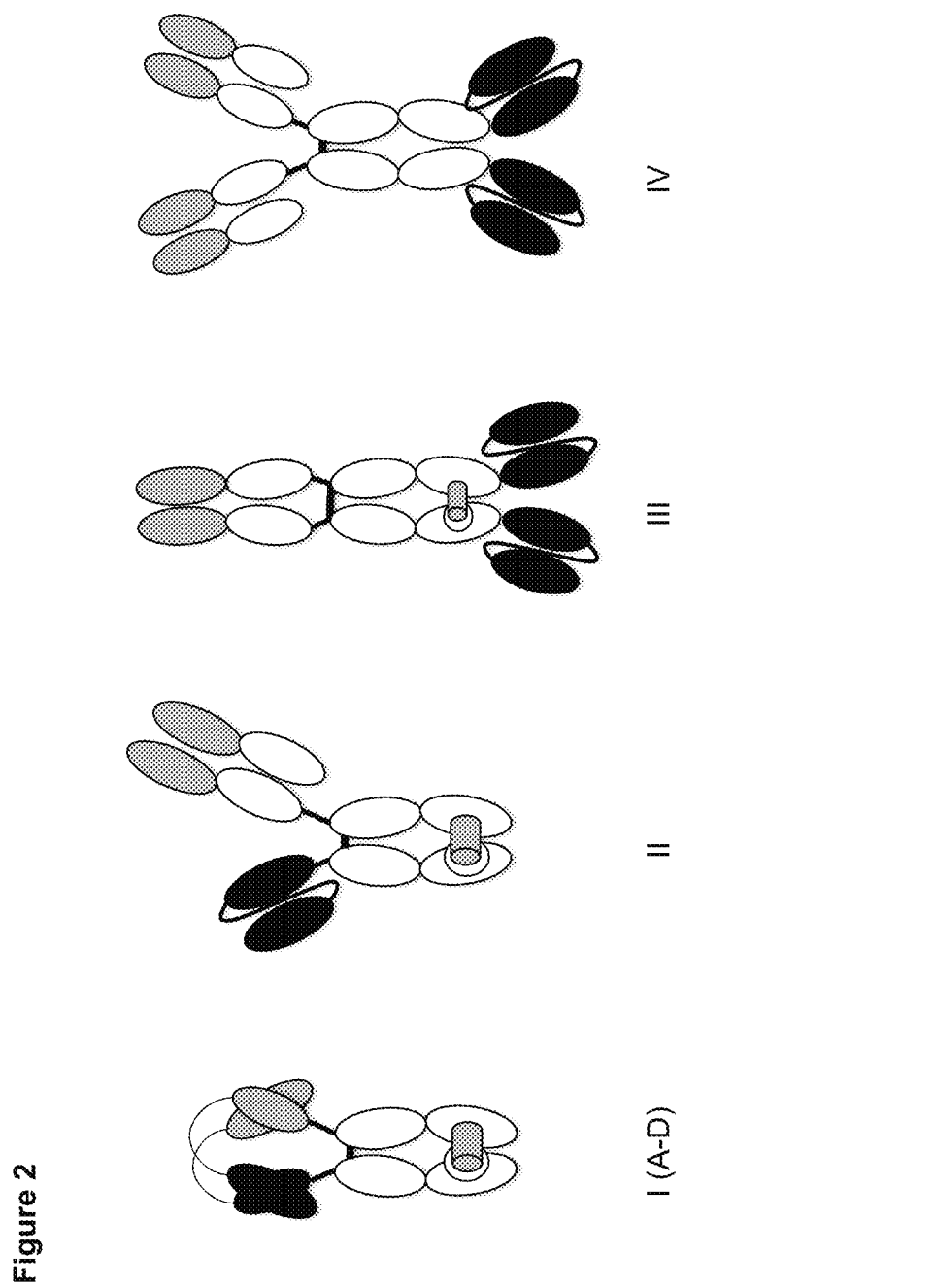
FIG. 2 shows a schematic overview over 4 different constructs of IgG Fc-containing dual specificity polypeptide molecules as tested in the context of the present invention. black=TCR-derived variable domains; light gray=antibody-derived variable domains; white=constant domains derived from human IgG. Knob-hole mutations are indicated by a cylinder. Diabody molecules IA-ID are according to the invention.

Fc-containing bispecific TCR/mAb diabodies and control molecules (as depicted in FIG. 2) were designed to specifically bind to the human TCR-CD3 complex and to the peptide:MHC complex comprising the HIV-derived peptide SLYNTVATL (SQ ID No. 7) bound to HLA-A2*01. For targeting TCR-CD3 complex, VH and VL domains derived from the CD3-specific, humanized antibody hUCHT1(V9) described by Zhu et al. (Identification of heavy chain residues in a humanized anti-CD3 antibody important for efficient antigen binding and T cell activation. *J Immunol*, 1995, 155, 1903-1910) or VH and VL domains derived from the alpha/beta TCR-specific antibody BMA031 described in Shearman et al. (Construction, expression and characterization of humanized antibodies directed against the human alpha/beta T cell receptor. *J Immunol*, 1991, 147, 4366-73) and employed in the humanized version variant 10 (data generated in-house) were used. For targeting peptide:MHC complex, Valpha and Vbeta domains of the previously described stability and affinity maturated, human single chain T-cell receptor 868Z11 disclosed by Aggen et al. (Identification and engineering of human variable regions that allow expression of stable single-chain T cell receptors. *PEDS*, 2011, 24, 361-372) were utilized.

In case of Fc-containing bispecific TCR/mAb diabodies DNA-sequences coding for various combinations of VH and VL (corresponding to VD1 and VD2, respectively) and Va and Vb (corresponding to VR1 and VR2, respectively), as well as coding for linkers Link1 and Link2 were obtained by gene synthesis. Resulting DNA-sequences were cloned in frame into expression vectors coding for hinge region, CH2 and CH3 domain derived from human IgG4 [Accession #: K01316] and IgG1 [Accession #: P01857], respectively and were further engineered. Engineered was performed to incorporate knob-into-hole mutations into CH3-domains with and without additional interchain disulfide bond stabilization; to remove an N-glycosylation site in CH2 (e.g. N297Q mutation); to introduce Fc-silencing mutations; to introduce additional disulfide bond stabilization into VL and VH, respectively, according to the methods described by Reiter et al. (Stabilization of the Fv Fragments in Recombinant Immunotoxins by Disulfide Bonds Engineered into Conserved Framework Regions. Biochemistry, 1994, 33, 5451-5459). An overview of produced bispecific TCR/mAb diabodies, the variants as well as the corresponding sequences are listed in Table 1.

TABLE 1

Overview of all generated and evaluated Fc-containing bispecific TCR/mAb diabodies:
KiH: Knob-into-hole; K/O: Fc-silenced; KiH-ds: Knob-into-hole stabilized with artificial disulfide-bond to connect CH3:CH3'; ds-hUCHT1 (V9): disulfide-bond stabilized hUCHT1 (V9) variable domains; Link1: Linker connecting VR1 and VD1.

| Molecule | TCR | mAb | SEQ IDs | modifications |
|---|---|---|---|---|
| IA-IgG4 | 868Z11 | hUCHT1(V9) | SEQ ID No. 8<br>SEQ ID No. 9 | IgG4 (KiH) |
| IA_1 | 868Z11 | hUCHT1(V9) | SEQ ID No. 10<br>SEQ ID No. 11 | IgG1 (K/O, KiH) |
| IA_2 | 868Z11 | hUCHT1(V9) | SEQ ID No. 12<br>SEQ ID No. 13 | IgG1 (K/O, KiH-ds) |
| IA_3 | 868Z11 | ds-hUCHT1(V9) | SEQ ID No. 14<br>SEQ ID No. 15 | IgG1 (K/O, KiH-ds) |
| ID_1 | 868Z11 | ds-hUCHT1(V9) | SEQ ID No. 16<br>SEQ ID No. 17 | IgG1 (K/O, KiH-ds) |
| IC_4 | 868Z11 | hBMA031(var10) | SEQ ID No. 18<br>SEQ ID No. 19 | IgG1 (K/O, KiH-ds) |
| IC_5 | 868Z11 | hBMA031(var10) | SEQ ID No. 20<br>SEQ ID No. 21 | IgG1 (K/O, KiH-ds) extended Link1 |
| ID_4 | 868Z11 | hBMA031(var10) | SEQ ID No. 22<br>SEQ ID No. 23 | IgG1 (K/O, KiH-ds) |
| ID_5 | 868Z11 | hBMA031(var10) | SEQ ID No. 24<br>SEQ ID No. 25 | IgG1 (K/O, KiH-ds) extended Link1 |
| IA_5 | R16P1C10I | hUCHT1(Var17) | SEQ ID No. 43<br>SEQ ID No. 44 | IgG1 (K/O, KiH-ds) |
| IA_6 | R16P1C10I#6 | hUCHT1(Var17) | SEQ_ID No. 45<br>SEQ ID No. 46 | IgG1 (K/O, KiH-ds) |

Various control molecules exhibiting the same specificities were constructed Table 2 utilizing said VH, VL, Valpha and Vbeta domains in combinations with IgG1- or IgG4-derived constant domains comprising engineered features as described above.

TABLE 2

Overview of all generated and evaluated Fc-containing bispecific control molecules:
KiH: Knob-into-hole; K/O: Fc-silenced.

| Molecule | TCR | mAb | SEQ IDs | modifications |
|---|---|---|---|---|
| III-IgG4 | 868Z11 | hUCHT1(V9) | SEQ ID No. 38<br>SEQ ID No. 39 | IgG4 (KiH) |
| IV-IgG4 | 868Z11 | hUCHT1(V9) | SEQ ID No. 40<br>SEQ ID No. 41 | IgG4 |
| II | 868Z11 | hUCHT1(V9) | SEQ ID No. 33<br>SEQ ID No. 34 | IgG1 (K/O, KiH) |
| III | 868Z11 | hUCHT1(V9) | SEQ ID No. 35<br>SEQ ID No. 36 | IgG1 (K/O, KiH) |
| IV | 868Z11 | hUCHT1(V9) | SEQ ID No. 37<br>SEQ ID No. 42 | IgG1 (K/O) |

Example 2

Production and Purification of Fc-Containing Bispecific TCR/mAb Diabodies

Vectors for the expression of recombinant proteins were designed as mono-cistronic, controlled by HCMV-derived promoter elements, pUC19-derivatives. Plasmid DNA was amplified in *E. coli* according to standard culture methods and subsequently purified using commercial-available kits (Macherey & Nagel). Purified plasmid DNA was used for transient transfection of CHO-S cells according to instructions of the manufacturer (ExpiCHO™ system; Thermo Fisher Scientific). Transfected CHO-cells were cultured for 6-14 days at 32° C. to 37° C. and received one to two feeds of ExpiCHO™ Feed solution.

Conditioned cell supernatant was harvested by centrifugation (4000×g; 30 minutes) and cleared by filtration (0.22 µm). Bispecific molecules were purified using an Äkta Pure 25 L FPLC system (GE Lifesciences) equipped to perform affinity and size-exclusion chromatography in line. Affinity chromatography was performed on protein A columns (GE Lifesciences) following standard affinity chromatographic protocols. Size exclusion chromatography was performed directly after elution (pH 2.8) from the affinity column to obtain highly pure monomeric protein using Superdex 200 µg 16/600 columns (GE Lifesciences) following standard protocols. Protein concentrations were determined on a NanoDrop system (Thermo Scientific) using calculated extinction coefficients according to predicted protein sequences. Concentration, if needed, and buffer exchange was performed using Vivaspin devices (Sartorius). Finally, purified molecules were stored in phosphate-buffered saline at concentrations of about 1 mg/mL at temperatures of 2-8° C.

As therapeutic proteins shall exhibit reasonable stability upon acidic exposure to facilitate robust industrial purification processes the percentage of monomeric protein eluting from the protein A capture column was assessed (Table 3). It is obvious that the introduction of stabilizing mutations into molecules as well as selection of distinct orientations of binding domains markedly impact the stability upon acidic exposure.

TABLE 3

Fraction of monomeric protein after acidic elution from capture column:

| Molecule | Monomer eluted from capture column (% of total peak area) |
|---|---|
| IA-IgG4 (VH-beta) | n.d. |
| IA_1 (VH-beta) | 49 |
| IA_2 (VH-beta) | 54 |
| IA_3 (dsVH-beta) | 63 |
| ID_1 (alpha-dsVH) | 46 |
| IC_4 (VH-alpha) | 62 |
| IC_5 (VH-alpha) | 67 |
| ID_4 (alpha-VH) | 65 |
| ID_5 (alpha-VH) | 69 |
| II | 39 |
| III | 51 |
| IV | 76 |

Figure 3:
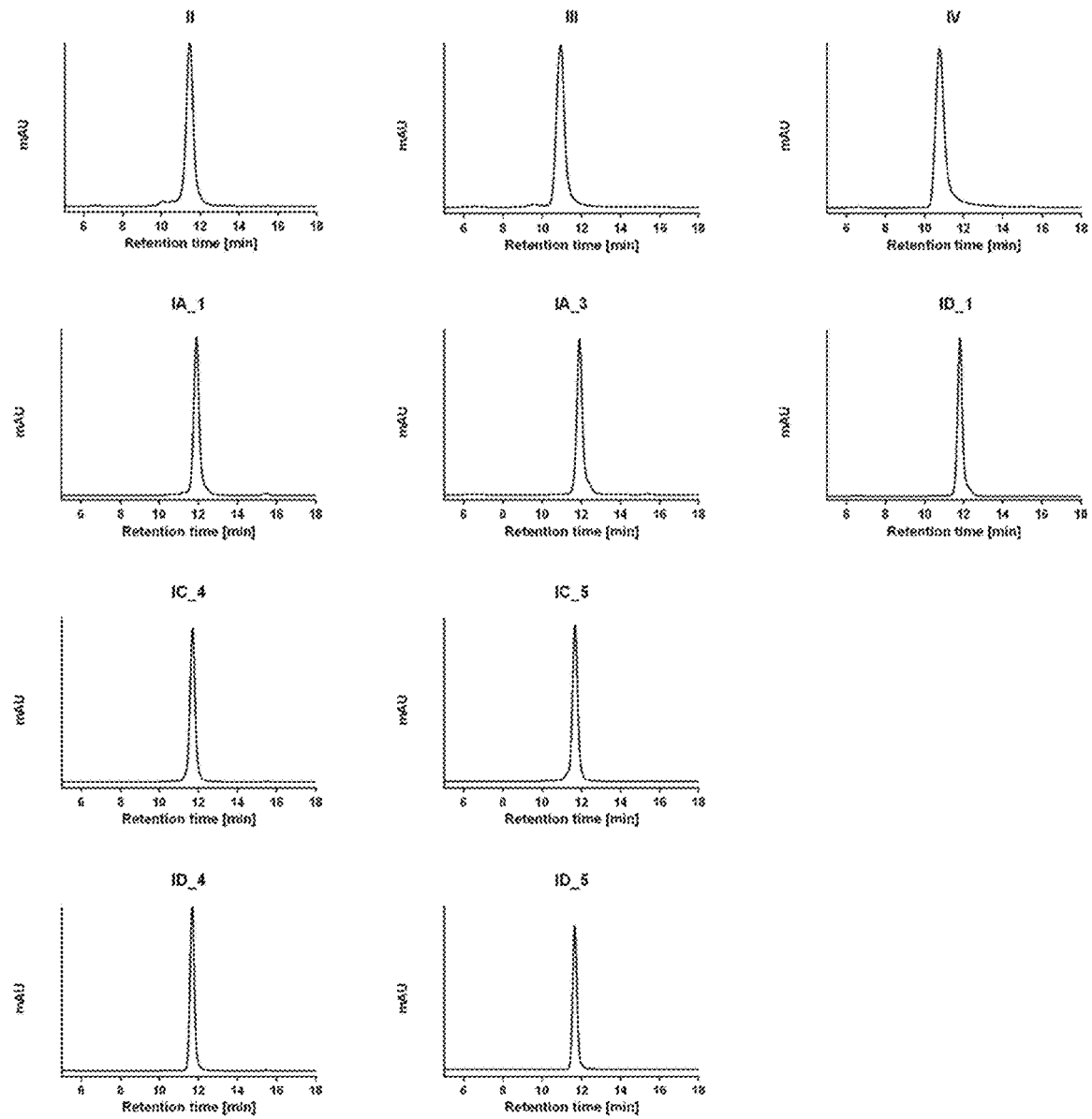
FIG. 3 shows the HPLC-SEC analysis of different bispecific TCR/mAb molecules with a molecular design according to the constructs depicted in FIG. 2, which were purified by a 2-column purification process. The monomer contents of the different molecules were determined as follows. II: 93.84%; III: 96.54%; IV: 98.49%; IA_1: 95.48%; IA_3: 98.45%; ID_1: 95.75%; IC_4: 95.22%; IC_5: 92.76%; ID_4: 99.31%; ID_5: 99.44%.

After size exclusion chromatography, the purified bispecific molecules demonstrated high purity (>93% of monomeric protein) as determined by HPLC-SEC on MabPac SEC-1 columns (5 μm, 7.8×300 mm) running in 50 mM sodium-phosphate pH 6.8 containing 300 mM NaCl within an Agilent 1100 system (see FIG. 3). Non-reducing and reducing SDS-PAGE confirmed the purity and expected size of the different dual specificity TCR/mAb molecules (data not shown).

Example 3

Specific and Target Cell-Dependent T Cell Activation Induced by Fc-Containing TCR/mAb Diabodies The potency of Fc-containing TCR/mAb diabodies with respect to T cell activation was assessed using the T Cell Activation Bioassay (Promega). The assay consists of a genetically engineered Jurkat cell line that expresses a luciferase reporter driven by an NFAT-response element (NFAT-RE). Assays were performed according to the manufacturer. Briefly, T2 cells either loaded with the HIV-specific peptide SLYNTVATL (SEQ ID No. 7) or left without peptide loading (unloaded control) were subsequently co-cultured with Promega's modified Jurkat cells in presence of increasing concentrations of bispecific TCR/mAb molecules. Jurkat reporter T cell activation was analyzed after 16-20 hours by measuring luminescence intensity.

Figure 4:
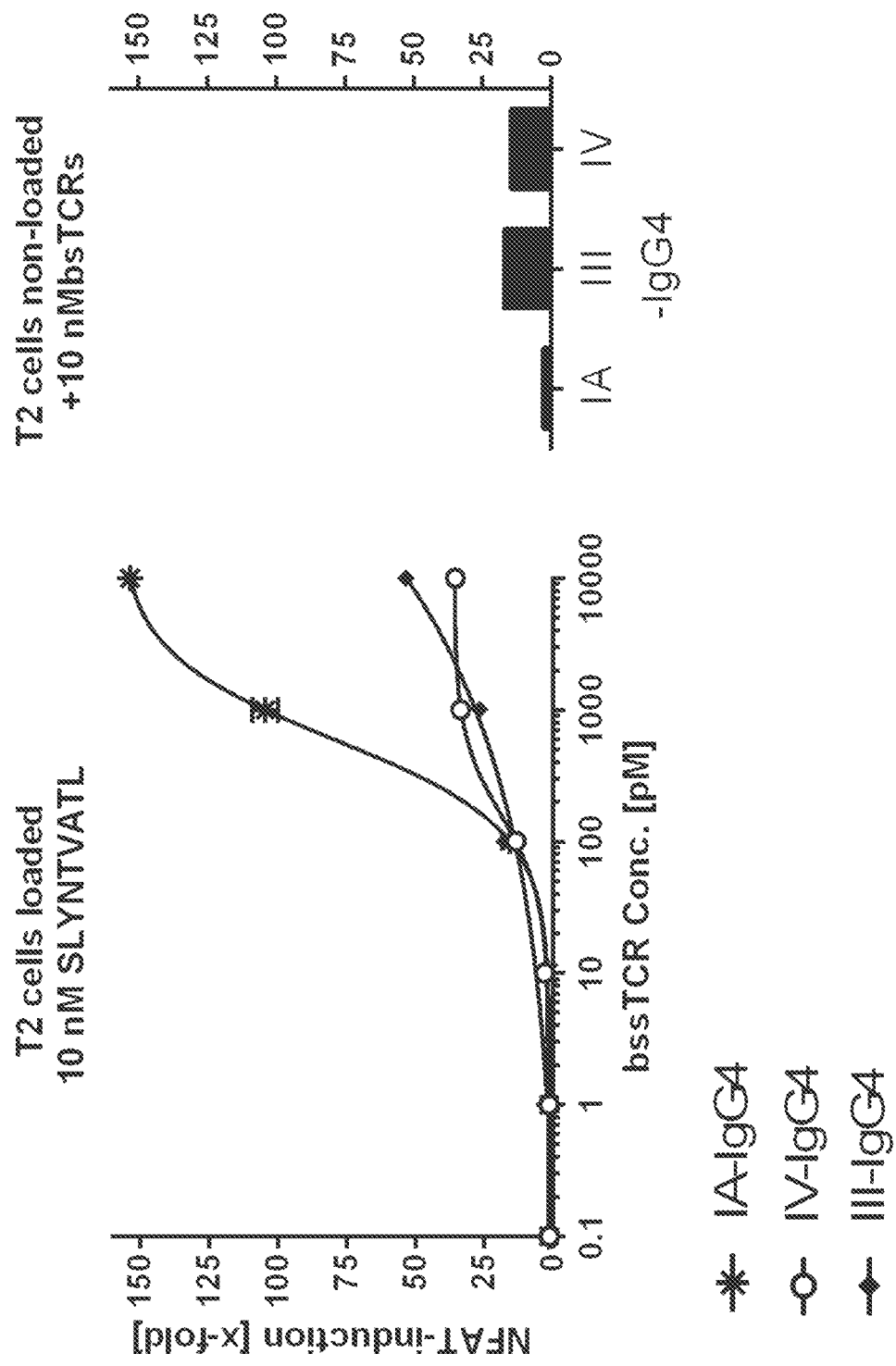
FIG. 4 shows the results of the potency assay with different bispecific TCR/mAb constructs (as shown in FIG. 2) designed as IgG4-based molecules. Jurkat_NFATRE_luc2 cells were co-incubated with HIV-peptide SLYNTVATL (SEQ ID No. 7) loaded T2 cells in the presence of increasing concentrations of bispecific TCR (bssTCR) molecules. The bispecific TCR/mAb diabody molecule IA-IgG4 exhibited a higher potency than two alternative dual specificity TCR/mAb molecules.
Figure 5:
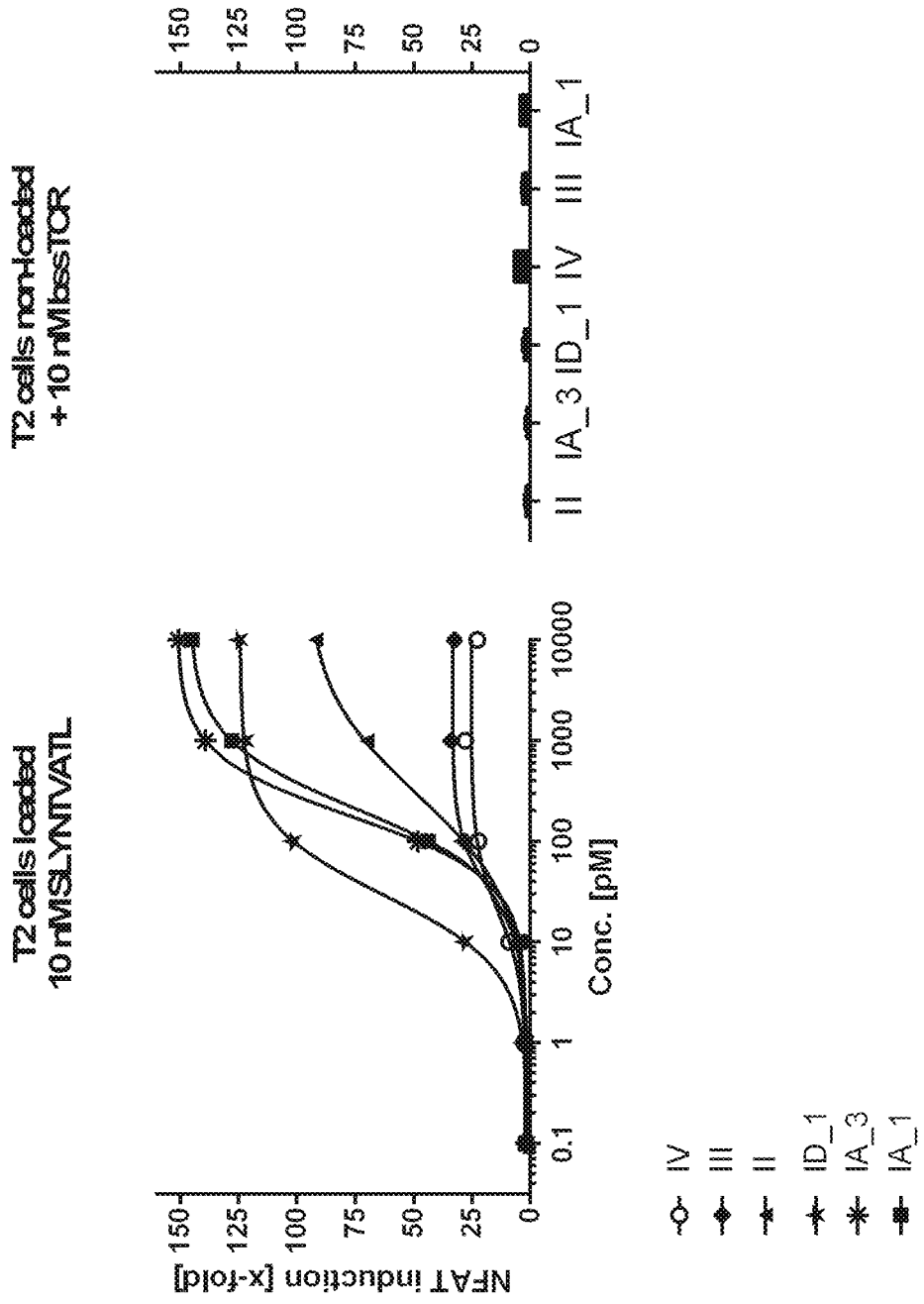
FIG. 5 shows the results of the potency assay with different bispecific TCR/mAb constructs (as shown in FIG. 2) designed as IgG1-based molecules. Jurkat_NFATRE_luc2 cells were co-incubated with HIV-peptide SLYNTVATL (SEQ ID No. 7) loaded T2 cells in the presence of increasing concentrations of bispecific TCR (bssTCR) molecules. The bispecific TCR/mAb diabody molecules ID_1, IA_3 and IA1 exhibited markedly higher potency than three alternative dual specificity TCR/mAb molecules.

Representative potency assay results are depicted for IgG4-based (FIG. 4) and IgG1-based bispecific TCR/mAb molecules (FIG. 5), respectively. The data indicate that regardless of the IgG isotype of the constant domains used, the Fc-containing TCR/mAb diabody constructs IA and ID showed superior T cell activation compared to the alternative bispecific TCR/mAb constructs II, III and IV as measured by the magnitude of activation and/or respective EC50-values. Furthermore, the unspecific T cell activation of Fc-containing TCR/mAb diabodies induced against unloaded T2 cells was reduced or at least equal to the level of unspecific activation observed for the alternative bispecific TCR/mAb constructs. According to above results the dual specificity TCR/mAb diabody molecules are preferred molecules for therapeutic intervention as they induce strong effector T cell activation in a highly target-dependent manner.

Figure 10:
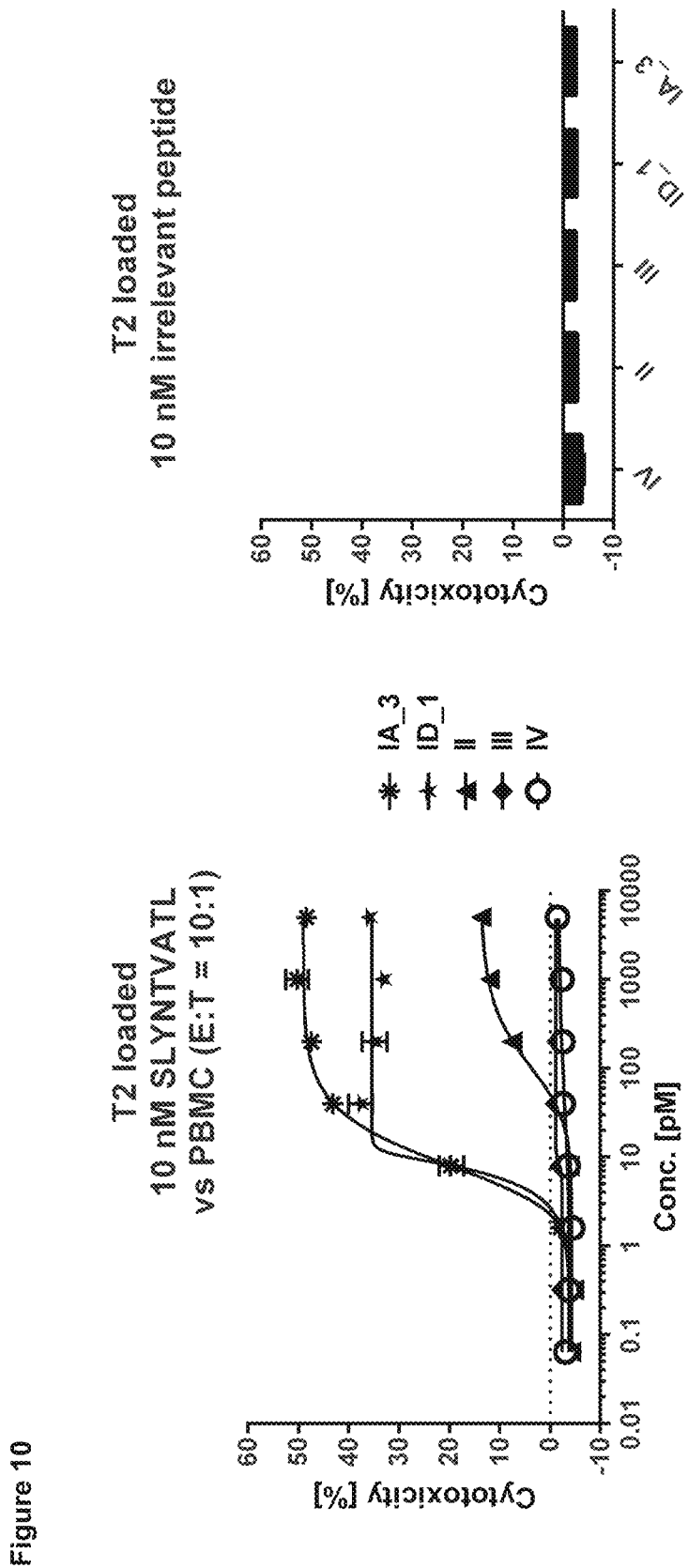
FIG. 10 shows the results of a LDH-release assay with different bispecific TCR/mAb constructs (as shown in FIG. 2) designed as IgG1-based molecules. PBMC isolated from a healthy donor were co-incubated with HIV-peptide SLYNTVATL (SEQ ID No. 7) loaded T2 cells in the presence of increasing concentrations of bispecific TCR (bssTCR) molecules. The bispecific TCR/mAb diabody molecules IA_3 and ID_1 induced markedly higher lysis of target cells than three alternative dual specificity TCR/mAb molecules. As shown on the right hand sided graph none of the tested bispecific TCR/mAb constructs induced detectable lysis of T2 cells loaded with irrelevant peptide (SEQ ID No. 49).

Furthermore LDH-release assay (Promega) was used to quantify the PBMC-mediated lysis of SLYNTVATL (SEQ ID No. 7) peptide-loaded T2 cells induced by the different bispecific TCR/mAb molecules (FIG. 10). In line with the above results of the T Cell Activation Bioassay, again the Fc-containing TCR/mAb diabody constructs IA and ID were superior over the alternative bispecific TCR/mAb constructs II, III and IV as indicated by the increased absolute level of target cell lysis and the lower TCR bispecific concentration needed to achieve half-maximal (EC50) killing of target cells. As for TCR/mAb constructs II, III and IV, the TCR/mAb diabody constructs IA and ID did not induce lysis of T2 cells loaded with irrelevant peptide(SEQ ID No. 49), proving the target-specific lysis to the T2 cells.

Example 4

Development of Fc-Containing Bispecific TCR/mAb Diabodies as a Molecular Platform Fc-containing bispecific TCR/mAb diabody constructs were designed to serve as molecular platform to provide the scaffold for different TCR-derived and mAb-derived variable domains targeting different peptide:MHC complexes and effector cell surface antigens, respectively. To validate the suitability as platform, the mAb-derived variable domains were exchanged in a first set of molecules. The variable domains of hUCHT1(V9) anti-CD3 antibody (construct ID_1) were replaced against the domains of the hBMA031(var10) anti-TCR antibody employing the same domain orientation (constructs ID_4 and ID_5) or a different orientation (IC_4, IC_5) (see Table 1 and FIG. 7 for details). Expression, purification and characterization of these molecules were performed as described above. Purity and integrity of final preparations exceeded 92% according to HPLC-SEC analyses.

Figure 6:
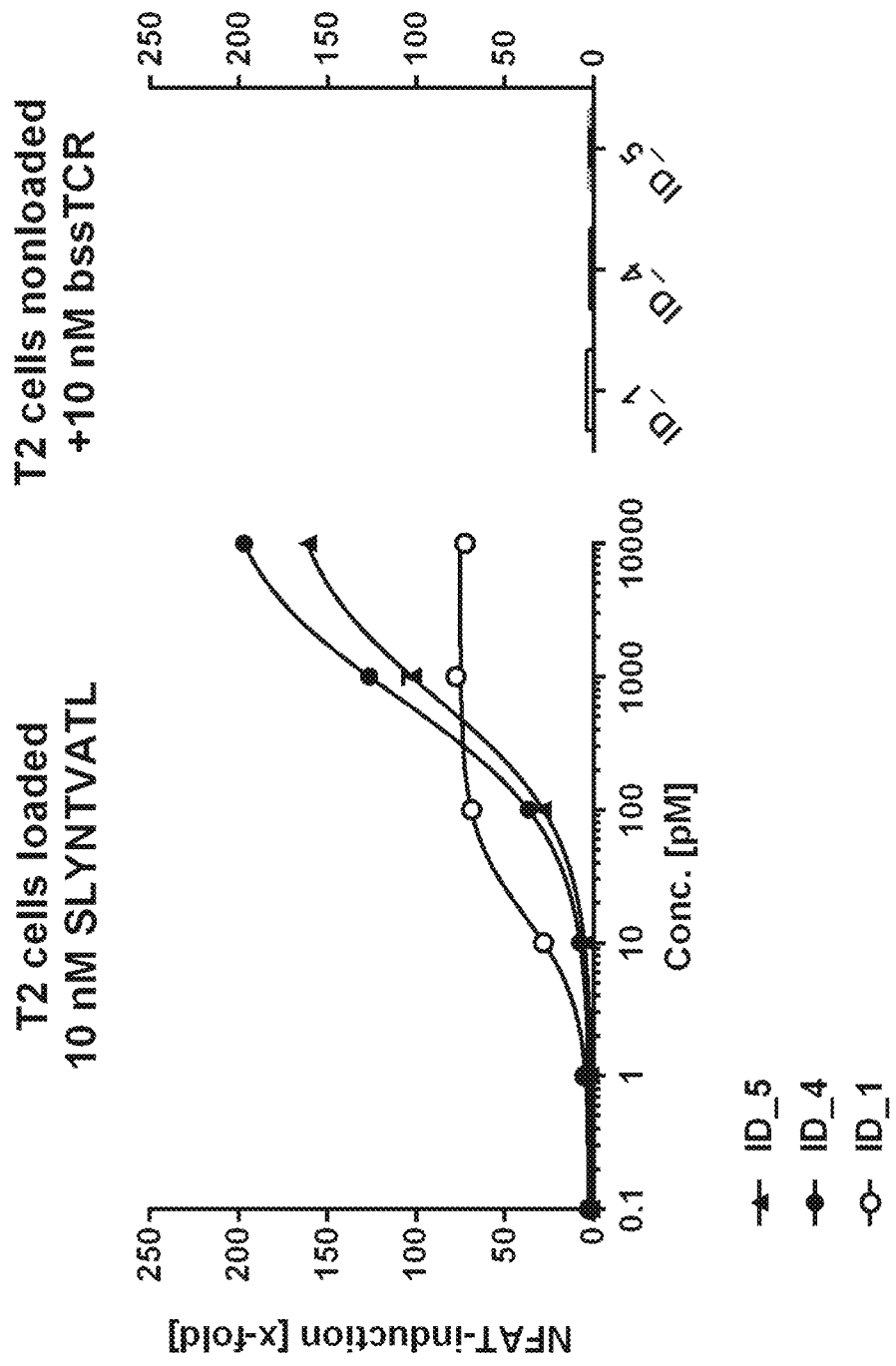
FIG. 6 shows the results of the potency assay conducted with different IgG1-based bispecific TCR/mAb constructs (as shown in FIG. 2) utilizing different variable antibody domains both targeting the TCR-CD3 complex. Construct ID_1 comprises variable domains of the UCHT1(V9) antibody targeting CD3, whereas the constructs ID_4 and ID_5 comprise variable domains of the alpha/beta TCR-specific antibody BMA031. Jurkat_NFATRE_luc2 cells were co-incubated with HIV-peptide SLYNTVATL (SEQ ID No. 7) loaded T2 cells in the presence of increasing concentrations of bispecific TCR (bssTCR) molecules.
Figure 7A:
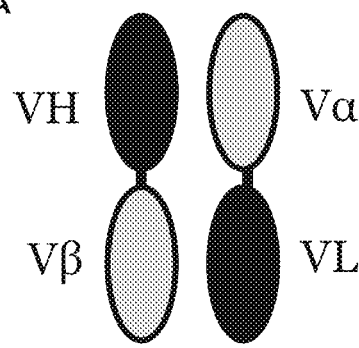
FIGS. 7A, 7B, 7C, and 7D show a schematic overview over the possible orientations of the VD and VR domains in the molecules of the present invention. VH: antibody-derived VH-domain, VL: antibody-derived VL-domain; Vα: TCR-derived Valpha; Vβ: TCR-derived Vbeta.
Figure 7B:
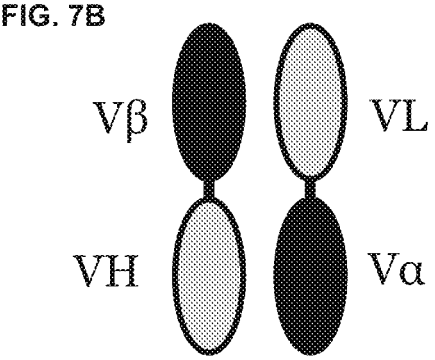
Figure 7C:
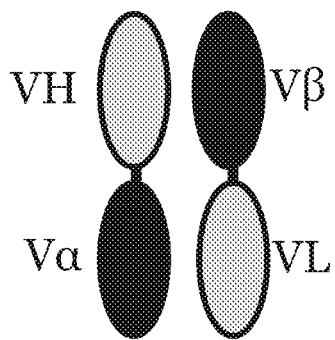
Figure 7D:
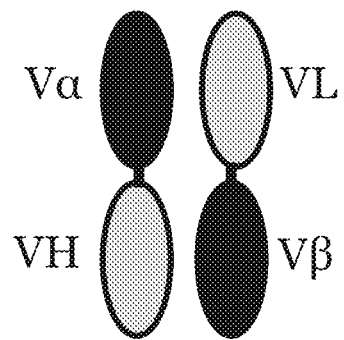

The potency assay results revealed target-dependent Jurkat reporter T cell activation and minimal unspecific activity against unloaded T2 cells for both antibody variable domains hUCHT1 (construct ID_1) and hBMA031 (constructs ID_4 and ID_5) supporting the platform suitability of the dual specificity TCR/mAb diabody constructs (FIG. 6). Notably, when the variable TCR and mAb domains of the constructs ID_4 and ID_5 were switched on each polypeptide chain resulting in constructs IC_4 and IC_5 no T cell activation was observed (data not shown). The latter finding indicate that despite bispecific TCR/mAb diabodies can be used as platform construct for incorporating different TCR and mAb variable domains a thorough optimization of the domain orientation is required to achieve optimal activity of the molecules.

Example 5

Stability of Fc-Containing Bispecific TCR/mAb Diabodies

Stability of the bispecific TCR/mAb molecules was initially assessed utilizing the Protein Thermal Shift Assay (Thermo Fisher Scientific) according to the instructions of the manufacturer using a 7500 Real time PCR system (Applied Biosciences). Briefly, purified molecules were mixed with PTS buffer and PTS dye and subjected to a raising temperature gradient constantly monitoring fluorescence of samples. Recorded fluorescence signals were analyzed using PTS software (Thermo Fisher Scientific) and melting temperatures ($T_M$) were calculated by the derivative method.

Stressed stability studies were conducted by storage of purified molecules dissolved in PBS at 40° C. for up to two weeks. Samples were analyzed with regard to protein integrity using HPLC-SEC and potency using the T Cell Activation Assay (Promega) as described above.

Figure 8:
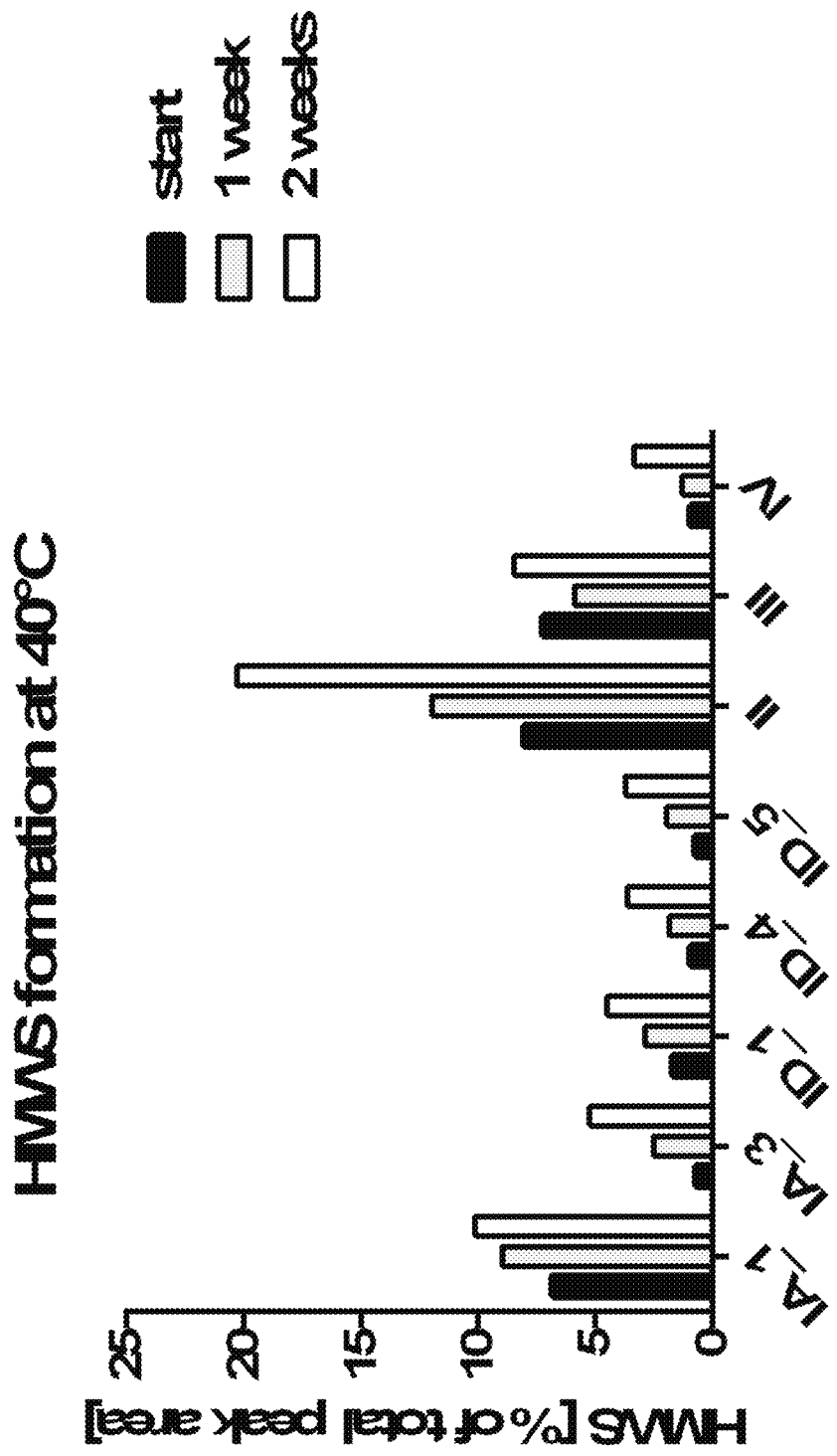
FIG. 8 shows the results of HPLC-SEC analysis of aggregates (HMWS—high molecular weight species) within different bispecific TCR/mAb molecules based on IgG1. Aggregates were analyzed after purification and after storage of the molecules at 40° C. for 1 weeks and 2 weeks, respectively.
Figure 9:
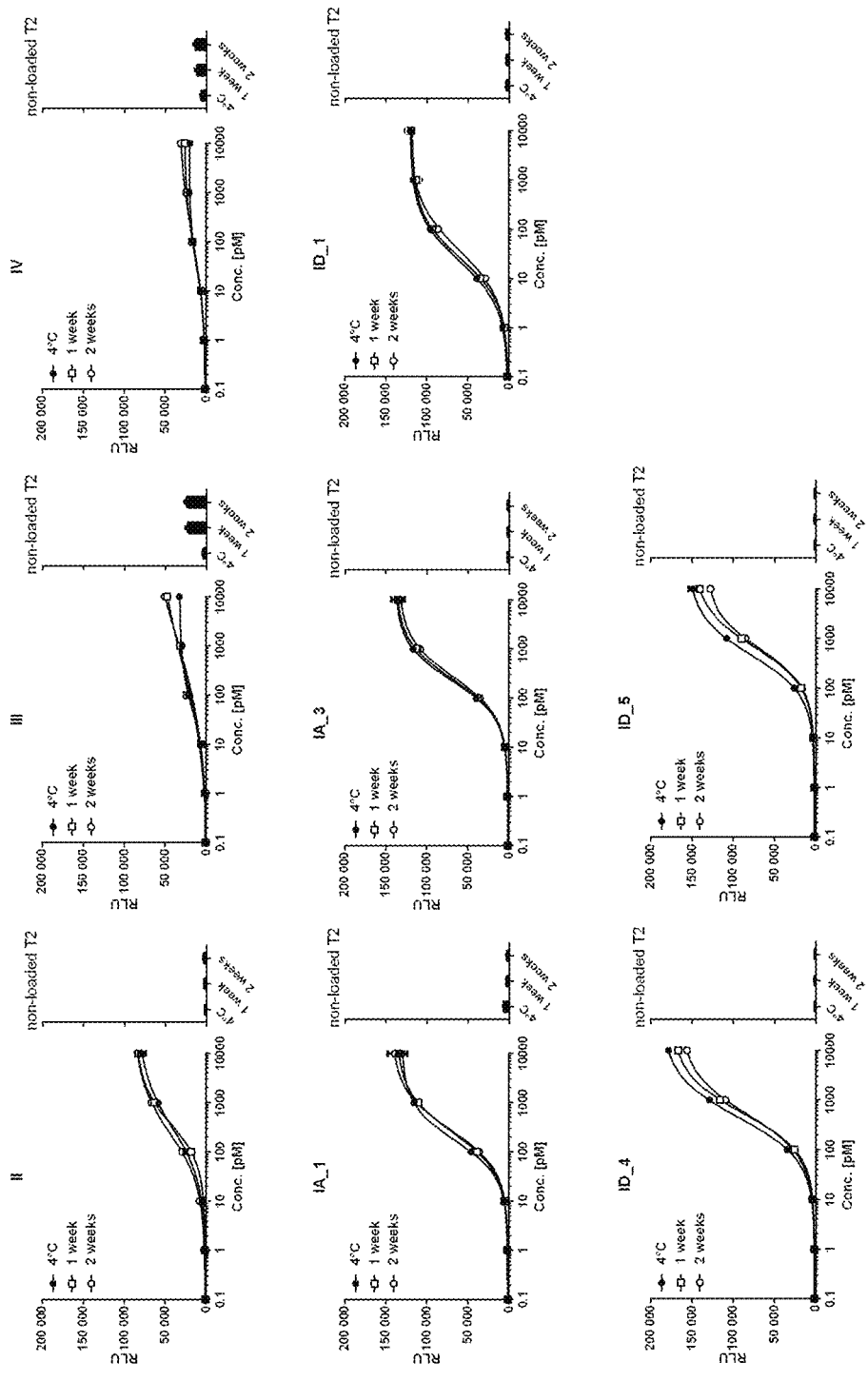
FIG. 9 shows the results of the potency assay conducted with different bispecific TCR/mAb molecules based on IgG1. Potency was analyzed after purification and after storage of the molecules at 40° C. for 1 week and 2 weeks, respectively. Stress storage at 40° C. did not lead to significant loss of potency of the molecules but a drastic increase in unspecific (i.e. target-independent) activation of Jurkat T cells was detected for the molecules Ill and IV.

As expected storage at 40° C. induced the formation of aggregates/high-molecular weight species as determined by HPLC-SEC analyses (see FIG. 8). Results of potency assays of IgG1-based molecules after purification and incubation at 40° C. are shown in FIG. 9. Although neither of the tested molecules did show a significant reduction of potency after storage at 40° C., it was observed that the stressed molecules III and IV induced a significant amount of unspecific (i.e. target-independent) Jurkat T cell activation. In contrast, the bispecific TCR/mAb diabodies retained their target-dependent potency, despite the presence of some aggregates as seen in HPLC-SEC.

Example 6

Generation of Cancer-Targeting Bispecific TCR/mAb Diabody Molecules

To further validate the platform capabilities of bispecific TCR/mAb diabody constructs, the TCR-derived variable domains were exchanged with variable domains of a TCR, which was stability/affinity maturated by yeast display according to a method described previously (Smith et al, 2015, T Cell Receptor Engineering and Analysis Using the Yeast Display Platform. Methods Mol Biol. 1319:95-141). The TCR variable domains specifically binding to HIV-derived peptide SLYNTVATL (SEQ ID No. 7) in the context HLA-A*02 were exchanged with TCR variable domains specifically binding to the tumor-associated peptide PRAME-004 (SEQ ID No. 49) bound to HLA-A*02. Furthermore, the variable domains of the humanized T-cell recruiting antibody hUCHT1(V9) were exchanged against variable domains of hUCHT1(Var17), a newly humanized version of the UCHT1 antibody, resulting in the PRAME-004-targeting TCR/mAb diabody molecule IA_5 (comprising SEQ ID No. 43 and SEQ ID No. 44). Expression, purification and characterization of this molecule was performed as described in Example 2. Purity and integrity of final preparation exceeded 96% according to HPLC-SEC analysis.

Binding affinities of bispecific TCR/mAb diabody constructs towards PRAME-004:HLA-A*02 were determined by biolayer interferometry. Measurements were done on an Octet RED384 system using settings recommended by the manufacturer. Briefly, purified bispecific TCR/mAb diabody molecules were loaded onto biosensors (AHC) prior to analyzing serial dilutions of HLA-A*02/PRAME-004.

The activity of this PRAME-004-targeting TCR/mAb diabody construct with respect to the induction of tumor cell lysis was evaluated by assessing human CD8-positive T cell-mediated lysis of the human cancer cell lines UACC-257, SW982 and U2OS presenting different copy numbers of PRAME-004 peptide in the context of HLA-A*02 on the tumor cell surface (UACC-257—about 1100, SW982—about 770, U2OS—about 240 PRAME-004 copies per cell, as determined by quantitative M/S analysis) as determined by LDH-release assay.

Figure 11:
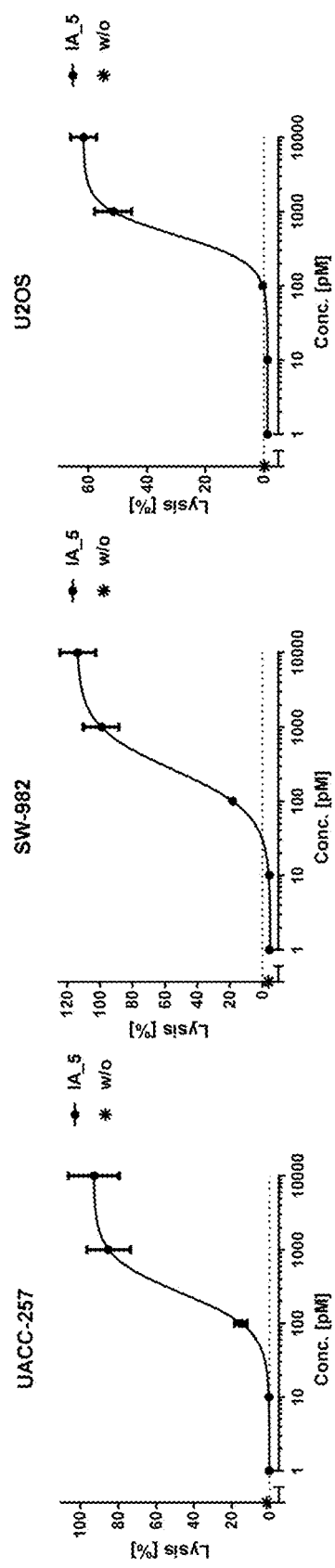
FIG. 11 shows the results of a LDH-release assay with the bispecific TCR/mAb diabody construct IA_5 targeting tumor-associated peptide PRAME-004 (SEQ ID No. 49) presented on HLA-A*02. CD8-positive T cells isolated from a healthy donor were co-incubated with cancer cell lines UACC-257, SW982 and U2OS presenting differing amounts of PRAME-004:HLA-A*02-1 complexes on the cell surface (approx. 1100, approx. 770 and approx. 240 copies per cell, respectively, as determined by M/S analysis) at an effector: target ratio of 5:1 in the presence of increasing concentrations of TCR/mAb diabody molecules. After 48 hours of co-culture target cell lysis was quantified utilizing LDH-release assays according to the manufacturer's instructions (Promega).

As depicted in FIG. 11, the PRAME-004-targeting TCR/mAb diabody construct IA_5 induced a concentration-dependent lysis of PRAME-004 positive tumor cell lines. Even tumor cells U2OS expressing as little as 240 PRAME-004 copy numbers per tumor cell were efficiently lysed by this TCR/mAb diabody molecule. These results further demonstrate that TCR/mAb diabody format is applicable as molecular platform allowing to introduce variable domains of different TCRs as well as variable domains of different T cell recruiting antibodies.

Example 7

Engineerability of TCR/mAb Diabody Constructs

The variable TCR domains utilized in construct IA_5 were further enhanced regarding affinity towards PRAME-004 and TCR stability, and used for engineering into TCR/mAb diabody scaffold resulting in construct IA_6 (comprising SEQ ID No. 45 and SEQ ID No. 46). Expression, purification and characterization of TCR/mAb diabody molecules IA_5 and IA_6 were performed as described in example 2. Purity and integrity of final preparations exceeded 97% according to HPLC-SEC analysis.

Potency of the stability and affinity enhanced TCR/mAb diabody variant IA_6 against PRAME-004 was assessed in cytotoxicity experiments with the tumor cell line U2OS presenting low amounts of PRAME-004:HLA-A*02 or non-loaded T2 cells as target cells and human CD8-positive T cells as effector cells.

Figure 12:
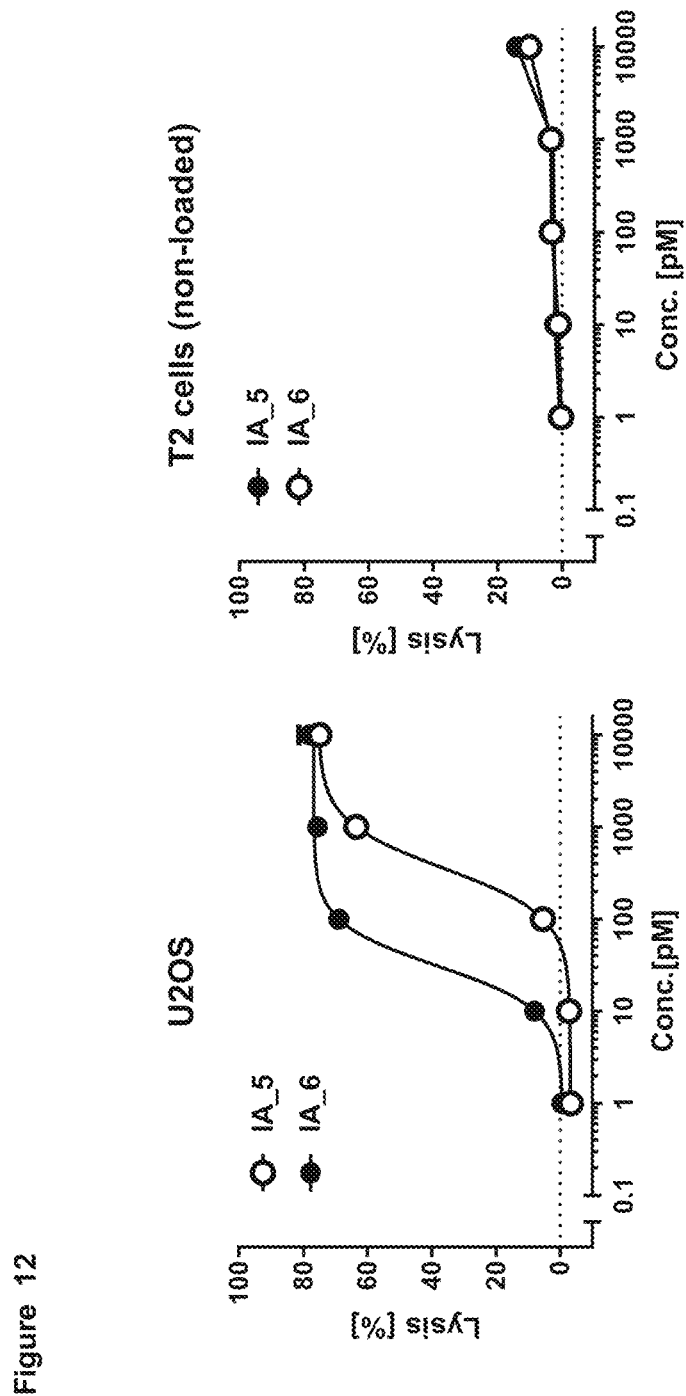
FIG. 12 shows the results of a LDH-release assay with the bispecific TCR/mAb diabody constructs IA_5 and IA_6 utilizing a stability/affinity maturated TCR and an enhanced version thereof, respectively, against the tumor-associated peptide PRAME-004 (SEQ ID No. 49) presented on HLA-A*02. CD8-positive T cells isolated from a healthy donor were co-incubated with the cancer cell line U2OS presenting approx. 240 copies per cell of PRAME-004:HLA-A*02-1 complexes or non-loaded T2 cells (effector:target ratio of 5:1) in the presence of increasing concentrations of TCR/mAb diabody molecules. After 48 hours of coculture target cell lysis was quantified utilizing LDH-release assays according to the manufacturer's instructions (Promega).

As depicted in FIG. 12, the inventors observed and increased cytotoxic potency of the TCR/Ab diabody molecule IA_6 comprising the variable domains of the stability/affinity enhanced TCR variant when compared to the precursor construct IA_5. For both constructs, IA_5 and IA_6, the PRAME-004-dependent lysis could be confirmed as no cytolysis of target-negative T2 cells was detected.

Figure 13:
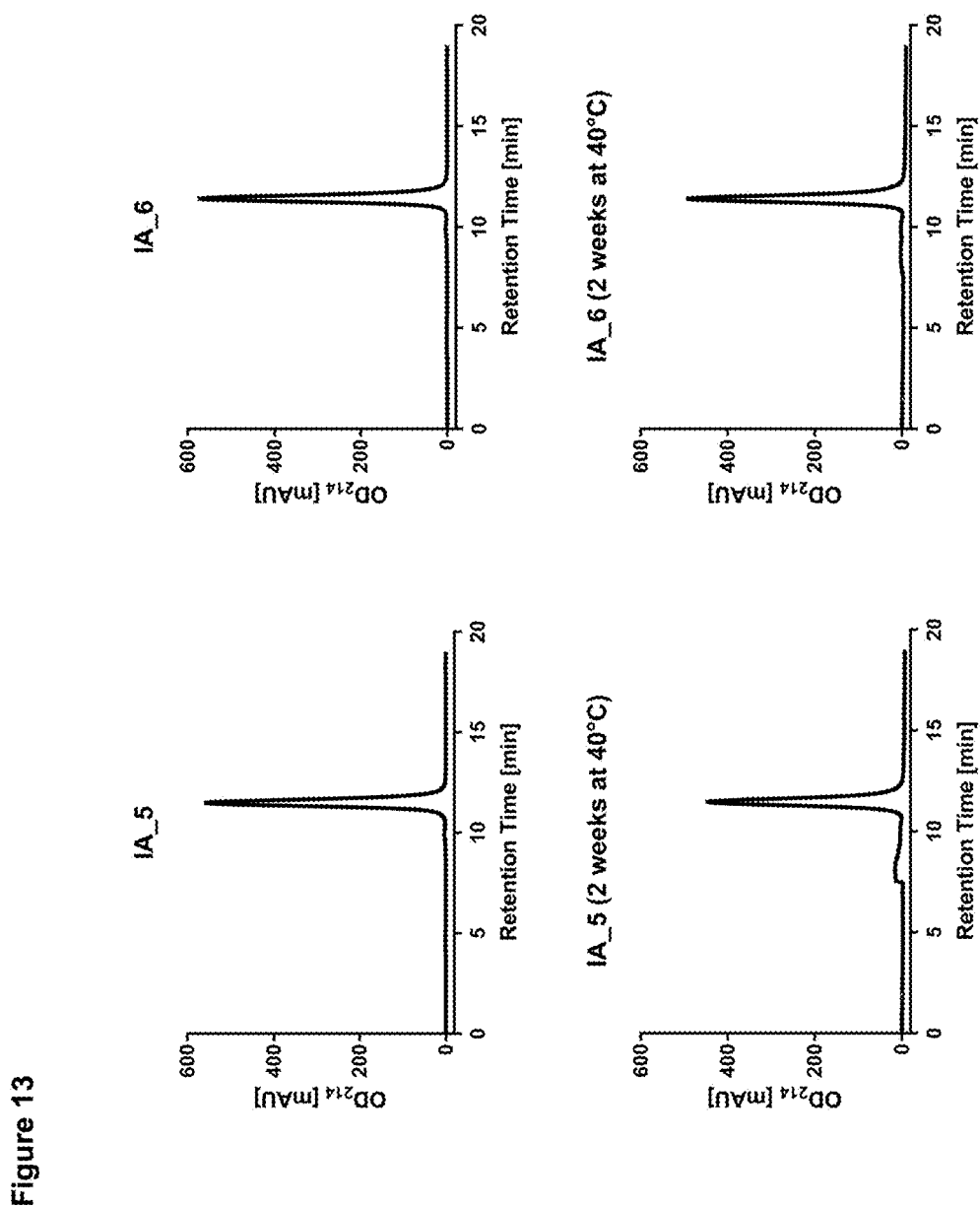
FIG. 13 shows the results of a heat-stress stability study of the TCR/mAb diabody constructs IA_5 and IA_6 utilizing a stability/affinity maturated TCR and an enhanced version thereof, respectively, against the tumor-associated peptide PRAME-004 (SEQ ID No. 49) presented on HLA-A*02. For this, the proteins were formulated in PBS at a concentration of 1 mg/mL and subsequently stored at 40° C. for two weeks. Protein integrity and recovery was assessed utilizing HPLC-SEC. Thereby the amount of high-molecular weight species was determined according to percentage of peak area eluting before the main peak. Recovery of monomeric protein was calculated by comparing main peak areas of unstressed and stressed samples.

The protein construct were further subjected to heat-stress at 40° C. for up to two weeks to analyze stability of the PRAME-004-specific TCR/mAb diabody variants IA_5 and IA_6. HPLC-SEC analyses after heat-stress revealed a significantly improved stability of the variant IA_6 when compared to the precursor construct IA_5 (see FIG. 13). The temperature-induced increase of high-molecular species (i.e. eluting before the main peak) of the constructs was less pronounced for IA_6 than for IA_5. In line with this result, the recovery of intact, monomeric protein after heat-stress was 87% and 92% for IA_5 and IA_6, respectively.

These exemplary engineering data demonstrate that the highly potent and stable of TCR/mAB diabody constructs can further be improved by incorporating stability/affinity enhanced TCR variable domains resulting in therapeutic proteins with superior characteristics.

Example 8

Examples for Preferred Constructs

In addition to the HIV-specific TCR bispecific construct as described herein (Seq ID No. 16 and Seq ID No. 17, in orientation D), the invention further provides several other exemplary HIV-specific constructs that were tested. These constructs are based on an improved humanized variants of the underlying antibody against CD3 (UCHT1) that were fused with the HIV-specific TCR 868 as disclosed herein in all four possible orientations (Seq ID No. 51 to Seq ID No. 58, in orientations A-D).

The humanization of UCHT1 was performed using VH-1-46 and VK1-018 as acceptor frameworks for the heavy and light chain CDRs, respectively. J-segments selected were JK1 and JH4, for light and heavy chain, respectively.

The results as obtained are shown in the following Table 4:

|  | V9 (Zhu et al, 1995) | Present invention |
| --- | --- | --- |
| DRB1 score | 1232 | ~1190 |
| Titre [mg/L] | 0.75 | 3 |
| Tm of F(ab) [° C.] | 83.0 | 86.4 |
| EC50 of effector cell activation [pM] | 63 | 8 |

The data in table 4 shows that the inventive humanization is potentially less immunogenic (lower DRB1-score); the molecules are more stable (increase in melting temperature of about 3° C.); and more potent (~8× decreased EC50), compared with the standard (V9) (for assay, see example 3).

The invention claimed is:

1. A dual specificity polypeptide molecule comprising:
a first polypeptide chain and a second polypeptide chain,
wherein the first polypeptide chain has an N-terminus and a C-terminus and comprises
a first binding region of a variable domain of an antibody (VD1) that specifically binds to a cell surface antigen of a human immune effector cell, and
a first binding region of a variable domain of a TCR (VR1) that specifically binds to an MHC-associated peptide epitope, and
a first linker (LINK1) connecting the domains;
wherein the second polypeptide chain has an N-terminus and a C-terminus and comprises
a second binding region of a variable domain of a TCR (VR2) that specifically binds to an MHC-associated peptide epitope, and
a second binding region of a variable domain of an antibody (VD2) that specifically binds to a cell surface antigen of a human immune effector cell, and
a second linker (LINK2) connecting the domains;
wherein the VR1 comprises a TCR Vα domain or a TCR Vβ domain,
wherein the VR2 comprises a TCR Vα domain or a TCR Vβ domain,
wherein, when the VR1 comprises a TCR Vα domain, the VR2 comprises a TCR Vβ domain, and, when the VR2 comprises a TCR Vα domain, the VR1 comprises a TCR Vβ domain, wherein the VR1 and the VR2 associate to form a second binding site that specifically binds an MHC-associated peptide epitope,
wherein the VD1 comprises an antibody VH domain or an antibody VL domain,
wherein the VD2 comprises an antibody VH domain or an antibody VL domain,
wherein, when the VD1 comprises an antibody VH domain, the VD2 comprises an antibody VL domain, and, when the VD1 comprises an antibody VL domain, the VD2 comprises an antibody VH domain, wherein the VD1 and VD2 associate to form a first binding site that binds a cell surface antigen of a human immune effector cell;
wherein
the order of the binding regions in the first polypeptide chain from the N-terminus to the C-terminus direction is Vα-LINK1-VH and the order of the binding regions in the second polypeptide chain from the N-terminus to the C-terminus direction is VL-LINK2-Vβ, or
the order of the binding regions in the first polypeptide chain from the N-terminus to the C-terminus direction is VH-LINK1-Vβ and the order of the binding regions in the second polypeptide chain from the N-terminus to the C-terminus direction is Vα-LINK2-VL, or
the order of the binding regions in the first polypeptide chain from the N-terminus to the C-terminus direction is Vβ-LINK1-VH and the order of the binding regions in the second polypeptide chain from the N-terminus to the C-terminus direction is VL-LINK2-Vα, or
the order of the binding regions in the first polypeptide chain from the N-terminus to the C-terminus direction is VH-LINK1-Vα and the order of the binding regions in the second polypeptide chain from the N-terminus to the C-terminus direction is Vβ-LINK2-VL and
wherein the two polypeptide chains are each fused to (i) a human IgG hinge domain or dimerizing portion thereof, (ii) a human IgG Fc domain or dimerizing portion thereof, or (iii) to both (i) and (ii);
wherein the two polypeptide chains are connected by covalent, non-covalent bonds, or both between the hinge domains, between the Fc domains, or between both the hinge domains and the Fc domains; and wherein the dual specificity polypeptide molecule is capable of simultaneously binding the cell surface molecule and the MHC-associated peptide epitope.

2. The dual specificity polypeptide molecule according to claim 1, wherein the order of the binding regions in the first polypeptide chain from the N-terminus to the C-terminus direction is Vα-LINK1-VH and the order of the binding regions in the second polypeptide chain from the N-terminus to the C-terminus direction is VL-LINK2-Vβ.

3. The dual specificity polypeptide molecule according to claim 1, wherein the first and second polypeptide chains further comprise at least a hinge domain and an Fc domain or portions thereof derived from human IgG1, IgG2 or IgG4.

4. The dual specificity polypeptide molecule according to claim 3, wherein the Fc domain comprises at least one effector function silencing mutation at a residue selected from positions 233, 234, 235, 236, 297 and 331, optionally wherein the effector function silencing mutation is generated by replacing at least one residue in position 233, 234, 235, 236, and 331 with the corresponding residue derived from IgG2 or IgG4.

5. The dual specificity polypeptide molecule according to claim 1, wherein the Fc domain comprises a CH3 domain comprising at least one mutation that facilitates the formation of heterodimers.

6. The dual specificity polypeptide molecule according to claim 5, wherein the mutations are located at any position selected from 366, 368, 405, and 407, optionally, wherein the mutations comprise T366W and T366'S, L368A' and Y407'V as knob-into-hole mutations.

7. The dual specificity polypeptide molecule according to claim 1, wherein the Fc domain comprises CH2 and CH3 domain(s) comprising at least two additional cysteine residues, S354C and Y349C or L242C and K334C.

8. The dual specificity polypeptide molecules according to claim 1, wherein the domains VD1 and VD2 display an engineered disulfide bridge introducing a covalent bond between VD1 and VD2 and where the cysteines are introduced into framework region (FR) 4 of VL and framework region 2 of VH.

9. The dual specificity polypeptide molecule according to claim 1, wherein the cell surface molecule is known to induce the activation of immune cells, or is at least one selected from the group consisting of CD3γ, CD3δ, CD3ε, CD4, CD7, CD8, CD10, CD11b, CD11c, CD14, CD16, CD18, CD22, CD25, CD28, CD32a, CD32b, CD33, CD41, CD41b, CD42a, CD42b, CD44, CD45RA, CD49, CD55, CD56, CD61, CD64, CD68, CD94, CD90, CD117, CD123, CD125, CD134, CD137, CD152, CD163, CD193, CD203c, CD235a, CD278, CD279, CD287, Nkp46, NKG2D, GITR, FcεRI, TCRα/β, TCRγ/δ, and HLA-DR.

10. The dual specificity polypeptide molecule according to claim 1, wherein the molecule carries a detectable label.

11. The dual specificity polypeptide molecule according to claim 1, wherein (i) the first binding site that binds the cell surface antigen of the immune cells is humanized; (ii) the second binding site that binds the MHC-associated peptide epitope is maturated to achieve higher affinity, higher stability, or both; or both (i) and (ii).

12. A nucleic acid (i) encoding the first polypeptide chain according to claim 1, (ii) encoding the second polypeptide chain according to claim 1, or (iii) encoding (i) and (ii).

13. A pharmaceutical composition comprising the dual specificity polypeptide molecule according to claim 1 together with one or more pharmaceutically acceptable carriers or excipients.

14. A method for the treatment of a disease or disorder comprising administering a therapeutically effective amount of the dual specificity polypeptide molecule according to claim 1 to a patient in need thereof.

15. The dual specificity polypeptide molecule of claim 1, wherein the order of the binding regions in the first polypeptide chain from the N-terminus to the C-terminus direction is VH-LINK1-Vβ and the order of the binding regions in the second polypeptide chain from the N-terminus to the C-terminus direction is Vα-LINK2-VL.

16. The dual specificity polypeptide molecule of claim 1, wherein the order of the binding regions in the first polypeptide chain from the N-terminus to the C-terminus direction is Vβ-LINK1-VH and the order of the binding regions in the second polypeptide chain from the N-terminus to the C-terminus direction is VL-LINK2-Vα.

17. The dual specificity polypeptide molecule of claim 1, wherein the order of the binding regions in the first polypeptide chain from the N-terminus to the C-terminus direction is VH-LINK1-Vα and the order of the binding regions in the second polypeptide chain from the N-terminus to the C-terminus direction is Vβ-LINK2-VL.

18. A vector comprising the nucleic acid of claim 12.

19. A host cell comprising and optionally expressing the vector of claim 18.

* * * * *